US012637424B2

(12) United States Patent
Major et al.

(10) Patent No.: US 12,637,424 B2
(45) Date of Patent: May 26, 2026

(54) PHARMACEUTICAL SALT OF AN ARYLPYRROLE DERIVATIVE

(71) Applicant: SENTINEL ONCOLOGY LIMITED, Cambridge (GB)

(72) Inventors: Meriel Ruth Major, Cambridge (GB); Robert George Boyle, Cambridge (GB); Stuart Travers, Meppershall (GB); David Winter Walker, Linton (GB); Julian Scott Northen, South Shields (GB); Stefania Santoni, Gateshead (GB)

(73) Assignee: SENTINEL ONCOLOGY LIMITED, Cambridge (GB)

( * ) Notice: Subject to any disclaimer, the term of this patent is extended or adjusted under 35 U.S.C. 154(b) by 484 days.

(21) Appl. No.: 18/245,999

(22) PCT Filed: Sep. 23, 2021

(86) PCT No.: PCT/EP2021/076203
§ 371 (c)(1),
(2) Date: Mar. 20, 2023

(87) PCT Pub. No.: WO2022/063899
PCT Pub. Date: Mar. 31, 2022

(65) Prior Publication Data

US 2024/0140908 A1 May 2, 2024

(30) Foreign Application Priority Data

Sep. 25, 2020 (GB) ..................................... 2015187

(51) Int. Cl.
*C07D 207/337* (2006.01)
*A61P 35/00* (2006.01)
*C07C 59/255* (2006.01)

(52) U.S. Cl.
CPC .......... *C07D 207/337* (2013.01); *A61P 35/00* (2018.01); *C07C 59/255* (2013.01); *C07B 2200/07* (2013.01); *C07B 2200/13* (2013.01)

(58) Field of Classification Search
None
See application file for complete search history.

(56) References Cited

U.S. PATENT DOCUMENTS 5,792,778 A 8/1998 De Laszlo et al.
11,208,405 B2 * 12/2021 Boyle ................ C07D 207/335

(Continued)

FOREIGN PATENT DOCUMENTS

CA 2938547 A1 4/2012
CN 102190625 A 9/2011

(Continued)

OTHER PUBLICATIONS

Berge et al., Pharmaceutical salts. J Pharm Sci. Jan. 1977;66(1):1-19 (Year: 1977).*

(Continued)

*Primary Examiner* — Jeffrey S Lundgren
*Assistant Examiner* — Anthony Joseph Seitz
(74) *Attorney, Agent, or Firm* — HESLIN ROTHENBERG FARLEY & MESITI P.C.

(57) ABSTRACT

The present invention relates to (R)-4-[5-(4-chlorophenyl)-1-[2-(trifluoromethyl)-phenyl]pyrrol-2-yl]-N-[2-(dimethyl-amino)-ethyl]benzamide (+)-L-tartrate salt, methods for its preparation, pharmaceutical compositions containing it and its use in treating diseases such as cancer.

19 Claims, 9 Drawing Sheets

(S)-6,6'-dinitrobiphenyl-2,2'-dicarboxylic acid

(56) References Cited

U.S. PATENT DOCUMENTS

| | | | | |
|---|---|---|---|---|
| 11,884,656 | B2 * | 1/2024 | Boyle | C07D 409/04 |
| 2003/0144338 | A1 | 7/2003 | Matsumoto et al. | |
| 2004/0248896 | A1 | 12/2004 | Dean et al. | |
| 2006/0128759 | A1 | 6/2006 | Laufer et al. | |
| 2010/0317568 | A1 | 12/2010 | DeGoey et al. | |
| 2015/0079154 | A1 | 3/2015 | Zender et al. | |
| 2022/0135552 | A1 | 5/2022 | Boyle et al. | |
| 2022/0348565 | A1 * | 11/2022 | Boyle | C07D 409/04 |

FOREIGN PATENT DOCUMENTS

| | | | | |
|---|---|---|---|---|
| CN | 103922989 | A | 7/2014 | |
| CN | 105859735 | A | 8/2016 | |
| DE | 10237883 | A1 | 3/2004 | |
| EP | 1389626 | A1 | 2/2004 | |
| EP | 1813613 | A1 | 8/2007 | |
| EP | 2730565 | A1 | 5/2014 | |
| EP | 3040330 | A1 | 7/2016 | |
| JP | H10237442 | A | 9/1998 | |
| JP | 2000260567 | A | 9/2000 | |
| JP | 2002/121186 | A | 4/2002 | |
| JP | 2016106075 | A | 6/2016 | |
| RU | 2655921 | C2 | 5/2018 | |
| WO | 00/08001 | A1 | 2/2000 | |
| WO | 03/055860 | A1 | 7/2003 | |
| WO | 2005/012298 | A1 | 2/2005 | |
| WO | 2010/019909 | A1 | 2/2010 | |
| WO | 2011/049274 | A1 | 4/2011 | |
| WO | 2012/051361 | A1 | 4/2012 | |
| WO | 2012/052395 | A1 | 4/2012 | |
| WO | 2012/084711 | A1 | 6/2012 | |
| WO | 2012/143248 | A1 | 10/2012 | |
| WO | 2013152206 | A1 | 10/2013 | |
| WO | 2015121239 | A1 | 8/2015 | |
| WO | 2016/022465 | A1 | 2/2016 | |
| WO | WO-2018197714 | A1 * | 11/2018 | C07D 207/337 |
| WO | 2021/058754 | A1 | 4/2021 | |

OTHER PUBLICATIONS

Becker et al., Pharmaceutical salts: A summary on doses of salt formers from the Orange Book, European Journal of Pharmaceutical Sciences, vol. 49, Issue 4, 2013, pp. 614-623 (Year: 2013).*

International Search Report for PCT/EP2021/076203, mailed on Dec. 9, 2021.

GB2015187.4 UKIPO Search Report, mailed on Mar. 3, 2021.

Balbi, A., et al., "Synthesis and biological evaluation of novel pyrazole derivatives with anticancer activity", European Journal of Medicinal Chemistry, vol. 46, pp. 5293-5309 (2011).

Bechara, W.S., et al., "One-Pot Synthesis of 3,4,5-Trisubstituted 1,2,4-Triazoles via the Addition of Hydrazides to Activated Secondary Amides", Organic Letters, vol. 17, pp. 1184-1187 (2015).

Howe, R.K., et al., "3',4'-Diarylspiro[isobenzofuran-1(3H),5'(4'H)-isoxazol]-3-ones. Reaction of Nitrile Oxides with 3-Benzylidenephthalides", J. Org. Chem., vol. 50, pp. 903-904 (1985).

Sharshira, E.M., et al., "Synthesis and Antimicrobial Evaluation of Some Pyrazole Derivatives", Molecules, vol. 17, pp. 4962-4671 (2012).

Nun et al., "Gold(I)-catalyzed synthesis of furans and pyrroles via alkyne hydration", Catal. Sci. Technol., (2011), 1, pp. 58-61.

Cao et al., "Synthesis of 3,4,5-trisubstituted isoxazoles via 1,3-dipolar cycloaddition/$SO_2$ extrusion of benzoisothiazole-2,2-dioxide-3-ylidenes with nitrile oxides", RSC Adv., (2016), 6, pp. 22516-22525.

Levai et al., "Synthesis of 4-Aryl-3(5)-(2-hydroxyphenyl)pyrazoles by Reaction of Isoflavones and their 4-Thio Analogues with Hydrazine Derivatives", Aust. J. Chem., (2007), 60, pp. 905-914.

Cui et al., "Diversity-oriented synthesis of pyrazoles derivatives from flavones and isoflavones leads to the discovery of promising reversal agents of fluconazole resistance in Candida albicans", Bioorg. Med. Chem., (2018), 28, pp. 1545-1549.

Feldman et al., "Highly Quantum Efficient Phosphorescent Sky Blue Emitters Based on Diasteromeric Iridium(III) Complexes of Atropisomeric 5-Aryl-4H-1,2,4-triazole ligands", Organometallics, (2015), 34, pp. 3665-3669.

GB 2015187.4 UKIPO Search Report dated Mar. 3, 2021.

Eistert et al. Document No. 70:37375, retrieved from STN, entered in STN on May 12, 1984.

Cancer and Metastasis Reviews (1998), 17 (1), 91-106.

Science (1999), vol. 286, 531-537.

Cancer [online], [retrieved on Jun. 7, 2007]. Retrieved from the internet, URL http://www.nlm.nih.gov/medlineplus/cancer.html>.

Noureen, S., et al., "Strong π-delocalization and substitution effect on electronic properties of dithienylpyrrole-containing bupyridine ligands and corresponding ruthenium complexes", Dalton Trans., (2012), 41, pp. 4833-4844.

Kim, K-S., et al., "Highly Efficient Photocurrent Generation from a Self-Assembled Monolayer Film of a Novel $C_{60}$-Tethered 2,5-Dithienylpyrrole Triad", Chem. Mater., (2004), 16(24), pp. 5058-5062.

Comrie, A. M., "3,4,5-Triphenylpyrazoles", J. Chem. Soc., (1971), pp. 2807-2810.

Zhou, Z., et al., "Nonvolatile electrical switching behavior and mechanism of functional polyimides bearing a pyrrole unit: influence of different side groups", RSC Adv., (2016), 6, pp. 52798-52809.

Shi et al., "A highly sensitive, single selective, real-time and "turn-on" fluorescent sensor for $Al^{3+}$ detection in aqueous media", J. Mater. Chem, (2012), 22, pp. 19296-19302.

Tamilavan, V., et al., "Structural optimization of thiophene-(N-aryl)pyrrole-thiophene-based metal-free organic sensitizers for the enhanced dye-sensitized solar cell performance", Tetrahedron, (2014), 70, pp. 371-379.

Kim, T., et al., "A Novel Method for the Synthesis of 2,3-Benzo-1,3a,6a-triazapentalenes through Pummer Type Reactions of γ-(Benzotriazol-1-yl)allylic Sulfoxides", Eur. J. Chem., (2002), 3, pp. 493-502.

Yanai, H, et al., "Novel Emitting Materials of Organic Electroluminescent Device: 1-Aryl-2,5-di(2-thienyl)pyrrole Derivates Having an Electron-withdrawing Group", Chemistry Letters, (2000), 29(3), pp. 238-239.

CAS registry No. 952009-27-7, Entry date Oct. 30, 2007, 2, 2'-[1-(4-methylphenyl)-1Hpyrrole-2,5-diyl]bis-benzoic acid.

CAS registry No. 952009-23-3, Entry date Oct. 30, 2007, 2, 2'-[1-phenyl-1H-pyrrole-2,5-diyl]bisbenzoic acid.

CAS registry No. 952009-19-7, Entry date Oct. 30, 2007, 2, 2'-[1-phenyl-1H-pyrrole-2,5-diyl]bis-(1,1'-diethyl benzoate).

CAS registry No. 1349999-41-2, Entry date Dec. 7, 2011, 4-[5-(4-chlorophenyl)-4-(3-hydroxyphenyl)-1H-pyrazol-1-benzenesulfonamide.

Marsili et al., "Rearrangements of phthalimidine derivatives formation of a pyrrole and a benzazepine from 3-(α-bromobenzylidene)-2-(β-phenethyl) phthalimidine", Tetrahedron Lett. (1969), 10(11), pp. 887-890.

Kong Kai-lai et al., "Research progress of antitumor Polo-like kinase 1 inhibitors", Journal of China Pharmaceutical University, (2011), 42(1), pp. 9-15 (with English Translation).

Laplante et al, "Assessing Atropisomer Axial Chirality in Drug Discovery and Development", J. Med. Chem., (2011), 54(2), pp. 7005-7022.

Bringmann et al., "Atroposelective Synthesis of Axially Chiral Biaryl Compounds", Angew. Chem. Int. Ed., (2005), 44(34), pp. 5384-5427.

Clayden et al., "The Challenge of Atropisomerism in Drug Discovery", Angew. Chem. Int. Ed., (2009), 48(35), pp. 6398-6401.

Kharkevich D.A., Pharmacolology: Textbook, (2010), 10th edition, pp. 72-82.

Durnov L.A., Goldobenko G.V., Children's Oncology, Moscow, "Medicine", (2002), p. 139.

(56) References Cited

OTHER PUBLICATIONS

Small Medical Encyclopedia, T.5, Moscow, “Medicine”, (1996), pp. 90-96.

* cited by examiner (S)-6,6'-dinitrobiphenyl-2,2'-dicarboxylic acid

R

S

U87MG Subcutaneous Xenograft Model

PHARMACEUTICAL SALT OF AN ARYLPYRROLE DERIVATIVE

CROSS REFERENCE TO RELATED APPLICATIONS

This application is a national stage filing under section 371 of International Application No. PCT/EP2021/076203, filed on Sep. 23, 2021, and published on Mar. 31, 2022 as WO 2022/063899, which claims priority to United Kingdom Application No. 2015187.4, filed on Sep. 25, 2020. The entire contents of WO 2022/063899 are hereby incorporated by reference herein.

This invention relates to a pharmaceutical salt of an atropisomer of a tri-aryl pyrrole compound, methods for its preparation, pharmaceutical compositions containing it and its use in treating diseases such as cancer.

BACKGROUND OF THE INVENTION

The protein expressed by the normal KRAS gene performs an essential function in normal tissue signalling. The mutation of a KRAS gene by a single amino acid substitution, and in particular a single nucleotide substitution, is responsible for an activating mutation which is an essential step in the development of many cancers. The mutated protein that results is implicated in various malignancies, including lung adenocarcinoma, mucinous adenoma, ductal carcinoma of the pancreas and colorectal carcinoma. Like other members of the Ras family, the KRAS protein is a GTPase and is involved in many signal transduction pathways.

KRAS acts as a molecular on/off switch. Once it is turned on, it recruits and activates proteins necessary for the propagation of growth factor and other receptors' signals such as c-Raf and PI-3 Kinase. Normal KRAS binds to GTP in the active state and possesses an intrinsic enzymatic activity which cleaves the terminal phosphate of the nucleotide converting it to GDP. Upon conversion of GTP to GDP, KRAS is turned off. The rate of conversion is usually slow but can be sped up dramatically by an accessory protein of the GTPase-activating protein (GAP) class, for example RasGAP. In turn KRAS can bind to proteins of the Guanine Nucleotide Exchange Factor (GEF) class, for example SOS1, which forces the release of bound nucleotide. Subsequently, KRAS binds GTP present in the cytosol and the GEF is released from ras-GTP. In mutant KRAS, its GTPase activity is directly removed, rendering KRAS constitutively in the active state. Mutant KRAS is often characterised by mutations in codons 12, 13, 61 or mixtures thereof.

The viability of cancer cells carrying a mutant KRAS is known to be dependent on Polo-Like Kinase 1 (PLK1) and it has been shown that silencing PLK1 leads to the death of cells containing mutant KRAS (see Luo et al., *Cell.* 2009 May 29; 137(5): 835-848). Compounds that inhibit PLK1 should therefore be useful in treating cancers that arise from KRAS mutations, but current kinase inhibitors designed to bind to the conserved ATP-binding domain of PLK1 may be too unselective versus other kinases to access this mode-of-action (see for example Elsayed et al., *Future Med. Chem.* (2019) 11(12), 1383-1386).

PLK1 is a serine/threonine kinase consisting of 603 amino acids and having a molecular weight of 66 kDa and is an important regulator of the cell cycle. In particular, PLK1 is important to mitosis and is involved in the formation of and the changes in the mitotic spindle and in the activation of CDK/cyclin complexes during the M-phase of the cell cycle.

All Polo-like kinases contain an N-terminal Serine/Threonine kinase catalytic domain and a C-terminal region that contains one or two Polo-boxes (Lowery et al., *Oncogene*, (2005), 24, 248-259). For Polo-like kinases 1, 2, and 3, the entire C-terminal region, including both Polo-boxes, functions as a single modular phosphoserine/threonine-binding domain known as the Polo-box domain (PBD). In the absence of a bound substrate, the PBD inhibits the basal activity of the kinase domain. Phosphorylation-dependent binding of the PBD to its ligands releases the kinase domain, while simultaneously localizing Polo-like kinases to specific subcellular structures.

It has been shown (Reindl et al., *Chemistry & Biology,* 15, 459-466, May 2008) that, because PLKL1 localizes to its intracellular anchoring sites via its polo-box domain, the action of PLK1 can be inhibited by small molecules which interfere with its intracellular localization by inhibiting the function of the PBD.

Tumour protein p53 functions as a tumour suppressor and plays a role in apoptosis, genomic stability and inhibition of angiogenesis. It is known that tumours with both p53-deficiency and high PLK1 expression may be particularly sensitive to PLK1 inhibitors (Yim et al., *Mutat Res Rev Mutat Res*, (2014). 761, 31-39).

The evidence in the literature thus suggests that small molecules that bind to and inhibit the function of the PBD should be effective inhibitors of PLK1 kinase and therefore should also be useful in the treatment of cancers arising from KRAS and/or p53 mutations. In particular, since PBD domains only reside in PLKs, the potential for inhibitors designed to this domain to have greater selectivity over previous ATP-competitive inhibitors, may enable a greater ability to target KRAS mutant and p53 deficient cancers.

The identification and development of drugs for treating primary brain cancers has proved to be particularly challenging. Targeted cancer therapies, and in particular therapies using protein kinase inhibitors, have been a major focus for pharmaceutical and biotechnology companies (Nature Reviews Clinical Oncology 2016, 13, 209-227). However, although over thirty kinase inhibitors have been approved for use in oncology, none of these have been for the treatment of primary brain cancer. A particular problem has been that most of the approved kinase inhibitor oncology drugs lack the necessary drug substance qualities to achieve the brain exposure needed if they are to be of use in the treatment of brain cancer [JMC 2016, 59(22), 10030-10066].

The alkylating agent temozolomide (Temodar®, Temodal®) is currently the first line treatment for the brain cancer glioblastoma multiforme and is frequently used in combination with radiation therapy. However, drug resistance is a major problem in the management of glioblastoma and therefore limits the usefulness of temozolomide. At the present time, therefore, malignant glioblastoma remains incurable.

Polo like kinase 1 (PLK1) is overexpressed in a range of tumour types including glioblastoma multiforme (Translational Oncology 2017, 10, 22-32). Furthermore, recent studies have shown that PLK1 drives checkpoint adaptation and resistance to temozolomide in glioblastoma multiforme [Oncotarget 2017, 8, 15827-15837].

Ependymomas are tumours of the brain and spinal cord with current standard of care limited to surgery and radiation. PLK1 has been implicated in Ependymomas and inhibitors of PLK1 are active against Ependymoma cell lines [Gilbertson et. al., Cancer Cell (2011) 20, 384-399].

PLK1 has also been investigated as a target for Diffuse Intrinsic Pontine Glioma (DIPG), a high grade, aggressive childhood brain tumour [Amani et al. BMC Cancer (2016) 16, 647 and Cancer Biology and Therapy (2018) 19, 12, 1078-1087]

More specifically, inhibition of PLK1 has been shown to enhance temozolomide efficacy in IDH1 mutant gliomas [Oncotarget, (2017) 8, 9, 15827-15837] and to inhibit tumour growth in an MMR-deficient, temozolomide-resistant glioblastoma xenograft model [Mol Cancer Ther; 17(12) December 2018]

In the cases above, current inhibitors lack sufficient brain exposure.

Compounds that inhibit PLKL1, but without inducing drug resistance, and which exhibit good brain exposure would be expected to be useful in the treatment of glioblastoma multiforme and other brain cancers.

PLK4 is a polo-like kinase family member of the serine/threonine kinases that plays a critical role in centrosome duplication, acting as a central regulator of centriole duplication (Bettencourt-Dias, Curr Biol. 2005 15(24); 2199-207). PLK4 dependent alterations in centrosomes can lead to asymmetric chromosome segregation at mitosis, which can trigger cell death after chromosome mis-segregation and mitotic defects.

PLK4 is aberrantly expressed in human cancers and is implicated in tumorigenesis and metastasis. As such PLK4 has been highlighted as a promising target for cancer therapy (Zhao, J Canc Res Clin Oncol., 2019).

PLK4 is overexpressed in many cancers including rhabdoid tumours, medulloblastoma and other embryonal tumours of the brain (Pediatr Blood Cancer. 2017), as well as breast, lung, melanoma, gastric, colorectal, pancreatic and ovarian cancer. Elevated or hyperactivated PLK4 is associated with poor survival rates in cancer patients, including ovarian, breast and lung cancers (Zhao, J Canc Res Clin Oncol., 2019).

PLK4 inhibition has been studied for the treatment of glioblastoma multiforme and it has been demonstrated that PLK4 plays a critical role in the regulation of temozolomide chemosensitivity. The combination of temozolomide with inhibition of PLK4 in glioblastoma PDX models has been shown to enhance the anti-tumor effects compared to temozolomide alone (Cancer Letters, Vol 443, 2019, 91-107).

PLK4 is reported to cooperate with p53 inactivation in cancer development, and it is predicted that cancers with PLK4 overexpression and p53 deficiency are prone to form tumours (Sercin, 2016; Nat Cell Biol 18:100-110). Therefore, compounds that inhibit PLK4 activity would be anticipated to be useful in the treatment of p53 mutant cancers.

Inhibition of PLK4 results in anti-tumour activity in lung cancer, with activity seen in cancers bearing wildtype and mutant KRAS (Kawakami, PNAS 2018, 115(8) 1913-18). Therefore, compounds that inhibit PLK4 activity would be anticipated to be useful in the treatment of KRAS mutant cancers.

Current PLK4 inhibitors act at the kinase active site and are not optimal for brain penetration (Int. J. Mol. Sci. 2019, 20, 2112). Therefore, compounds that inhibit PLK4 PBD but also exhibit good brain exposure would be anticipated to be useful in the treatment of glioblastoma multiforme and other brain cancers.

Our earlier International patent application WO2018/197714 discloses compounds of the formula:

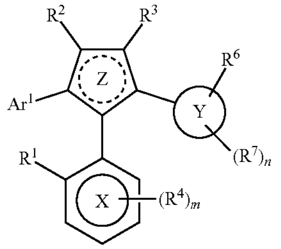

in which ring X is a benzene or pyridine ring, ring Y is a benzene, pyridine, thiophene or furan ring, $Ar^1$ is an optionally substituted benzene, pyridine, thiophene or furan ring, and $R^1$ to $R^4$, $R^6$, $R^7$ are hydrogen or various substituents. The compounds are described as having anti-cancer activity and having good brain exposure after oral dosing, making them good candidates for the treatment of brain cancers. The compounds are active against glioblastoma cell lines and are believed to act as inhibitors of the Polo Box Domain of PLK1 kinase. It is also disclosed that the compounds are active against mutant-RAS cancer cell lines (such as HCT116) and should also be useful in the treatment of cancers arising from KRAS mutations.

The Invention

It has now been found that the compound of Example 33 in WO2018/197714, namely 4-[5-(4-chlorophenyl)-1-[2-(trifluoromethyl)phenyl]pyrrol-2-yl]-N-[2 (dimethylamino)ethyl]benzamide, and its analogues, form atropisomers.

Atropisomers are stereoisomers resulting from hindered rotation about a single bond axis where the energy barrier to rotation barrier is sufficiently high to allow for the isolation of the individual rotational isomers; see LaPlante et al., *J. Med. Chem.,* 54:7005-7022 (2011).

Atropisomers can be classified into three categories based on the amount of energy needed for the chiral axis to racemize via rotation and the length of time required for racemization to occur. Class 1 atropisomers possess barriers to rotation around the chiral axis of <84 kJ/mol (20 kcal/mol) and racemize over a time period measured in minutes or less at room temperature; Class 2 atropisomers possess a barrier to rotation between 84 and 117 kJ/mol (20-28 kcal/mol) and racemize over a time period measured in hours to months at room temperature; and Class 3 atropisomers possess a barrier to rotation >117 kJ/mol (28 kcal/mol) and racemize over a period of time measured in years at room temperature.

The stereochemical structures of atropisomers can be assigned using the Cahn-Ingold-Prelog R and S system which is illustrated by (S)-6,6'-dinitrobiphenyl-2,2'-dicarboxylic acid shown in FIG. 1.

In this system, the nearest substituents either side of the aryl-aryl bond are assigned a priority in the order a-b-c-d. As the substituents a, b and c are in an anticlockwise arrangement, the atropisomer is the S isomer. In the corresponding R isomer, the substituents a, b and c are in a clockwise arrangement.

The atropisomers of 4-[5-(4-chlorophenyl)-1-[2-(trifluoromethyl)phenyl]pyrrol-2-yl]-N-[2 (dimethylamino)ethyl] benzamide and its analogues are sufficiently stable to be isolated and characterised and have been found not to racemize to any significant extent even when heated to temperatures of up to 80° C. for a period of 10 days. The atropisomers can therefore be classified as Class 3 atropisomers. It believed that the atropisomerism arises because steric interactions between the 2-trifluoromethyl substituent and the aromatic rings attached to the 2- and 5-positions of the pyrrole ring prevent rotation about the bond between the 2-trifluoromethyl-substituted ring and the nitrogen atom of the pyrrole ring.

The two individual atropisomers of 4-[5-(4-chlorophenyl)-1-[2-(trifluoromethyl)-phenyl]pyrrol-2-yl]-N-[2 (dimethylamino)ethyl]benzamide have been found to have significantly different biological properties. Thus, typically, one of two atropisomers of the pair is significantly more active against certain cancer targets than the other atropisomer of the pair. The atropisomer having better biological activity against the biological targets of interest has been shown by X-ray analysis of a single crystal to have the R configuration, i.e. the chemical structure (1):

(1)

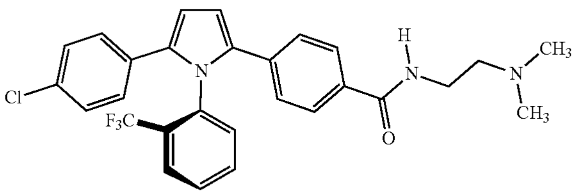

It has further been found that a (+)-L-tartaric acid salt of 4-[5-(4-chlorophenyl)-1-[2-(trifluoromethyl)-phenyl]pyrrol-2-yl]-N-[2 (dimethylamino)ethyl]benzamide, in which there is an approximately 1:1 molar ratio between acid and base, has advantages over the free base form of 4-[5-(4-chlorophenyl)-1-[2-(trifluoromethyl)-phenyl]pyrrol-2-yl]-N-[2 (dimethylamino)ethyl]benzamide and other salts of the compound.

The (+)-L-tartaric acid is particularly advantageous in that it is a highly crystalline and stable solid taking up only surface moisture (<1% at 90% RH) with improved water solubility over the free base. These properties render it particularly suitable for pharmaceutical development.

Accordingly, in a first embodiment (Embodiment 1.1), the invention provides (R)-4-[5-(4-chlorophenyl)-1-[2-(trifluoromethyl)-phenyl]pyrrol-2-yl]-N-[2-(dimethylamino)-ethyl] benzamide (+)-L-tartaric acid salt having an approximately 1:1 molar ratio between acid and base.

In further embodiments, the invention provides:

1.2 A (+)-L-tartaric acid salt of 4-[5-(4-chlorophenyl)-1-[2-(trifluoromethyl)-phenyl]pyrrol-2-yl]-N-[2 (dimethylamino)ethyl]benzamide having the formula (2):

(2)

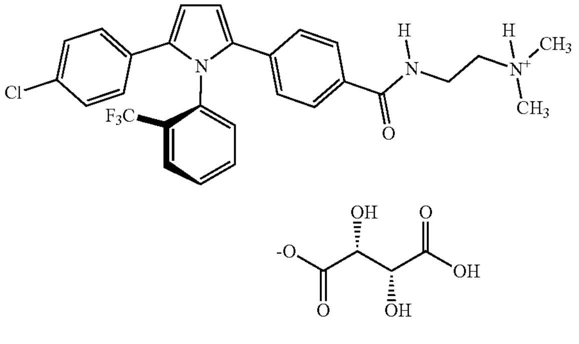

1.3 A (+)-L-tartaric acid salt of 4-[5-(4-chlorophenyl)-1-[2-(trifluoromethyl)-phenyl]pyrrol-2-yl]-N-[2 (dimethylamino)ethyl]benzamide, in which there is an approximately 1:1 molar ratio between acid and base and wherein the 4-[5-(4-chlorophenyl)-1-[2-(trifluoromethyl)-phenyl]pyrrol-2-yl]-N-[2 (dimethylamino)ethyl]-benzamide is in the form of a single atropisomer.

1.4 A (+)-L-tartaric acid salt according to Embodiment 1.3 wherein the single atropisomer is an atropisomer of formula (1).

1.5 A (+)-L-tartaric acid salt according to Embodiment 1.3 wherein the single atropisomer is the R atropisomer of 4-[5-(4-chlorophenyl)-1-[2-(trifluoromethyl)-phenyl]pyrrol-2-yl]-N-[2 (dimethylamino)ethyl]benzamide.

1.6 A (+)-L-tartaric acid salt according to Embodiment 1.3 wherein the single atropisomer is characterised by any one or more of the following parameters:

(i) X-ray crystallographic data substantially as described in Example 3 herein;

(ii) a retention time of approximately 20 minutes (e.g. approximately 20.5 minutes) when determined by Chiral HPLC method 1 herein; and (iii) a specific optical rotation, when measured using the method described in Example 2 herein, of approximately −11.76°.

1.7 A (+)-L-tartaric acid salt according to Embodiment 1.3 wherein the single atropisomer is atropisomer A-2 as described in the Examples herein.

1.8 A (+)-L-tartaric acid salt according to Embodiment 1.3 wherein the (+)-L-tartaric acid salt is as described in the Examples herein.

1.9 A (+)-L-tartaric acid salt according to any one of Embodiments 1.1 to 1.8 which is in a crystalline form.

1.10 A (+)-L-tartaric acid salt according to Embodiment 1.9 which is an anhydrate.

1.11 A (+)-L-tartaric acid salt according to Embodiment 1.10 which is the anhydrate identified herein as Pattern B.

1.12 A (+)-L-tartaric acid salt according to Embodiment 1.9 which is a solvate.

1.13 A (+)-L-tartaric acid salt according to Embodiment 1.12 which is the solvate identified herein as Pattern A.

1.14 A composition of matter comprising the (+)-L-tartaric acid salt of any one of Embodiments 1.3 to 1.13 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 10% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino)ethyl] benzamide.

1.15 A composition of matter according to Embodiment 1.14 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 5% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino) ethyl]benzamide.

1.16 A composition of matter according to Embodiment 1.14 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 2% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino) ethyl]benzamide.

1.17 A composition of matter according to Embodiment 1.14 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 1.5% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino)ethyl]benzamide.

1.18 A composition of matter according to Embodiment 1.14 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 1% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino) ethyl]benzamide.

1.19 A composition of matter according to Embodiment 1.14 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 0.1% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino)ethyl]benzamide.

Definitions

The (R)-4-[5-(4-chlorophenyl)-1-[2-(trifluoromethyl)-phenyl]pyrrol-2-yl]-N-[2-(dimethylamino)-ethyl]benzamide (+)-L-tartaric acid salt, the compound of formula (2) and the compositions of matter as defined in any one of Embodiments 1.1 to 1.19 may be referred to collectively or generically as the "tartrate salt of the invention". A reference to a "tartrate salt of the invention" may therefore be taken to be a reference to any one of Embodiments 1.1 to 1.19 unless the context indicates to the contrary.

Isotopes

The compositions of matter, compounds or salts as defined in any one of Embodiments 1.1 to 1.19 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$ The isotopes may be radioactive or non-radioactive. In one embodiment of the invention, the composition of matter or atropisomers contain no radioactive isotopes. Such compounds are preferred for therapeutic use. In another embodiment, however, the composition of matter or atropisomer may contain one or more radioisotopes. Compounds containing such radioisotopes may be useful in a diagnostic context.

Solvates and Anhydrates

The compositions of matter, compounds or salts as defined in any one of Embodiments 1.1 to 1.19 may form solvates and anhydrates.

Particular solvates are solvates formed by the incorporation into the solid state structure (e.g. crystal structure) of the compositions of matter or atropisomers of the invention of molecules of a non-toxic pharmaceutically acceptable solvent (referred to below as the solvating solvent). Solvates can be prepared by recrystallising the composition of matter or atropisomers of the invention with a solvent or mixture of solvents containing the solvating solvent. Whether or not a solvate has been formed in any given instance can be determined by subjecting crystals of the composition of matter or atropisomer to analysis using well known and standard techniques such as thermogravimetric analysis (TGE), differential scanning calorimetry (DSC) and X-ray powder diffraction (XRPD).

The solvates can be stoichiometric or non-stoichiometric solvates.

Examples of solvates are those formed with any one of more solvents selected from water, alcohols (e.g. methanol, ethanol and isopropyl alcohol), alkyl-alkanoate esters (e.g. ethyl acetate and isopropyl acetate), ethers (particularly cyclic ethers such as 1-4-dioxane and tetrahydrofuran) and monocyclic lactams (e.g. N-methylpyrrolidone).

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

In addition to forming solvates, the compositions of matter, compounds or salts as defined in any one of Embodiments 1.1 to 1.19 may be provided in the form of an anhydrate. The term "anhydrate" as used herein refers to a solid particulate form which does not contain water (and preferably does not contain any other solvents) within its three-dimensional structure (e.g. crystalline form), although particles of the salt or compound may have water molecules attached to an outer surface thereof.

Methods for the Preparation of the Compounds of the Invention

The (+)-L-tartaric acid salt of the invention can be prepared from the atropisomer of the formula (1) by reaction with tartaric acid in a solvent or mixture of solvents and then isolating the tartrate salt from the solvent or mixture of solvents.

In one embodiment, the atropisomer of formula (1) can be dissolved or suspended in one solvent to form a first mixture, and (+)-L-tartaric acid dissolved or suspended in the same or another solvent to form a second mixture, and then the first and second mixtures combined and left (e.g. with stirring) for a period of time to allow salt formation to occur, followed by isolation of the (+)-L-tartaric acid salt.

When the first and second mixtures are combined, it is preferred that the molar amounts of atropisomer of formula (1) and (+)-L-tartaric acid are approximately equivalent; i.e. there is preferably a 1:1 molar ratio between the atropisomer of formula (1) and (+)-L-tartaric acid.

The (+)-L-tartaric acid salt can be isolated from the combined mixture by filtration (when a precipitate is formed) or by evaporation of the solvents.

Thus, when more than one solvent is present in the combined mixture, the different solvents can be selected so as to act as co-solvents or as anti-solvents.

The solvent or mixture of solvents can be selected so that they retain the (+)-L-tartaric acid salt at least partially in solution when heated, but then deposit the salt as a precipitate when the solvent or mixture of solvents is cooled.

The solvent used to form the first mixture (the mixture containing the atropisomer of formula (1)) can be selected from, for example, aliphatic ketones, aliphatic esters of aliphatic acids, non-aromatic cyclic ethers and aliphatic alcohols.

A particular example of an aliphatic ketone is acetone.

Examples of aliphatic esters of aliphatic acids include $C_{2-4}$ alkyl esters of acetic acid, a particular example being isopropylacetate.

Examples of non-aromatic cyclic ethers include dioxane, 2-methyltetrahydrofuran and tetrahydrofuran, a particular example being 2-methyltetrahydrofuran.

Examples of aliphatic alcohols are $C_{2-4}$ aliphatic alcohols, and more particularly $C_{3-4}$ alkanols such as isopropyl alcohol and butanol.

The solvent used to form the second mixture (the mixture containing the (+)-L-tartaric acid) can be selected from, for example, water, non-aromatic cyclic ethers and aliphatic alcohols.

A particular example of an aliphatic alcohol solvent for the second mixture is ethanol.

A particular example of a non-aromatic cyclic ether solvent for the second mixture is tetrahydrofuran (THF).

Another particular example of a solvent for use in forming the second mixture is water.

The (+)-L-tartaric acid salt of the atropisomer of formula (1) can exist in several crystalline forms, notably Pattern A (which is a solvate) and Pattern B (which is an anhydrate). Characterising details for the different crystalline forms are provided elsewhere herein. The different crystalline forms can be prepared by varying the solvents and heating conditions used in the formation of the salts.

In one process for making (+)-L-tartaric acid salt of the atropisomer of formula (1) having Pattern A, a solution of the atropisomer in acetone is mixed with a solution of (+)-L-tartaric acid in ethanol at a temperature in the range from 20° C. to 30° C. (for example approximately 25° C.), the resulting mixture is stirred or otherwise agitated for a length of time (e.g. 12-24 hours) sufficient to allow salt formation to take place, and the salt is then isolated by filtration.

In another process for making (+)-L-tartaric acid salt of the atropisomer of formula (1) having Pattern A, a solution of the atropisomer in isopropyl alcohol is mixed with a solution of (+)-L-tartaric acid in ethanol at a temperature in the range from 35° C. to 45° C. (for example approximately 40° C.), the resulting mixture is cooled to a temperature in the range from 20° C. to 30° C. (for example approximately 25° C.) over a period of approximately 1-3 hours, and the salt is then isolated by filtration.

In another process for making (+)-L-tartaric acid salt of the atropisomer of formula (1) having Pattern A, a solution of the atropisomer in 2-methyltetrahydrofuran is mixed with a solution of (+)-L-tartaric acid in ethanol at a temperature in the range from 20° C. to 30° C. (for example approximately 25° C.), the resulting mixture is stirred or otherwise agitated for a length of time (e.g. 12-24 hours) sufficient to allow salt formation to take place, and the salt is then isolated by filtration.

In one process for making (+)-L-tartaric acid salt of the atropisomer of formula (1) having Pattern B, a solution of the atropisomer in isopropyl acetate at a temperature in the range from 35° C. to 45° C. (for example approximately 40° C.) is mixed with a solution of (+)-L-tartaric acid in ethanol, the resulting mixture is cooled to a temperature in the range from 20° C. to 30° C. (for example approximately 25° C.) over a period of approximately 1-3 hours, and the salt is then isolated by filtration.

In another process for making the (+)-L-tartaric acid salt of the atropisomer of formula (1) having Pattern B, a solution of the atropisomer in isopropyl acetate at a temperature in the range from 35° C. to 45° C. (for example approximately 40° C.) is mixed (either portion-wise or in one single charge) with a solution of (+)-L-tartaric acid in THF and one or more seed crystals of the salt Pattern B are added to give a precipitate, the mixture is cooled to a temperature in the range from 20° C. to 30° C. (for example approximately 25° C.) and stirred or agitated for period of time (e.g. 12 to 24 hours, particularly approximately 20 hours) sufficient to allow ripening of the precipitate to a state in which it can be isolated by filtration.

In another process for (+)-L-tartaric acid salt of the atropisomer of formula (1) having Pattern B, a solution of the atropisomer in butanol at a high temperature in the range from 70° C. to 85° C. (for example approximately 80° C.) is mixed (either portion-wise or in one single charge) with a solution of (+)-L-tartaric acid in water, the resulting mixture is cooled to an intermediate temperature in the range 65° C. to 70° C. before adding one or more seed crystals of the Pattern B salt and cooling the mixture to a low temperature in the range from 3-10° C. over a period of 8 to 15 hours, and thereafter stirring or otherwise agitating the resulting mixture at or near the low temperature for a further period of 2 to 8 hours (e.g. approximately 6 hours) and then filtering off the Pattern B salt thus formed.

The atropisomer of the formula (1) can be prepared by:

(a) separating a mixture (e.g. a racemic mixture) of atropisomers of 4-[5-(4-chlorophenyl)-1-[2-(trifluoromethyl)-phenyl]pyrrol-2-yl]-N-[2 (dimethylamino)-ethyl]benzamide; or (b) reacting an atropisomer of the formula (3):

(3)

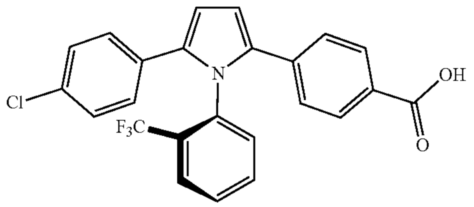

with an amine of the formula $H_2N—(CH_2)—N(CH_3)_2$ under amide forming conditions.

Compounds of the formula (1), (2) and (3) can be prepared by the routes shown in Scheme 1 below.

Scheme 1

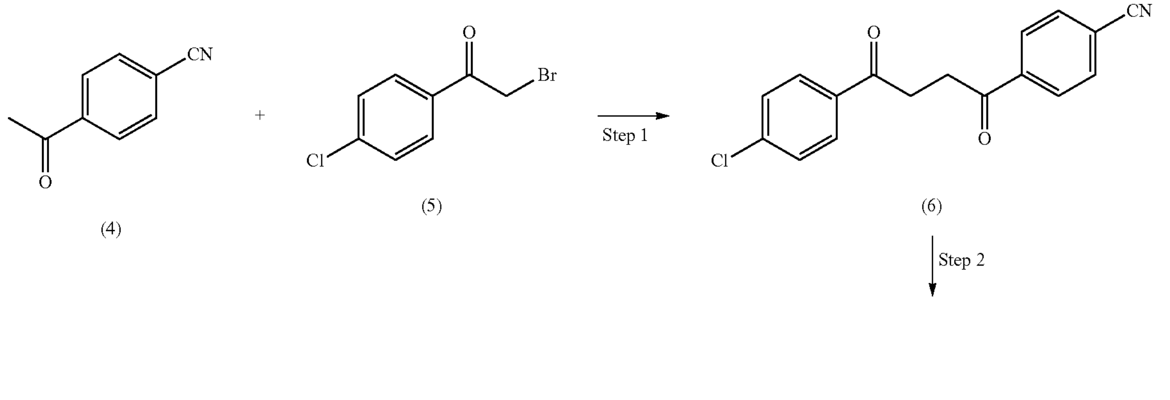

(4) (5) (6)

-continued

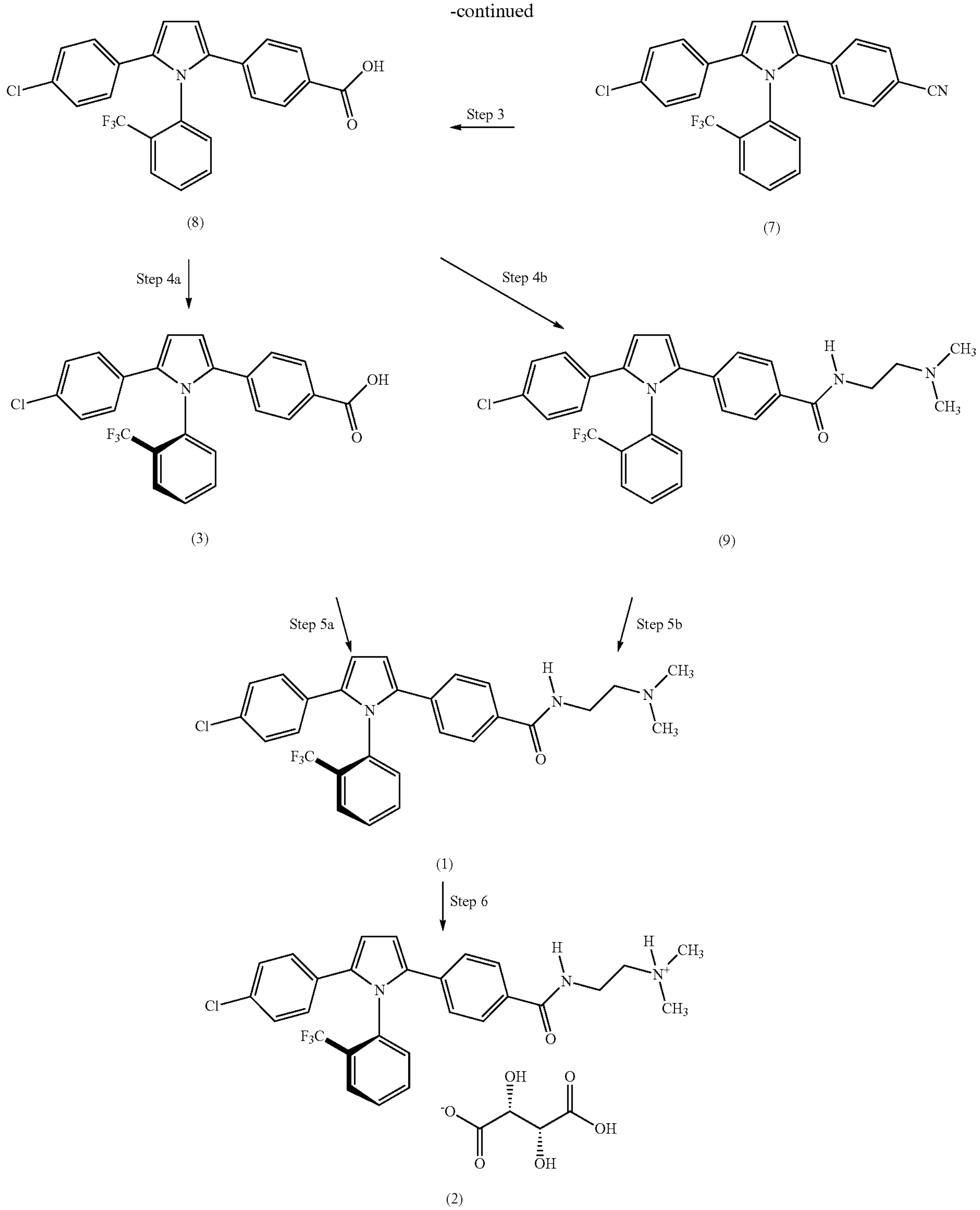

(8) (7) (3) (9) (1) (2)

The starting materials for the synthetic route shown in Scheme 1 are 4-cyano-acetophenone (4) and 4-chlorophenacylbromide (5), both of which are commercially available.

In Step 1, 4-cyano-acetophenone (4) and 4-chlorophenacylbromide (5) are reacted together to give 4-[4-(4-chlorophenyl)-4-oxo-butanoyl]benzonitrile (6). The reaction is typically carried out in the presence of a zinc (II) salt (for example, zinc chloride) in a suitable solvent, for example a mixture of a non-polar (e.g. hydrocarbon) solvent such as benzene or toluene and a tertiary alcohol (for example, t-butanol), in the presence of a tertiary amine such as triethylamine. The reaction may be carried out at room temperature, or near room temperature, for example over a period of 12 to 60 hours.

In Step 2, 4-[4-(4-chlorophenyl)-4-oxo-butanoyl]benzonitrile (6) is reacted with 2-trifluoromethyl aniline to give 4-(5-(4-chlorophenyl)-1-(2-(trifluoromethyl)phenyl)-1H-pyrrol-2-yl)benzonitrile (7). The reaction is typically carried out in the presence of an acid catalyst such as p-toluenesulphonic acid in a suitable high boiling solvent (for example dioxane) at an elevated temperature (for example between 130 and 170° C.) and/or with microwave irradiation. The reaction may be carried out for between 1 and 12 hours, for example between 1 and 6 hours.

In Step 3, 4-(5-(4-chlorophenyl)-1-(2-(trifluoromethyl) phenyl)-1H-pyrrol-2-yl)benzonitrile (7) is subjected to alkaline hydrolysis to give 4-(5-(4-chlorophenyl)-1-(2-(trifluoromethyl)phenyl)-1H-pyrrol-2-yl)benzoic acid (8). The hydrolysis reaction is typically carried out in an aqueous solvent, which may contain an alcohol such as methanol, in the presence of an alkaline metal hydroxide such as sodium hydroxide (typically in an excess amount), and generally with heating, for example to a temperature in the range from 60-80° C. or a period of up to about 20 hours, or more. Once hydrolysis is complete, the acid (8) is typically isolated by cooling and acidifying the reaction mixture.

Following Step 3, one of two possible routes to the atropisomer (1) can be followed. In one variant consisting of Steps 4b and 5b and 6, 4-(5-(4-chlorophenyl)-1-(2-(trifluoromethyl)phenyl)-1H-pyrrol-2-yl)benzoic acid (8) is reacted with N,N-dimethylethylenediamine under amide forming conditions to give a racemic mixture of atropisomers of 4-(5-(4-chlorophenyl)-1-(2-(trifluoromethyl)phenyl)-1H-pyrrol-2-yl)-N-(2-(dimethylamino)ethyl)benzamide (9) which is then resolved into its individual atropisomers by chiral separation to give the atropisomer (1).

In the other variant, racemic 6, 4-(5-(4-chlorophenyl)-1-(2-(trifluoromethyl)phenyl)-1H-pyrrol-2-yl)benzoic acid (8) is subjected to a chiral separation to give the atropisomer (3) which is then reacted with N,N-dimethylethylenediamine under amide forming conditions to give atropisomer (1).

The carboxylic acids (3) and (8) are reacted with N,N-dimethylethylenediamine under amide forming conditions in the presence of an amide coupling reagent. Examples of such amide coupling reagents include carbodiimide-based coupling reagents such as 1,3-dicyclohexylcarbo-diimide (DCC) (Sheehan et al, *J. Amer. Chem Soc.* 1955, 77, 1067) and 1-ethyl-3-(3'-dimethylaminopropyl)-carbodiimide (referred to herein either as EDC or EDCI) (Sheehan et al, *J. Org. Chem.,* 1961, 26, 2525), which are typically used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.,* 103, 708, 2024-2034), uronium-based coupling reagents such as O-(7-azabenzotriazol-1-yl)-N,N,N'N'-tetramethyluronium hexafluorophosphate (HATU), and propanephosphonic acid anhydride (T3P) (see A. Garcia, *Synlett,* 2007, No. 8, pp 1328-1329). Particular amide coupling reagents for use in process steps 5a and 5b are HATU and T3P.

The amide coupling reaction is typically carried out in a non-aqueous, polar, non-protic solvent such as tetrahydrofuran or dimethylformamide, or mixtures thereof at room temperature or thereabouts (e.g. 18-30° C.) in the presence of a non-interfering base, for example a tertiary amine such as triethylamine or N,N-diisopropylethylamine.

Chiral separations of mixtures of atropisomers of carboxylic acid (8) and amide (9) can be carried out using a variety of techniques. For example, chiral chromatography can be used to separate individual atropisomers. The retention times of the atropisomers in the chiral chromatography procedures provide a means of differentiating between and characterising the individual atropisomers whose NMR and MS properties are typically the same.

Chiral chromatography columns that can be used to separate the individual atropisomers comprise an immobilised chiral stationary phase (CSF) which can be, for example, based on a functionalised amylose or cellulose. Examples of such CSF's are amylose and celluloses that have been functionalised with chloro- and/or methyl-substituted phenyl carbamates. Particular examples of chiral columns that may be used to isolate the individual atropisomers of the present invention are the "Chiralpak IG" columns available from Daicel Corporation.

Mobile phases that can typically be used in conjunction with the above chiral columns include mixtures of (A) liquid alkanes such as n-heptane containing a small amount (e.g. up 1% (v/v) and more usually about 0.1% (v/v)) of an alkylamine base such as diethylamine; and (B) alcohols and mixtures thereof such as mixtures of isopropyl alcohol and methanol (e.g. 70:30 IPA:MeOH). For example, the mobile phase can comprise a mixture of A:B in the range of ratios 80:20 to 95:5, for example from approximately 85:15 to approximately 90:10. The mobile phases may be used in isocratic or gradient elution methods but, in one embodiment of the invention, are used in an isocratic elution method.

The atropisomers of the invention may also be resolved by chiral HPLC under supercritical fluid chromatography (SFC) conditions. In supercritical fluid chromatography, the mobile phase comprises a supercritical fluid such as carbon dioxide, often with a co-solvent such as an alcohol or mixture of alcohols, e.g. methanol, ethanol and isopropanol.

The Chiralpak IG columns referred to above may be used in SFC chromatography procedures, using carbon dioxide/methanol/isopropanol mixtures as the mobile phase.

Other chiral column/co-solvent combinations for use in SFC include:

Lux Cellulose 4 (MeOH, EtOH);

Lux Cellulose 2 (MeOH);

Lux Amylose 1 (MeOH, EtOH); and

YMC Amylose-SA (MeOH, EtOH)

The Lux family of chiral columns are available from Phenomenex, Inc.

YMC Amylose-SA columns are available from YMC America, Inc.

The above chiral chromatography methods may be used in particular for the separation of atropisomer (1) from the racemic mixture (9).

As an alternative to chiral chromatography, a chiral acid (e.g. (+)-10-camphorsulphonic acid) can be reacted with the racemic mixture (9) to form a chiral salt as a mixture of diastereoisomers that can be separated by crystallisation to give a salt of atropisomer (1) which can then be converted to the free base of atropisomer (1).

The racemic mixture of atropisomers of carboxylic acid (8) can be resolved by forming a salt with a chiral amine such as (S)-1-(4-methoxyphenyl)-ethylamine to form a mixture of diastereoisomers that can be separated by crystallisation, for example with the assistance of seed crystals of the salt of the chiral amine with atropisomer (1).

Certain aspects of the processes described above represent further embodiments of the invention (Embodiments 2.1 to 2.5). Accordingly, the invention provides:

2.1 A method for the preparation of a compound of the formula (1), which method comprises the reaction of a compound of the formula (3) with N,N-dimethylethylenediamine under amide forming conditions.

2.2 A method according to Embodiment 2.1 wherein the amide forming conditions include the presence of an amide coupling reagent, for example an amide coupling agent as described herein.

2.3 A method according to Embodiment 2.2 wherein the amide coupling reagent is propanephosphonic acid anhydride (T3P).

2.4 A method for the preparation of a compound of the formula (3), which method comprises the chiral separation of the compound of formula (3) from a mixture of atropisomers of formula (8), for example by chiral chromatography or salt formation with a chiral base and resolution of the resulting chiral salt.

2.5 An atropisomer compound having the formula (3), or a salt thereof (for example a metal salt such as an alkaline or alkaline earth metal salt, or a salt with ammonia or an organic amine).

Biological Properties and Therapeutic Uses

The evidence set out in the Examples below indicates that the atropisomer of formula (1) and its tartrate salts as defined herein are inhibitors of the polo box domains of PLK1 and PLK4 kinases but do not inhibit the catalytic domains of PLK1 and PLK4 kinases. Since PBD domains only reside in PLKs, the atropisomer of formula (1) and its tartrate salts should exhibit much greater selectivity (and hence fewer unwanted side effects due to off-target kinase inhibition) than compounds which are ATP-competitive kinase inhibitors. The results obtained from the study described in Example 7F below, where the atropisomer of formula (1) was tested against a panel of ninety seven kinases and showed negligible activity against other kinases, confirms that the atropisomer of formula (1) has a high degree of selectivity for PLK1-PBD and PLK4-PBD over other structurally and functionally similar kinases.

A further advantage of inhibiting the PBD domain rather than the catalytic domain is that this may result in a reduced tendency to induce drug resistance compared to PLK1 inhibitors that inhibit the catalytic domain.

The activity of the atropisomer of formula (1) and its tartrate salts as inhibitors of the PBD domain of PLK1 kinase can be demonstrated using the fluorescence polarization (FP) assay described in Narvaez et al., Cell Chemical Biology, 24, 1017-1028, 2017, see page 1018 and page 1026 (Method Details).

It is believed that atropisomer of formula (1) and its tartrate salts may be effective in exploiting weaknesses in cellular pathways as a result of constitutively activating KRAS mutants and therefore may be useful for the treatment of diseases and conditions mediated by modulation of KRAS.

Mutation of KRAS, resulting from a single nucleotide substitution, has been associated with various forms of cancer. In particular, KRAS mutations are found at high rates in leukaemias, colon cancer, pancreatic cancer and lung cancer.

In addition, it is believed that atropisomer of formula (1) and its tartrate salts may be useful in treating cancers characterised by p53 deficiency or mutation in the TP53 gene. PLK1 is believed to inhibit p53 in cancer cells. Therefore, upon treatment with PLK1 inhibitors, p53 in tumour cells should be activated and hence should induce apoptosis.

The activity of the atropisomer of formula (1) against KRAS mutant and p53 deficient cancers is believed to arise, at least in part, through inhibition of the C-terminal polo box domain (PBD) of PLK1 kinase as described above. KRAS is known to be dependent on interaction with PLK1.

The atropisomer of formula (1) induces mitotic arrest with non-congressed chromosomes, a property which is believed to arise from the PLK1-PBD and PLK4-PBD inhibiting activity of the atropisomer (see Example 7C below).

The atropisomer induces mitotic arrest with a multipolar spindle phenotype, and causes amplification of centrioles, a well described phenotype of PLK4 inhibition (Lei 2018, Cell Death & Disease 9, 1066; Kawakami, PNAS 2018, 115(8) 1913-18). These phenotypes are believed to arise from the PLK4-PBD inhibiting activity of the atropisomer of formula (1).

A primary screen for anticancer activity, which makes use of a cancer cell line (U87MG, human brain (glioblastoma astrocytoma)), is described in Example 7A below. The data obtained demonstrate that the R-atropisomer of formula (1) (atropisomer A-2) is far more active ($IC_{50}$ of 0.22 μM) than the corresponding S-atropisomer (A-1) which has an $IC_{50}$ of 4.6 μM against the U87MG cell line.

The two atropisomers (A-2 and A-1) have also both been tested against a panel of forty eight cancer cells lines and the results are shown in Example 7B below. In every cell line tested, the atropisomer of formula (1) (A-2) was more active than the atropisomer (A-1), in most cases by a factor of at least ten.

The data in Example 7B demonstrate that the atropisomer of formula (1) (A-2) is active against a wide range of different cancer cell lines ranging from solid tumours such as pancreatic cancer, cancers of the large intestine and colorectum, lung cancers, cancers of the brain and nerves, and blood cancers such as lymphoma and leukaemia.

The atropisomer of formula (1) has good oral bioavailability (see Example 7G below) and has good brain exposure when administered orally (Example 7G). Accordingly, the composition of matter or atropisomer of the invention should be useful in treating brain cancers such as gliomas and glioblastomas.

On the basis of the evidence obtained to date, it is believed that the atropisomer of formula (1) will be useful in the treatment of a wide range of cancers (and their benign counterparts), for example the cancers set out in the embodiments below.

Accordingly, in further embodiments (Embodiments 3.1 to 3.25), the invention provides:

3.1. A tartaric acid salt or a composition of matter according to any one of Embodiments 1.1 to 1.19 for use as a PLK1-PBD.

3.2 A tartaric acid salt or a composition of matter according to any one of Embodiments 1.1 to 1.19 for use as a PLK4-PBD inhibitor.

3.3 A tartaric acid salt or a composition of matter according to any one of Embodiments 1.1 to 1.19 for use as a PLK1-PBD and PLK4-PBD inhibitor.

3.4 A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the oesophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukaemias, lymphomas) and premalignant haematological disorders and disorders of borderline malignancy including haematological malignancies and related conditions of lymphoid lineage (for example acute lymphocytic leukaemia [ALL], chronic lymphocytic leukaemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukaemia [AML], chronic myelogenous leukaemia [CML], chronic myelomonocytic leukaemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukaemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

3.4A A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from pancreatic cancers, cancers of the large intestine and colorectum, lung cancers, cancers of the brain and nerves, blood cancers (such as lymphoma and leukaemia), prostate cancers and breast cancers.

3.5 A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from pancreatic cancer, cancers of the large intestine and colorectum, lung cancers, cancers of the brain and nerves, and blood cancers such as lymphoma and leukaemia.

3.6 A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from gliomas and glioblastomas (e.g. glioblastoma multiforme, ependymomas, diffuse intrinsic pontine glioma, IDH1 mutant gliomas).

3.7 A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from rhabdoid tumours; medulloblastoma and other embryonal tumours of the brain; breast, lung, melanoma, gastric, colorectal, pancreatic and ovarian cancer.

3.7A A tartrate salt or a composition of matter according to any one of Embodiments 1.1 to 1.19 for use in treating a cancer, optionally in combination with another therapeutic agent or treatment (e.g. an anticancer agent or therapy), where the cancer is selected from:

(a) tumours of epithelial origin selected from breast cancers, gastrointestinal tract cancers, exocrine pancreas cancers, lung and prostate cancers;
(b) haematological malignancies selected from B-cell lymphomas such as diffuse large B-cell lymphoma [DLBCL], Burkitt's lymphoma, mantle cell lymphoma, multiple myeloma, acute myelogenous leukaemia [AML], chronic myelogenous leukaemia [CML], and myelodysplastic syndrome;
(c) tumours of mesenchymal origin selected from osteosarcomas and rhabdomyosarcomas;
(d) tumours of the central or peripheral nervous system selected from gliomas, glioblastomas and ependymomas; and
(e) paediatric and embryonal tumours selected from medulloblastoma and neuroblastoma.

3.8 A tartrate salt or a composition of matter according to any one of Embodiments 1.1 to 1.19 for use in treating a cancer, optionally in combination with another therapeutic agent or treatment (e.g. an anticancer agent or therapy), wherein the cancer is one in which PLK1 is implicated (e.g. wherein PLK1 is overexpressed).

3.9 A tartrate salt or a composition of matter for use according to Embodiment 3.8 wherein the cancer is as defined in any one of Embodiments 3.4 to 3.7.

3.10 A tartrate salt or a composition of matter according to any one of Embodiments 1.1 to 1.19 for use in treating a cancer, optionally in combination with another therapeutic agent or treatment (e.g. an anticancer agent or therapy), wherein the cancer is one in which PLK4 is implicated (e.g. wherein PLK4 is overexpressed).

3.11 A tartrate salt or a composition of matter for use according to Embodiment 3.10 wherein the cancer is as defined in any one of Embodiments 3.4 to 3.7.

3.12 A tartrate salt or a composition of matter according to any one of Embodiments 1.1 to 1.19 for use in treating a cancer, optionally in combination with another therapeutic agent or treatment (e.g. an anticancer agent or therapy), wherein the cancer is one which is characterised by p53 deficiency or mutation in the TP53 gene.

3.13 A tartrate salt or a composition of matter for use according to Embodiment 3.12 wherein the cancer is as defined in any one of Embodiments 3.4 to 3.7.

3.14 A tartrate salt or a composition of matter according to any one of Embodiments 1.1 to 1.19 for use in treating a cancer wherein the cancer is one which is characterised by the presence of a mutated form of KRAS.

3.15 A tartrate salt or a composition of matter for use according to Embodiment 3.14 wherein the mutated form of KRAS in one having a mutation at an amino acid in the protein selected from glycine 12, glycine 13, glutamine 61, and combinations thereof.

3.16 A tartrate salt or a composition of matter for use according to Embodiment 3.14 or 3.15 wherein the cancer is as defined in any one of Embodiments 3.4 to 3.7.

3.17 A tartrate salt or a composition of matter according to any one of Embodiments 1.1 to 1.19 for use in medicine or therapy, optionally in combination with another therapeutic agent or treatment (e.g. an anticancer agent or therapy).

3.18 A tartrate salt or a composition of matter according to any one of Embodiments 1.1 to 1.19 for use, optionally in combination with another therapeutic agent or treatment (e.g. an anticancer agent or therapy), in preventing or treating disease states and conditions characterised by abnormal expression of KRAS protein.

3.19 A tartrate salt or a composition of matter according to any one of Embodiments 1.1 to 1.19 for use as an anti-cancer agent.

3.20 A method of treating a subject (e.g. a mammalian subject such as human) suffering from a cancer as defined in any one of Embodiments 3.4 to 3.16, which method comprises administering to the subject a therapeutically effective amount of a tartrate salt or a composition of matter according to any one of Embodiments 1.1 to 1.19, optionally in combination with another therapeutic agent or treatment (e.g. an anticancer agent or therapy).

3.21 The use of tartrate salt or a composition of matter according to any one of Embodiments 1.1 to 1.19 for the manufacture of a medicament for a use as defined in any one of Embodiments 3.1 to 3.9.

3.22 A method of inhibiting PLK1-PBD, which method comprises bringing an effective inhibiting amount of a tartaric acid salt or a composition of matter according to any one of Embodiments 1.1 to 1.19 into contact with the PLK1-PBD.

3.23 A method of inhibiting PLK4-PBD, which method comprises bringing an effective inhibiting amount of a tartaric acid salt or a composition of matter according to any one of Embodiments 1.1 to 1.19 into contact with the PLK4-PBD.

3.24 A method of inhibiting PLK1-PBD and PLK4-PBD, which method comprises bringing an effective inhibiting amount of a tartaric acid salt or a composition of matter according to any one of Embodiments 1.1 to 1.19 into contact with the PLK1-PBD and PLK4-PBD.

3.25 A method according to any one of Embodiments 3.22 to 3.24 wherein the effective inhibiting amount of a tartaric acid salt or a composition of matter according to any one of Embodiments 1.1 to 1.19 is brought into contact with the PLK1-PBD and/or PLK4-PBD in vivo, for example in a mammalian subject such as a human subject.

Prior to administration of a tartaric acid salt or a composition of matter according to any one of Embodiments 1.1 to 1.19, a patient may be screened to determine whether a cancer from which the patient is or may be suffering is one which is characterised by elevated levels of PLK1 and/or PLK4 kinase and which would therefore be would be susceptible to treatment with a compound having activity against PLK1 and/or PLK4 kinase.

For example, a biological sample taken from a patient may be analysed to determine whether a cancer, that the patient is or may be suffering from is one which is characterised by a genetic abnormality or abnormal protein expression which leads to up-regulation of PLK1 and/or PLK4 kinase. The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of PLK1 and/or PLK4 kinase. The term diagnosis includes screening. By marker we include genetic markers including, for example, the measurement of DNA composition to identify mutations of PLK1. The term marker also includes markers which are characteristic of up-regulation of PLK1 and/or PLK4, including enzyme activity, enzyme levels, enzyme state (e.g. phosphorylated or not) and mRNA levels of the aforementioned proteins.

Tumours with upregulation of PLK1 and/or PLK4 kinase may be particularly sensitive to PLK1 inhibitors. Tumours may preferentially be screened for upregulation of PLK1 and/or PLK4. Thus, the patient may be subjected to a diagnostic test to detect a marker characteristic of up-regulation of PLK1 and/or PLK4. The diagnostic tests are typically conducted on a biological sample selected from tumour biopsy samples, blood samples (isolation and enrichment of shed tumour cells), stool biopsies, sputum, chromosome analysis, pleural fluid and peritoneal fluid.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively, a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) pre-hybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of up-regulation of PLK1 and/or PLK4 kinase could be applicable in the present case.

Alternatively, or in addition, prior to administration of a tartaric acid salt or a composition of matter according to any one of Embodiments 1.1 to 1.19, a patient may be screened to determine whether a cancer from which the patient is or may be suffering is one which is characterised by mutated KRAS and which would therefore be would be susceptible to treatment with a compound having activity against cancer cells carrying a mutant KRAS.

For example, a biological sample taken from a patient may be analysed to determine whether a cancer, that the patient is or may be suffering from is one which is characterised by a presence of mutant KRAS. Thus, for example, the patient may be subjected to a diagnostic test to detect mutations in at codons 12, 13, 61 or mixtures thereof in the KRAS protein. Commercially available diagnostic tests for mutant KRAS include the Cobas® KRAS Mutation Test from Roche Molecular Systems, Inc and therascreen KRAS RGQ PCR Kit from Qiagen Manchester, Ltd.

Tumours with mutant KRAS may be particularly sensitive to PLK1 and/or PLK4 inhibitors. Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation as described above.

Accordingly, in further embodiments (Embodiments 3.26 to 3.34), the invention provides:

3.26 A tartaric acid salt or a composition of matter according to any one of Embodiments 1.1 to 1.19 for use in the treatment of a cancer in a subject (e.g. a human subject) who has been screened and has been determined as suffering from a cancer which is characterised by elevated levels of PLK1 kinase (e.g. PLK1 overexpression).

3.27 A tartaric acid salt or a composition of matter according to any one of Embodiments 1.1 to 1.19 for use in the treatment of a cancer in a subject (e.g. a human subject) who has been screened and has been determined as suffering from a cancer which is characterised by elevated levels of PLK4 kinase (e.g. PLK4 overexpression).

3.28 A tartaric acid salt or a composition of matter according to any one of Embodiments 1.1 to 1.19 for use in the treatment of a cancer in a subject (e.g. a human subject) who has been screened and has been determined as suffering from a cancer which is characterised by elevated levels of PLK1 kinase and PLK4 kinase (e.g. PLK1 and PLK4 overexpression).

3.29 A tartaric acid salt or a composition of matter according to any one of Embodiments 1.1 to 1.19 for use in the treatment of a cancer in a subject (e.g. a human subject) who has been screened and has been determined as suffering from, or being at risk of suffering from, a disease or condition which would be susceptible to treatment with a compound having activity against KRAS.

3.30 A tartaric acid salt or a composition of matter according to any one of Embodiments 1.1 to 1.19 for use in the treatment of a subject (e.g. a human subject) who has been screened and has been determined as suffering from a cancer which is one which is characterised by mutated KRAS and which would be susceptible to treatment with a compound having activity against cancer cells carrying a mutant KRAS.

3.31 A tartaric acid salt or a composition of matter for use according to any one of Embodiments 3.26 to 3.30 wherein the cancer is a cancer as defined in any one of Embodiments 3.4 to 3.16.

3.32 The use of a tartaric acid salt or a composition of matter according to any one of Embodiments 1.1 to 1.19 for the manufacture of a medicament for a use as defined in any one of Embodiments 3.26 to 3.31.

3.33 A method for the diagnosis and treatment of a disease state or condition (e.g. a cancer, for example a cancer as defined in any one of Embodiments 3.4 to 3.16) characterised by the presence of a mutated form of KRAS which method comprises (i) screening a subject (e.g. a human subject) to determine whether a disease or condition from which the subject is or may be suffering is one which would be susceptible to treatment with a compound having activity against KRAS; and (ii) where it is indicated that the disease or condition from which the subject is thus susceptible, thereafter administering to the subject a therapeutically effective amount of a tartaric acid salt or a composition of matter according to any one of Embodiments 1.1 to 1.19.

3.34 A method for the treatment of a disease state or condition (e.g. a cancer, for example a cancer as defined in any one of Embodiments 3.4 to 3.16) characterised by the presence of a mutated form of KRAS, which method comprises administering a therapeutically effective amount of a tartaric acid salt or a composition of matter according to any one of Embodiments 1.1 to 1.19 to a subject (e.g. a human subject) who has been screened and has been determined as suffering from, or being at risk of suffering from, a disease or condition which would be susceptible to treatment with a compound having activity against KRAS.

Pharmaceutical Formulations

The tartaric acid salt or a composition of matter according to any one of Embodiments 1.1 to 1.19 are typically administered to patients in the form of a pharmaceutical composition. Accordingly, in another Embodiment of the invention (Embodiment 4.1), the invention provides a pharmaceutical composition comprising a tartaric acid salt or a composition of matter according to any one of Embodiments 1.1 to 1.19 and a pharmaceutically acceptable excipient.

In further embodiments, there are provided:

4.2 A pharmaceutical composition according to Embodiment 4.1 which comprises from approximately 1% (w/w) to approximately 95% (w/w) of a tartaric acid salt or a composition of matter according to any one of Embodiments 1.1 to 1.19 and from 99% (w/w) to 5% (w/w) of a pharmaceutically acceptable excipient or combination of excipients and optionally one or more further therapeutically active ingredients.

4.3 A pharmaceutical composition according to Embodiment 4.2 which comprises from approximately 5% (w/w) to approximately 90%,% (w/w) of a composition of tartaric acid salt or a composition of matter according to any one of Embodiments 1.1 to 1.19 and from 95% (w/w) to 10% of a pharmaceutically excipient or combination of excipients and optionally one or more further therapeutically active ingredients.

4.4 A pharmaceutical composition according to Embodiment 3.3 which comprises from approximately 10% (w/w) to approximately 90%,% (w/w) of a tartaric acid salt or a composition of matter according to any one of Embodiments 1.1 to 1.19 and from 90% (w/w) to 10% of a pharmaceutically excipient or combination of excipients.

4.5 A pharmaceutical composition according to Embodiment 4.4 which comprises from approximately 20% (w/w) to approximately 90%,% (w/w) of a tartaric acid salt or a composition of matter according to any one of Embodiments 1.1 to 1.19 and from 80% (w/w) to 10% of a pharmaceutically excipient or combination of excipients.

4.6 A pharmaceutical composition according to Embodiment 3.5 which comprises from approximately 25% (w/w) to approximately 80%,% (w/w) of a tartaric acid salt or a composition of matter according to any one of Embodiments 1.1 to 1.19 and from 75% (w/w) to 20% of a pharmaceutically excipient or combination of excipients.

The pharmaceutical compositions of the invention can be in any form suitable for oral, parenteral, topical, intranasal, intrabronchial, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Accordingly, in further embodiments, the invention provides:

4.7 A pharmaceutical composition according to any one of Embodiments 4.1 to 4.6 which is suitable for oral administration.

4.8 A pharmaceutical composition according to Embodiment 4.7 which is selected from tablets, capsules, caplets, pills, lozenges, syrups, solutions, sprays, powders, granules, elixirs and suspensions, sublingual tablets, sprays, wafers or patches and buccal patches.

4.9 A pharmaceutical composition according to Embodiment 4.8 which is selected from tablets and capsules.

4.10 A pharmaceutical composition according to any one of Embodiments 4.1 to 4.6 which is suitable for parenteral administration.

4.11 A pharmaceutical composition according to Embodiment 4.10 which is formulated for intravenous, intramuscular, intraperitoneal, subcutaneous administration or for direct delivery into a target organ or tissue by injection, infusion or other means of delivery.

4.12 A pharmaceutical composition according to Embodiment 4.11 which is a solution or suspension for injection or infusion.

Pharmaceutical compositions (e.g. as defined in any one of Embodiments 4.1 to 4.12) containing the tartaric acid salt or a composition of matter according to any one of Embodiments 1.1 to 1.19 can be formulated in accordance with known techniques, see for example, Remington's Pharmaceutical Sciences, Mack Publishing Company, Easton, PA, USA.

Thus, tablet compositions (as in Embodiment 4.9) can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations (as in Embodiment 4.9) may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the composition of matter or atropisomer in the stomach or in the ileum or duodenum.

Instead of, or in addition to, a coating, the drug can be presented in a solid matrix comprising a release controlling agent, for example a release delaying agent which may be adapted to selectively release the composition of matter or atropisomer under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration (as in Embodiments 4.10 to 4.12) are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The pharmaceutical compositions will generally be presented in unit dosage form and, as such, will typically contain sufficient compound to provide a desired level of biological activity. For example, a according to any one of Embodiments 4.1 to 4.9), a composition intended for oral administration may contain from 2 milligrams to 200 milligrams of active ingredient, more usually from 10 milligrams to 100 milligrams, for example, 12.5 milligrams, 25 milligrams and 50 milligrams.

Posology

The active compound (tartaric acid salt or a composition of matter according to any one of Embodiments 1.1 to 1.19) will be administered to a patient in need thereof (for example a human or animal patient) in an amount sufficient to achieve the desired therapeutic effect: e.g. an effect as set out in Embodiments 3.1 to 3.34 above.

The tartaric acid salt or a composition of matter according to any one of Embodiments 1.1 to 1.19 will generally be administered to a subject in need of such administration, for example a human or animal patient, preferably a human.

The tartaric acid salt or a composition of matter according to any one of Embodiments 1.1 to 1.19 will typically be administered in amounts that are therapeutically or prophylactically useful and which generally are non-toxic.

However, in certain situations, the benefits of administering compounds of the invention may outweigh the disadvantages of any toxic effects or side effects, in which case it may be considered desirable to administer compounds in amounts that are associated with a degree of toxicity.

In one embodiment, a typical daily dose of the tartaric acid salt or a composition of matter according to any one of Embodiments 1.1 to 1.19 can be in the range from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

In another embodiment, a typical daily dose of the tartaric acid salt or a composition of matter according to any one of Embodiments 1.1 to 1.19 can be in the range from 0.025 milligrams to 50 milligrams per kilogram of body weight, for example up to 30 milligrams per kilogram of bodyweight, and more typically 0.15 milligrams to 50 milligrams per kilogram (e.g. from 0.5 milligrams to 30 milligrams per kilogram) of bodyweight although higher or lower doses may be administered where required.

By way of example, in one embodiment of the invention, an initial starting dose of 12.5 mg may be administered 2 to 3 times a day. The dosage can be increased by 12.5 mg a day every 3 to 5 days until the maximal tolerated and effective dose is reached for the individual as determined by the physician.

In another embodiment of the invention, a once weekly dosing schedule may comprise an initial starting dose of 0.5-1.5 mg/kg (e.g. 1 mg/kg) in week one followed in week two and subsequent weeks by escalating doses (e.g. two or three times the previous dose for up to three, four or five dose escalations) up to a maximum dosage consistent with therapeutic effect and tolerability to the subject. For example, in week one, a starting dose of 1 mg/kg may be administered followed by an increased dose in the second week of 3 mg/kg, 9 mg/kg in the third week and 27 mg/kg in the fourth week.

Ultimately, the quantity of compound administered will be commensurate with the nature of the disease or physiological condition being treated and the therapeutic benefits and the presence or absence of side effects produced by a given dosage regimen, and will be at the discretion of the physician.

Combination Therapy

It is envisaged that the tartaric acid salt or a composition of matter according to any one of Embodiments 1.1 to 1.19 will be useful either as sole chemotherapeutic agents or, more usually, in combination therapy with chemotherapeutic agents or radiation therapy in the prophylaxis or treatment of a range of proliferative disease states or conditions. Examples of such disease states and conditions are set out above.

Particular examples of chemotherapeutic agents or other treatments that may be co-administered with the tartaric acid salt or a composition of matter according to any one of Embodiments 1.1 to 1.19 include:

- Topoisomerase I inhibitors (e.g. irinotecan)
- Antimetabolites: (e.g. cytarabine or gemcitabine)
- Tubulin targeting agents (e.g. paclitaxel)
- DNA binder and topoisomerase II inhibitors
- EGFR inhibitors (e.g. gefitinib or afatinib)
- mTOR inhibitors (e.g. everolimus)
- PI3K pathway inhibitors (e.g. PI3K, PDK1)
- Akt inhibitors
- Alkylating Agents (e.g. temozolomide)
- Monoclonal Antibodies.
- Anti-Hormones
- Signal Transduction inhibitors
- Proteasome Inhibitors
- DNA methyl transferase inhibitors
- Cytokines and retinoids
- Hypoxia triggered DNA damaging agents (e.g. tirapazamine)
- Aromatase inhibitors
- Anti Her2 antibodies, (see for example http://www.wipo.int/pctdb/en/wo.jsp?wo=2007056118)
- Anti cd20 antibodies (e.g. rituximab)
- Inhibitors of angiogenesis
- HDAC inhibitors
- MEK inhibitors
- B-Raf inhibitors
- ERK inhibitors
- HER2 small molecule inhibitors (e.g. lapatinib or afatinib)
- Bcr-Abl tyrosine-kinase inhibitors (e.g. imatinib)
- CDK4/6 inhibitor (e.g. palbociclib)
- Mps1/TTK inhibitors
- Aurora B inhibitors
- FLT3 kinase inhibitors
- IDH1 or IDH2 inhibitors
- BRD4 inhibitors
- temozolomide
- Inhibitors of immune checkpoint blockade signalling components including PD1, PDL-1 and CTLA4;
- KRAS blocking drugs, including those against specific mutations such as G12C (e.g. sotorasib);
- Bcl2 inhibitors (e.g. venetoclax, sabutoclax or obatoclax); and
- radiotherapy.

Preferred examples of chemotherapeutic agents or other treatments that may be co-administered with the tartaric acid salt or a composition of matter according to any one of Embodiments 1.1 to 1.19 may be selected from:

- Topoisomerase I inhibitors (e.g. irinotecan)
- Antimetabolites: (e.g. cytarabine or gemcitabine)
- Tubulin targeting agents (e.g. paclitaxel)
- EGFR inhibitors (e.g. gefitinib or afatinib)

mTOR inhibitors (e.g. everolimus)

Alkylating Agents (e.g. temozolomide)

Anti cd20 antibodies (e.g. rituximab)

Inhibitors of immune checkpoint blockade signalling components including

PD1, PDL-1 and CTLA4;

KRAS blocking drugs, including those against specific mutations such as G12C (e.g. sotorasib);

Bcl2 inhibitors (e.g. venetoclax, sabutoclax or obatoclax); and radiotherapy.

Accordingly, in further embodiments, the invention provides:

5.1 A pharmaceutical combination comprising a tartaric acid salt or a composition of matter according to any one of Embodiments 1.1 to 1.19 and another therapeutically active agent.

5.2 A pharmaceutical combination according to Embodiment 5.1 wherein the said another therapeutic agent is selected from the particular and preferred chemotherapeutic agents listed above.

5.3 A pharmaceutical combination according to Embodiment 5.1 wherein the said another therapeutic agent is an anticancer agent.

5.4 A pharmaceutical combination according to any one of Embodiments 5.1 to 5.3 wherein the tartaric acid salt or a composition of matter according to any one of Embodiments 1.1 to 1.19 and the said another therapeutically active agent are presented in a single pharmaceutical composition or patient pack.

5.5 A pharmaceutical composition comprising a tartaric acid salt or a composition of matter according to any one of Embodiments 1.1 to 1.19, another therapeutically active agent and at least one pharmaceutically acceptable excipient.

5.6 A method of treatment of a subject suffering from a cancer which method comprises the administration to the subject of a therapeutically effective amount of a pharmaceutical combination according to any one of Embodiments 5.1 to 5.5.

EXAMPLES

Figure 1:
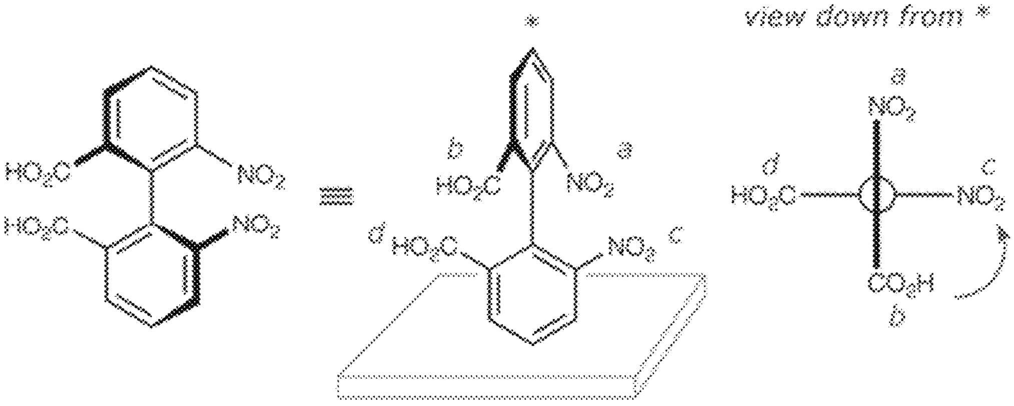
FIG. 1 is a schematic diagram illustrating the R/S classification system for atropisomers.

The invention will now be illustrated, but not limited, by reference to the specific embodiments described in the following examples.

Proton magnetic resonance (1H NMR) spectra were recorded on a Bruker 400 instrument operating at 400 MHz, in dimethylsulfoxide-d6 (DMSO-d6) or methanol-d4 (MeOH-d4) (as indicated) at 27° C., unless otherwise stated and are reported as follows: chemical shift b/ppm (multiplicity where s=singlet, d=doublet, dd=double doublet, dt—double triplet, t=triplet, q=quartet, m=multiplet, br=broad, number of protons). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^{35}Cl$; $^{79}Br$ etc.)

LCMS Conditions

The LCMS data given in the following examples were obtained using one of the methods described below.

LCMS Method 1

LCMS was carried out on UPLC AQUITY with PDA photodiode array detector and QDa mass detector. The column used was a C18, 2.1×50 mm, 1.9 μm. The column flow was 1.2 mL/min and the mobile phase used was: (A) 0.1% Formic acid in MilliQ water (pH=2.70) (B) 0.1% Formic acid in water:acetonitrile (10:90), the injection volume was between 4 and 7 μL. The sample was prepared in methanol:acetonitrile to achieve an approximate concentration of 250 ppm.

The following gradient was used for the elution:

| Time (min) | Flow (ml/min) | % A | % B |
|---|---|---|---|
| 0.00 | 0.8 | 97 | 3 |
| 0.20 | 0.8 | 97 | 3 |
| 2.70 | 0.8 | 2 | 98 |
| 3.00 | 1.0 | 00 | 100 |
| 3.50 | 1.0 | 00 | 100 |
| 3.51 | 0.8 | 97 | 3 |
| 4.00 | 0.8 | 97 | 3 |

Mass Parameters

Probe: ESI capillary

Source Temperature: 120° C.

Probe Temperature: 600° C.

Capillary Voltage: 0.8 KV (+Ve and −Ve)

Cone Voltage: 10 & 30 V

Mode of Ionization: Positive and negative

HPLC Analysis

The HPLC data reported were obtained using the following method.

HPLC Method 1

HPLC analysis was carried out on an Agilent Technologies 1100/1200 series HPLC system. The column used was an ACE 3 C18; 150×4.6 mm, 3.0 μm particle size (Ex: Hichrom, Part number: ACE-111-1546). The flow rate was 1.0 mL/min. Mobile phase A was water:trifluoroacetic acid (100:0.1%) and mobile phase B was acetonitrile:trifluoroacetic acid (100:0.1%). The injection volume was 5 μL and the following gradient was used:

| Time (mins) | % A | % B |
|---|---|---|
| 0 | 80 | 20 |
| 35 | 5 | 95 |
| 39.5 | 5 | 95 |
| 40 | 80 | 20 |

Chiral HPLC Analysis

The chiral HPLC data reported were obtained using one of the methods described below.

Chiral HPLC Method 1

Chiral HPLC was analysis was carried out on an Agilent Technologies 1200 series HPLC system. The column used was a CHIRAL PAK IG, 250×4.6 mm, 5 μm. The column flow rate was 1.0 mL/min and the mobile phase was: (A) 0.1% v/v DEA in n-heptane and (B) IPA:MeOH (70:30). The injection volume was 25 μL. Samples were prepared in IPA:MeOH to achieve an approximate concentration of 250 ppm and with the following isocratic method:

| Time | Flow | % A | % B |
|---|---|---|---|
| 0.01 | 1.0 mL/min | 90 | 10 |
| 45 | 1.0 mL/min | 90 | 10 |

Chiral HPLC Method 3

Chiral HPLC was carried out on an Agilent Technologies 1200 series HPLC system. The column used was a CHIRAL PAK IG, 250×4.6 mm, 5 μm. The column flow rate was 1.0 mL/min and the mobile phase was: (A) 0.1% v/v DEA in n-heptane and (B) IPA: MEOH (70:30). The injection volume was 10 μL. Samples were prepared in IPA:MeCN to achieve an approximate concentration of 250 ppm and with the following isocratic method:

| Time | Flow | % A | % B |
|---|---|---|---|
| 0.01 | 1.0 mL/min | 85 | 15 |
| 25 | 1.0 mL/min | 85 | 15 |

Chiral HPLC Method 4

Identical conditions to chiral method 3 except using the following isocratic method:

| Time | Flow | % A | % B |
|---|---|---|---|
| 0.01 | 1.0 mL/min | 70 | 30 |
| 25 | 1.0 mL/min | 70 | 30 |

Chiral HPLC Method 5

Identical conditions to chiral method 3 except using the following isocratic method:

| Time | Flow | % A | % B |
|---|---|---|---|
| 0.01 | 1.0 mL/min | 90 | 10 |
| 25 | 1.0 mL/min | 90 | 10 |

Chiral HPLC Method 6

Chiral HPLC was analysis was carried out on an Agilent Technologies 1100/1200 series HPLC system. The column used was a CHIRALPAK AD-H; 250×4.6 mm, 5.0 μm. The column flow rate was 1.0 mL/min and the mobile phase was: Hexane:EtOH:TFA (90:10:0.1%). The injection volume was 5 μL. Samples were prepared in 100% EtOH to achieve an approximate concentration of 0.5 mg/mL.

Chiral HPLC Method 7

Chiral HPLC was analysis was carried out on an Agilent Technologies 1100/1200 series HPLC system. The column used was a CHIRALPAK IA; 250×4.6 mm, 5.0 μm. The column flow rate was 1.0 mL/min and the mobile phase was: Hexane:EtOH:Ethanolamine (90:10:0.1%). The injection volume was 5 μL. Samples were prepared in 100% EtOH to achieve an approximate concentration of 0.5 mg/mL.

Preparative Chiral HPLC Methods:

The atropisomers were isolated using one of the following preparative chiral HPLC methods.

Preparative Chiral HPLC Method 1

Preparative chiral HPLC was carried out using a CHIRALPAK IG SFC, 21×250 mm, 5 μm column, eluting with (A) 0.1% DEA in heptane and (B) IPA as mobile phase, with the flow rate of 30 mL/min and the following isocratic system:

| Time (min) | % A | % B |
|---|---|---|
| 0.01 | 94 | 6 |
| 50.00 | 94 | 6 |

Preparative Chiral HPLC Method 2

Preparative chiral HPLC was carried out using a CHIRALPAK IG SFC column, 21×250 mm, 5 μm eluting with (A) 0.1% DEA in heptane and (B) IPA:MeOH (90:10) as mobile phase and a flow rate of 22 mL/min and with the following isocratic system was used for the elution:

| Time (min) | % A | % B |
|---|---|---|
| 0.01 | 93 | 7 |
| 35.00 | 93 | 7 |

Example 1

(R)-4-[5-(4-Chlorophenyl)-1-[2-(trifluoromethyl)-phenyl]pyrrol-2-yl]-N-[2-(dimethylamino)-ethyl] benzamide (1)

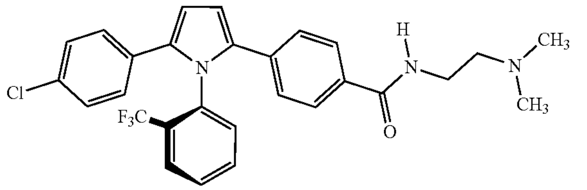

The title compound was prepared by following Steps 1, 2, 3, 4b and 5b of the synthetic routes shown in Scheme 1 above.

Step 1: 4-[4-(4-chlorophenyl)-4-oxo-butanoyl]benzonitrile (6)

(6)

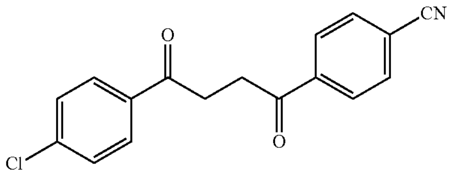

Zinc chloride (30.5 g, 223 mmol) was heated to melting under vacuum then cooled to room temperature. Toluene (100 mL), tert-butanol (16.5 mL, 172 mmol) and triethylamine (24 mL, 172 mmol) were added and the mixture was stirred at room temperature for 2 hours under a nitrogen atmosphere at which point the zinc chloride had fully dissolved. 4-Cyanoacetophenone (25 g, 172 mmol) and 4-chlorophenacylbromide (40.2 g, 172 mmol) were added and the reaction mixture was stirred at room temperature for 48 hours. The reaction mixture was then diluted with ethyl acetate (300 mL) and washed with water (5×100 mL). The combined organic extracts were dried ($Na_2SO_4$) and evaporated under reduced pressure. The resulting residue was purified by trituration using methyl tert-butyl ether (400 mL) to afford the title compound (30 g, 101 mmol, 59%).

Step 2: 4-(5-(4-chlorophenyl)-1-(2-(trifluoromethyl)phenyl)-1H-pyrrol-2-yl)benzonitrile (7)

(7)

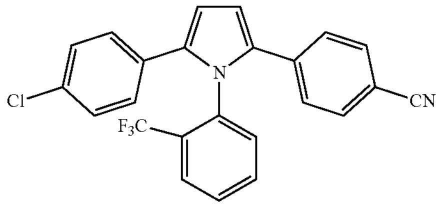

A stirred solution of 4-(4-(4-chlorophenyl)-4-oxobutanoyl)benzonitrile (30 g, 101 mmol), 2-trifluoromethyl aniline (48.79 g, 303 mmol) and p-toluenesulfonic acid (1.92 g, 10.099 mmol) in dioxane (300 mL) was heated at 150° C. for 16 hours. The reaction mixture was concentrated under reduced pressure and the resulting residue was purified by column chromatography on silica gel (60-120 mesh) using 8% ethyl acetate/hexane as the eluent to afford the title compound (30 g, 71 mmol, 70%).

Step 3: 4-(5-(4-chlorophenyl)-1-(2-(trifluoromethyl)phenyl)-1H-pyrrol-2-yl)benzoic acid (8)

(8)

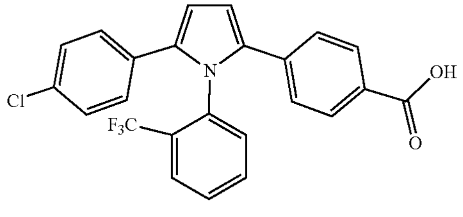

To a solution of 4-(5-(4-chlorophenyl)-1-(2-(trifluoromethyl)phenyl)-1H-pyrrol-2-yl)benzonitrile (2 g, 4.739 mmol) in methanol (20 mL) was added sodium hydroxide (1.89 g, 47 mmol) in water (10 mL) and the resulting mixture was stirred at 90° C. for 24 hours. The mixture was concentrated under reduced pressure and the resulting residue was purified by trituration by using diethyl ether (10 mL) to afford the title compound (1.8 g, 4.1 mmol, 86%).

Step 4b: 4-(5-(4-chlorophenyl)-1-(2-(trifluoromethyl)phenyl)-1H-pyrrol-2-yl)-N-(2-(dimethylamino)ethyl)benzamide (9)

(9)

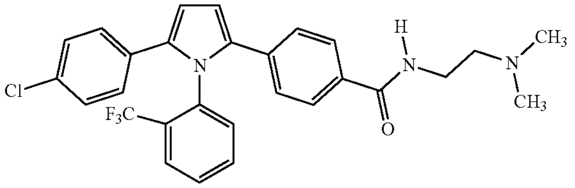

To a stirred solution of 4-(5-(4-chlorophenyl)-1-(2-(trifluoromethyl)phenyl)-1H-pyrrol-2-yl)benzoic acid (1.8 g, 4.0 mmol) in dimethylformamide (12 mL) was added N,N-diisopropylethylamine (2.13 mL, 22 mmol) followed by (1-[bis(dimethylamino)methylene]-1H-1,2,3-triazolo[4,5-b] pyridinium-3-oxide hexafluorophosphate) (HATU) (4.65 g, 12 mmol). The reaction mixture was stirred at room temperature for 30 minutes followed by the addition of N,N'-dimethylethylenediamine (1.08 g, 12 mmol) dropwise and stirring was continued at room temperature for 4 hours. The mixture was then poured into ice-cold water (150 mL) and extracted with ethyl acetate (3×100 mL). The combined organic layers were dried ($Na_2SO_4$) and concentrated under reduced pressure. The resulting residue was purified by column chromatography on neutral alumina eluting with 6% methanol/dichloromethane to afford the title compound (1.2 g, 2.3 mmol, 57%) as a mixture of atropisomers.

Step 5b: Separation of Atropisomers

The atropisomers of 4-[5-(4-chlorophenyl)-1-[2-(trifluoromethyl)phenyl]pyrrol-2-yl]-N-[2-(dimethylamino)ethyl] benzamide were resolved by chiral HPLC using preparative Chiral HPLC Method 1.

Two peaks were isolated:

Peak 1: Example A-1, 4-[5-(4-chlorophenyl)-1-[2-(trifluoromethyl)phenyl]pyrrol-2-yl]-N-[2 (dimethylamino) ethyl]benzamide-atropisomer1 (0.3 g, 0.58 mmol, 38%, >99% ee), and:

Peak 2: Example A-2, 4-[5-(4-chlorophenyl)-1-[2-(trifluoromethyl)phenyl]pyrrol-2-yl]-N-[2 (dimethylamino) ethyl]benzamide-atropisomer2 (0.31 g, 0.606 mmol, 39%, 98% ee).

The compounds can also be isolated as their hydrochloride salts.

Example 2

Further purification and characterisation of the atropisomers

Atropisomer A-1: (S)-4-[5-(4-chlorophenyl)-1-[2-(trifluoromethyl)phenyl]pyrrol-2-yl]-N-[2 (dimethyl-amino)ethyl]benzamide hydrochloride salt Peak 1 (0.31 g, 0.606 mmol) from Example 1, Step 5b was further purified by stirring in HPLC grade water (30 mL) followed by sonication for 10 min and extraction with ethyl acetate (3×30 mL). The combined organic layers were dried ($Na_2SO_4$), filtered and concentrated under reduced pressure followed by lyophilisation to afford an amorphous solid (0.290 g, 0.567 mmol, 94%) which was dissolved in dichloromethane (7.12 mL). The resulting solution was cooled to 0° C. and 4N HCl in dioxane (1.42 mL) was added. The reaction mixture was stirred at room temperature for 3 hours. The mixture was concentrated and dried under high vacuum. Purification by trituration using diethyl ether (10 mL) and lyophilisation afforded the title compound (0.3 g, 0.56 mmol, 98%) as an off-white solid.

$^1$H NMR (DMSO-$d_6$) δ 10.03, (brs, 1H), 8.62 (s, 1H), 7.81-7.68 (m, 6H), 7.25 (d, J=8.4 Hz, 2H), 7.10-7.03 (m, 4H), 6.67-6.58 (m, 2H), 3.56-3.54 (m, 2H), 3.20-3.18 (m, 2H), 2.76 (s, 6H). LCMS (Method 1)—RT 2.54, MH+512.4

Atropisomer A-2: (R)-4-[5-(4-chlorophenyl)-1-[2-(trifluoromethyl)phenyl]pyrrol-2-yl]-N-[2 (dimethyl-amino)ethyl]benzamide hydrochloride salt The hydrochloride salt of atropisomer A-2 was prepared using the same method as was used for atropisomer A-1 starting from peak 2 to afford the title compound (0.31 g, 0.56 mmol, 99%), an off-white solid.

$^1$H NMR (DMSO-$d_6$) δ 9.91 (brs, 1H), 8.69 (s, 1H), 7.81-7.68 (m, 6H), 7.25 (d, J=8.0 Hz, 2H), 7.10-7.03 (m, 4H), 6.67-6.58 (m, 2H), 3.56-3.54 (m, 2H), 3.20-3.18 (m, 2H), 2.77 (s, 6H). LCMS (Method 1)—RT 2.56, MH+512.4

Single crystal X-ray crystallographic analysis of atropisomer A-2 (see Example 3 below) indicated that atropisomer A-2 is the R-isomer (Compound (1)) and hence atropisomer A-1 must be the S-isomer.

Chiral Analysis

Analysis of the chiral properties of the Atropisomers A-1 and A-2 was carried out by measuring their optical rotations and their retention times obtained by chiral HPLC.

Specific Optical Rotation Protocol:

Instrumentation: Optical Activity AA-10 Automatic Polarimeter

Wavelength: 589 nm

Temperature: 23° C.

Pathlength of cell: 1 dm

Solvent: Chloroform (Fisher, HPLC grade)

Concentration: 1.0 g/100 mL

Sampling Technique:

The instrument was switched on and allowed to stabilize for 30 min before calibration was checked using an Optical Activity Quartz Control Plate (S/N 00049). The angular rotation at 23° C. using sodium yellow D line was measured at 34.16° (after firstly zeroing the instrument without any sample tube). The sample tube quality was checked by zeroing the instrument, then filling the sample tube with chloroform and checking the instrument was still reading 0.00 (+/−0.02). The instrument was zeroed with the chloroform blank in place. The sample was dissolved in $CHCl_3$ (2 mg in 2 mL), filtered and 2 mL was pipetted into the cell to measure α.

The specific optical rotation was calculated from the following equation: $[\alpha]T\lambda=(\alpha\times100)/(cl)$

| Atropisomer | Chiral HPLC RT (min) | Chiral HPLC Method | Specific Optical Rotation |
|---|---|---|---|
| A-1 (S-atropisomer) | 17.063 | 1 | +12.39° |
| A-2 (R-atropisomer) | 20.553 | 1 | −11.76° |

Atropisomer Classification

Stability studies were carried out on the isolated atropisomers A-1 and A-2

To assess the interconversion of atropisomer A-1 and atropisomer A-2, chiral stability was monitored at 40° C. and 80° C. As shown by the results set out below, no interconversion was observed on heating for 10 days at either temperature.

| | % ee of sample @ 40° C. | | % ee sample @ 80° C. | |
|---|---|---|---|---|
| Time/ h | A-1 | A-2 | A-1 | A-2 |
| 0 | 100 | 97.20 | 100 | 97.20 |
| 24 | 100 | 97.34 | 100 | 95.62 |
| 48 | 100 | 97.30 | nd | nd |
| 72 | 100 | 97.24 | nd | nd |
| 96 | 100 | 97.14 | 100 | 96.62 |
| 10 days | 100 | 97.46 | 100 | 97.12 |

Protocol:

1. 2×1 mg of pure atropisomer was dissolved in 1 mL of ethanol in a sealed-dram vial.

2. One set of vials was heated at 40° C. and another set at 80° C.
3. At specified time-points a 20 μL aliquot from each stock solution (1 mL) was taken and quenched into a HPLC vial containing a 80 μL solution of hexane:ethanol; 80:20 to afford a final concentration of 200 ppm and the sample was analysed by chiral HPLC
4. Analysis was carried out at the following time-points: 0 h, 24 h, 48 h, 72 h, 96 h and 240 h for the samples kept at 40° C. and 24 h, 96 h and 240 h for the samples kept at 80° C. using chiral HPLC method 5

The stabilities of the isolated atropisomers A-1 and A-2 confirmed that they are Class 3 atropisomers (LaPlante et al., J. Med. Chem., 54:7005-7022 (2011))).

Example 3

X-Ray Crystallographic Analysis of Atropisomer A-2

Atropisomer A-2 free base was prepared, and a single crystal was subjected to X-ray crystallographic studies as described below.

Experimental:

Single non-defined morphology crystals of atropisomer A-2 were obtained by recrystallisation from methyl isobutyl ketone (MIBK). A suitable crystal 0.19×0.13×0.04 $mm^3$ was selected and, using MiTiGen MicroMount, mounted on a Rigaku XtaLAB Syngery-S diffractometer equipped with a HyPix-6000HE detector. The crystal was kept at a steady T=123(2) K during data collection.

Data were generated using CuKα radiation. The maximum resolution that was achieved was θ=74.263° (0.80 Å). Data reduction, scaling and absorption corrections were performed. The final completeness was 100.00% out to 74.263° in O. The absorption coefficient of the compound was determined as being 1.761 $mm^{-1}$ at the wavelength (λ=1.542 Å).

The data were collected and processed using CrysAlisPro software and the structure was solved with the SheIXT (Sheldrick, 2015) structure solution program using the Intrinsic Phasing solution method and by using Olex2 (Dolomanov et al., 2009) as the graphical interface. The model was refined with version 2018/3 of SheIXL-2018/3 (Sheldrick, 2018) using Least Squares minimisation.

The crystal structure was found to be monoclinic and was assigned the space group P21 (#4).

All non-hydrogen atoms were refined anisotropically. Hydrogen atom positions were calculated geometrically and refined using the riding model.

REFERENCES

O. V. Dolomanov and L. J. Bourhis and R. J. Gildea and J. A. K. Howard and H. Puschmann, Olex2: A complete structure solution, refinement and analysis program, J. Appl. Cryst., (2009), 42, 339-341.

Sheldrick, G. M., Crystal structure refinement with SheIXL, Acta Cryst., (2015), C71, 3-8.

Sheldrick, G. M., SheIXT-Integrated space-group and crystal-structure determination, Acta Cryst., (2015), A71, 3-8.

The results of the studies are set out below in Tables 1-7.

TABLE 1

| Data for crystal of Atropisomer A-2 Free Base | |
|---|---|
| Formula | $C_{28}H_{25}ClF_3N_3O$ |
| $D_{calc.}$/g $cm^{-3}$ | 1.350 |

TABLE 1-continued

| Data for crystal of Atropisomer A-2 Free Base | |
|---|---|
| m/$mm^{-1}$ | 1.761 |
| Formula Weight | 511.96 |
| Colour | n/a |
| Shape | n/a |
| Size/mm3 | 0.19 × 0.13 × 0.04 |
| T/K | 123 (2) |
| Crystal System | monoclinic |
| Flack Parameter | −0.03 (2) |
| Hooft Parameter | 0.020 (6) |
| Space Group | P21 |
| a/Å | 10.1964 (3) |
| b/Å | 8.6349 (4) |
| c/Å | 14.3398 (6) |
| a/° | 90 |
| b/° | 93.955 (4) |
| g/° | 90 |
| V/$Å^3$ | 1259.53 (9) |
| Z | 2 |
| Z' | 1 |
| Wavelength/Å | 1.54184 |
| Radiation type | $CuK_a$ |
| $Q_{min}$/° | 3.089 |
| $Q_{max}$/° | 74.263 |
| Measured Refl. | 17242 |
| Independent Refl. | 4929 |
| Reflections with I > 2(I) | 4544 |
| Rint | 0.0357 (3.57%) |
| Parameters | 327 |
| Restraints | 1 |
| Largest Peak | 0.381 |
| Deepest Hole | −0.188 |
| GooF | 1.032 |
| $wR_2$ (all data) | 0.1228 |
| $WR_2$ | 0.1174 |
| $R_1$ (all data) | 0.0474 |
| $R_1$ | 0.0433 |
| Reflections | d min (Cu) = 0.80; I/σ = 35.2; Complete 10% (IUCR) = 99% |
| Refinement | Shift = 0.000; Max. Peak = 0.4; Min peak = −0.2 |

TABLE 2

Fractional Atomic Coordinates (×$10^4$) and Equivalent Isotropic Displacement Parameters ($Å^2$ ×$10^3$) for Atropisomer A-2. $U_{eq}$ is defined as 1/3 of the trace of the orthogonalised $U_{ij}$.

| Atom | x | y | z | $U_{eq}$ |
|---|---|---|---|---|
| Cl36 | 7764.8(9) | 10484.3(12) | 2175.1(6) | 58.8(3) |
| F19 | 8576.0(19) | 5604(3) | 7787.5(13) | 47.5(5) |
| F20 | 9300.0(18) | 6815(3) | 6631.6(14) | 56.0(6) |
| F21 | 8706(2) | 8065(3) | 7827.5(18) | 61.5(6) |
| O35 | 6134(2) | −381(3) | 9646.9(18) | 44.1(5) |
| N29 | 4745(2) | 1641(3) | 9788.3(18) | 36.4(5) |
| N32 | 1997(2) | 656(3) | 9424.4(17) | 36.5(5) |
| N7 | 7412(2) | 4971(3) | 5673.0(16) | 32.3(5) |
| C28 | 5700(3) | 889(3) | 9377(2) | 34.9(6) |
| C12 | 6589(3) | 6128(3) | 6040(2) | 31.4(6) |
| C11 | 7755(3) | 3554(4) | 6084(2) | 35.0(6) |
| C9 | 8822(3) | 3840(4) | 4773(2) | 39.7(7) |
| C17 | 7018(3) | 7016(4) | 6817(2) | 34.2(6) |
| C13 | 5360(3) | 6390(4) | 5597(2) | 36.7(6) |
| C26 | 7530(3) | 1442(4) | 8352(2) | 36.1(6) |
| C2 | 7880(3) | 8040(4) | 4542(2) | 37.9(6) |
| C8 | 8077(3) | 5149(4) | 4861(2) | 35.3(6) |
| C1 | 7975(3) | 6504(4) | 4243(2) | 36.4(6) |
| C24 | 5413(3) | 2530(4) | 7922(2) | 35.7(6) |
| C18 | 8397(3) | 6877(4) | 7264(2) | 37.7(6) |
| C22 | 7203(3) | 2948(4) | 6928(2) | 34.9(6) |
| C3 | 7834(3) | 9267(4) | 3916(2) | 41.2(7) |
| C25 | 6226(3) | 1670(3) | 8545(2) | 33.5(6) |
| C31 | 2911(3) | −109(4) | 10106(2) | 38.8(7) |
| C6 | 8027(3) | 6246(4) | 3276(2) | 40.6(7) |
| C23 | 5889(3) | 3149(4) | 7118(2) | 36.8(6) |

TABLE 2-continued

Fractional Atomic Coordinates (×10^4) and Equivalent Isotropic Displacement Parameters ($Å^2$ ×$10^3$) for Atropisomer A-2. $U_{eq}$ is defined as 1/3 of the trace of the orthogonalised $U_{ij}$.

| Atom | x | y | z | $U_{eq}$ |
|---|---|---|---|---|
| C30 | 4005(3) | 939(4) | 10513(2) | 38.6(7) |
| C27 | 8013(3) | 2085(4) | 7566(2) | 36.1(6) |
| C10 | 8632(3) | 2863(4) | 5533(2) | 39.2(7) |
| C16 | 6185(3) | 8123(4) | 7156(2) | 42.2(7) |
| C15 | 4949(4) | 8367(4) | 6710(3) | 46.4(8) |
| C4 | 7882(3) | 8953(5) | 2972(2) | 42.5(7) |
| C14 | 4541(3) | 7517(4) | 5926(3) | 41.6(7) |
| C5 | 7986(3) | 7463(5) | 2643(2) | 43.4(8) |
| C34 | 1206(3) | 1831(5) | 9855(2) | 47.0(8) |
| C33 | 1136(4) | −484(5) | 8950(3) | 49.5(8) |

TABLE 3

Anisotropic Displacement Parameters (×10^4) SOL_686_i42-5 Hz. The anisotropic displacement factor exponent takes the form: $-2\pi^2[h^2a^{*2} \times U_{11} + \ldots + 2hka^* \times b^* \times U_{12}]$

| Atom | $U_{11}$ | $U_{22}$ | $U_{33}$ | $U_{23}$ | $U_{13}$ | $U_{12}$ |
|---|---|---|---|---|---|---|
| Cl36 | 57.6(5) | 68.4(6) | 49.6(4) | 19.0(4) | −1.6(4) | −1.6(4) |
| F19 | 46.7(10) | 46.1(11) | 48.0(10) | 7.6(9) | −10.0(8) | −6.8(9) |
| F20 | 31.1(9) | 89.9(17) | 46.4(10) | 9.7(11) | −1.4(7) | −10.4(10) |
| F21 | 62.3(13) | 47.5(12) | 70.7(14) | −13.8(11) | −24.9(11) | −5.3(11) |
| O35 | 43.0(12) | 35.0(11) | 54.6(13) | 7.3(10) | 4.8(10) | 3.5(10) |
| N29 | 33.7(12) | 32.3(12) | 43.3(13) | 2.5(11) | 2.4(10) | −1.1(10) |
| N32 | 33.3(12) | 36.4(13) | 39.4(12) | −0.1(11) | −0.2(10) | −1.4(11) |
| N7 | 25.9(11) | 36.3(13) | 34.6(11) | −1.4(10) | 1.9(8) | 0.6(9) |
| C28 | 31.2(13) | 29.4(14) | 43.5(14) | 0.1(12) | −1.6(11) | −2.7(11) |
| C12 | 28.5(12) | 31.1(14) | 35.0(13) | 0.7(11) | 4.2(10) | −1.3(10) |
| C11 | 25.8(13) | 38.8(16) | 39.9(15) | −2.0(12) | −1.8(11) | 0.4(11) |
| C9 | 29.5(14) | 48.7(18) | 41.1(15) | −9.2(14) | 4.5(11) | 1.8(13) |
| C17 | 34.6(14) | 34.6(14) | 33.4(13) | −1.3(12) | 1.8(10) | −4.7(12) |
| C13 | 31.9(13) | 38.9(16) | 39.1(14) | 0.3(13) | 0.0(11) | −1.3(12) |
| C26 | 31.2(13) | 30.9(13) | 45.5(16) | −0.7(12) | −1.8(11) | 1.3(11) |
| C2 | 30.7(13) | 47.2(17) | 36.0(14) | −3.7(13) | 2.2(11) | −1.6(13) |
| C8 | 24.1(12) | 45.1(17) | 37.0(14) | −7.5(12) | 3.5(10) | −3.1(12) |
| C1 | 24.4(12) | 46.7(17) | 38.2(15) | −2.2(13) | 3.1(10) | −2.5(12) |
| C24 | 25.2(12) | 36.6(16) | 45.0(16) | −2.3(12) | 0.3(11) | −1.3(11) |
| C18 | 36.8(15) | 39.8(16) | 36.0(14) | −0.6(13) | −2.0(11) | −7.1(13) |
| C22 | 31.7(13) | 32.7(14) | 40.0(15) | −3.5(12) | −0.1(11) | −0.6(12) |
| C3 | 34.0(15) | 44.6(17) | 44.6(16) | 0.8(14) | −1.6(12) | −0.8(13) |
| C25 | 30.8(13) | 27.1(13) | 42.0(15) | −2.2(12) | −0.5(11) | −1.1(11) |
| C31 | 37.1(15) | 37.8(15) | 41.7(15) | 7.4(13) | 3.3(12) | 2.1(12) |
| C6 | 30.4(14) | 51.6(19) | 39.8(15) | −6.2(14) | 2.7(11) | −5.0(13) |
| C23 | 28.7(13) | 37.2(15) | 43.7(16) | 1.4(13) | −3.1(11) | 1.8(12) |
| C30 | 36.7(15) | 41.7(16) | 37.5(14) | 3.1(13) | 2.6(11) | 0.0(13) |
| C27 | 26.8(13) | 34.6(15) | 46.4(16) | −2.8(13) | −0.2(11) | 2.8(11) |
| C10 | 29.3(13) | 40.0(16) | 47.9(16) | −7.4(14) | 0.8(11) | 5.6(13) |
| C16 | 47.9(18) | 35.6(16) | 43.5(16) | −4.9(13) | 5.1(13) | −3.5(14) |
| C15 | 42.7(18) | 35.7(17) | 62(2) | −5.8(15) | 12.1(15) | 6.5(13) |
| C4 | 28.8(14) | 56(2) | 41.9(16) | 8.1(15) | −0.9(11) | −2.0(14) |
| C14 | 28.7(14) | 39.9(17) | 55.8(19) | 4.1(14) | 0.9(12) | 2.1(12) |
| C5 | 30.8(14) | 64(2) | 35.2(14) | −0.8(14) | 2.5(11) | −2.9(14) |
| C34 | 42.7(17) | 52(2) | 45.6(17) | 0.8(15) | 0.3(13) | 8.4(15) |
| C33 | 47.8(18) | 48.9(19) | 51.0(18) | 0.3(16) | −1.6(15) | −9.8(16) |

TABLE 4

Bond Lengths in Å for Atropisomer A-2

| Atom | Atom | Length/Å |
|---|---|---|
| Cl36 | C4 | 1.746(4) |
| F19 | C18 | 1.336(4) |
| F20 | C18 | 1.338(4) |
| F21 | C18 | 1.331(4) |
| O35 | C28 | 1.234(4) |
| N29 | C28 | 1.340(4) |
| N29 | C30 | 1.457(4) |

TABLE 4-continued

Bond Lengths in Å for Atropisomer A-2

| Atom | Atom | Length/Å |
|---|---|---|
| C17 | C16 | 1.388(5) |
| C17 | C18 | 1.510(4) |
| C13 | C14 | 1.386(5) |
| C26 | C27 | 1.377(5) |
| C26 | C25 | 1.391(4) |
| C2 | C3 | 1.388(5) |
| C2 | C1 | 1.400(5) |

TABLE 4-continued

Bond Lengths in Å for Atropisomer A-2

| Atom | Atom | Length/Å |
|---|---|---|
| N32 | C33 | 1.456(4) |
| N32 | C34 | 1.459(5) |
| N32 | C31 | 1.461(4) |
| N7 | C11 | 1.392(4) |
| N7 | C8 | 1.396(4) |
| N7 | C12 | 1.429(4) |
| C28 | C25 | 1.501(4) |
| C12 | C13 | 1.384(4) |
| C12 | C17 | 1.397(4) |
| C11 | C10 | 1.370(4) |
| C11 | C22 | 1.466(4) |
| C9 | C8 | 1.372(5) |
| C9 | C10 | 1.403(5) |

TABLE 4-continued

| Bond Lengths in Å for Atropisomer A-2 | | |
|---|---|---|
| Atom | Atom | Length/Å |
| C8 | C1 | 1.468(5) |
| C1 | C6 | 1.409(4) |
| C24 | C23 | 1.389(5) |
| C24 | C25 | 1.390(4) |
| C22 | C23 | 1.396(4) |
| C22 | C27 | 1.404(4) |
| C3 | C4 | 1.385(5) |
| C31 | C30 | 1.521(5) |
| C6 | C5 | 1.387(5) |
| C16 | C15 | 1.390(5) |
| C15 | C14 | 1.383(5) |
| C4 | C5 | 1.377(6) |

TABLE 5

| Bond Angles in ° for Atropisomer A-2 | | | |
|---|---|---|---|
| Atom | Atom | Atom | Angle/° |
| C28 | N29 | C30 | 122.6(3) |
| C33 | N32 | C34 | 109.6(3) |
| C33 | N32 | C31 | 110.1(3) |
| C34 | N32 | C31 | 112.1(2) |
| C11 | N7 | C8 | 109.1(3) |
| C11 | N7 | C12 | 126.6(2) |
| C8 | N7 | C12 | 124.2(3) |
| O35 | C28 | N29 | 123.2(3) |
| O35 | C28 | C25 | 120.5(3) |
| N29 | C28 | C25 | 116.2(3) |
| C13 | C12 | C17 | 120.0(3) |
| C13 | C12 | N7 | 118.8(3) |
| C17 | C12 | N7 | 121.2(3) |
| C10 | C11 | N7 | 107.1(3) |
| C10 | C11 | C22 | 128.6(3) |
| N7 | C11 | C22 | 124.3(3) |
| C8 | C9 | C10 | 108.4(3) |
| C16 | C17 | C12 | 119.5(3) |
| C16 | C17 | C18 | 118.7(3) |
| C12 | C17 | C18 | 121.8(3) |
| C12 | C13 | C14 | 120.4(3) |
| C27 | C26 | C25 | 120.5(3) |
| C3 | C2 | C1 | 121.7(3) |
| C9 | C8 | N7 | 106.9(3) |
| C9 | C8 | C1 | 128.1(3) |
| N7 | C8 | C1 | 125.0(3) |
| C2 | C1 | C6 | 117.3(3) |
| C2 | C1 | C8 | 125.0(3) |
| C6 | C1 | C8 | 117.6(3) |
| C23 | C24 | C25 | 120.8(3) |
| F21 | C18 | F19 | 106.0(2) |
| F21 | C18 | F20 | 107.3(3) |
| F19 | C18 | F20 | 105.9(3) |
| F21 | C18 | C17 | 111.8(3) |
| F19 | C18 | C17 | 113.1(2) |
| F20 | C18 | C17 | 112.3(2) |
| C23 | C22 | C27 | 117.9(3) |
| C23 | C22 | C11 | 123.1(3) |
| C27 | C22 | C11 | 119.0(3) |
| C4 | C3 | C2 | 118.8(3) |
| C24 | C25 | C26 | 118.9(3) |
| C24 | C25 | C28 | 121.4(3) |
| C26 | C25 | C28 | 119.6(3) |
| N32 | C31 | C30 | 113.9(3) |
| C5 | C6 | C1 | 121.6(3) |
| C24 | C23 | C22 | 120.6(3) |
| N29 | C30 | C31 | 112.1(2) |
| C26 | C27 | C22 | 121.3(3) |
| C11 | C10 | C9 | 108.5(3) |
| C17 | C16 | C15 | 120.0(3) |
| C14 | C15 | C16 | 120.4(3) |
| C5 | C4 | C3 | 121.8(3) |
| C5 | C4 | Cl36 | 119.1(3) |
| C3 | C4 | Cl36 | 119.1(3) |

TABLE 5-continued

| Bond Angles in ° for Atropisomer A-2 | | | |
|---|---|---|---|
| Atom | Atom | Atom | Angle/° |
| C15 | C14 | C13 | 119.6(3) |
| C4 | C5 | C6 | 118.9(3) |

TABLE 6

| Torsion Angles in ° for Atropisomer A-2 | | | | |
|---|---|---|---|---|
| Atom | Atom | Atom | Atom | Angle/° |
| C30 | N29 | C28 | O35 | −8.5(4) |
| C30 | N29 | C28 | C25 | 170.8(2) |
| C11 | N7 | C12 | C13 | −110.3(3) |
| C8 | N7 | C12 | C13 | 74.5(4) |
| C11 | N7 | C12 | C17 | 71.3(4) |
| C8 | N7 | C12 | C17 | −103.9(3) |
| C8 | N7 | C11 | C10 | 0.3(3) |
| C12 | N7 | C11 | C10 | −175.5(3) |
| C8 | N7 | C11 | C22 | −177.3(3) |
| C12 | N7 | C11 | C22 | 6.8(4) |
| C13 | C12 | C17 | C16 | 2.1(4) |
| N7 | C12 | C17 | C16 | −179.5(3) |
| C13 | C12 | C17 | C18 | −174.1(3) |
| N7 | C12 | C17 | C18 | 4.3(4) |
| C17 | C12 | C13 | C14 | −0.8(5) |
| N7 | C12 | C13 | C14 | −179.2(3) |
| C10 | C9 | C8 | N7 | −0.8(3) |
| C10 | C9 | C8 | C1 | 179.0(3) |
| C11 | N7 | C8 | C9 | 0.3(3) |
| C12 | N7 | C8 | C9 | 176.2(3) |
| C11 | N7 | C8 | C1 | −179.4(3) |
| C12 | N7 | C8 | C1 | −3.5(4) |
| C3 | C2 | C1 | C6 | 0.1(4) |
| C3 | C2 | C1 | C8 | 177.6(3) |
| C9 | C8 | C1 | C2 | −141.6(3) |
| N7 | C8 | C1 | C2 | 38.1(4) |
| C9 | C8 | C1 | C6 | 35.8(4) |
| N7 | C8 | C1 | C6 | −144.5(3) |
| C16 | C17 | C18 | F21 | −11.9(4) |
| C12 | C17 | C18 | F21 | 164.2(3) |
| C16 | C17 | C18 | F19 | 107.6(3) |
| C12 | C17 | C18 | F19 | −76.2(4) |
| C16 | C17 | C18 | F20 | −132.6(3) |
| C12 | C17 | C18 | F20 | 43.6(4) |
| C10 | C11 | C22 | C23 | −139.7(3) |
| N7 | C11 | C22 | C23 | 37.4(5) |
| C10 | C11 | C22 | C27 | 38.3(5) |
| N7 | C11 | C22 | C27 | −144.6(3) |
| C1 | C2 | C3 | C4 | 0.2(5) |
| C23 | C24 | C25 | C26 | 0.2(5) |
| C23 | C24 | C25 | C28 | −175.1(3) |
| C27 | C26 | C25 | C24 | 1.3(5) |
| C27 | C26 | C25 | C28 | 176.7(3) |
| O35 | C28 | C25 | C24 | 144.1(3) |
| N29 | C28 | C25 | C24 | −35.3(4) |
| O35 | C28 | C25 | C26 | −31.2(4) |
| N29 | C28 | C25 | C26 | 149.5(3) |
| C33 | N32 | C31 | C30 | 169.7(3) |
| C34 | N32 | C31 | C30 | −68.1(4) |
| C2 | C1 | C6 | C5 | 0.0(4) |
| C8 | C1 | C6 | C5 | −177.6(3) |
| C25 | C24 | C23 | C22 | −1.3(5) |
| C27 | C22 | C23 | C24 | 0.9(5) |
| C11 | C22 | C23 | C24 | 179.0(3) |
| C28 | N29 | C30 | C31 | −80.9(4) |
| N32 | C31 | C30 | N29 | −55.5(4) |
| C25 | C26 | C27 | C22 | −1.7(5) |
| C23 | C22 | C27 | C26 | 0.6(5) |
| C11 | C22 | C27 | C26 | −177.6(3) |
| N7 | C11 | C10 | C9 | −0.8(3) |
| C22 | C11 | C10 | C9 | 176.8(3) |
| C8 | C9 | C10 | C11 | 0.9(3) |
| C12 | C17 | C16 | C15 | −1.7(5) |
| C18 | C17 | C16 | C15 | 174.6(3) |

TABLE 6-continued

Torsion Angles in ° for Atropisomer A-2

| Atom | Atom | Atom | Atom | Angle/° |
|---|---|---|---|---|
| C17 | C16 | C15 | C14 | −0.1(5) |
| C2 | C3 | C4 | C5 | −0.7(5) |
| C2 | C3 | C4 | Cl36 | 177.7(2) |
| C16 | C15 | C14 | C13 | 1.5(5) |
| C12 | C13 | C14 | C15 | −1.0(5) |
| C3 | C4 | C5 | C6 | 0.8(5) |
| Cl36 | C4 | C5 | C6 | −177.5(2) |
| C1 | C6 | C5 | C4 | −0.5(4) |

TABLE 7

Hydrogen Fractional Atomic Coordinates ($\times 10^4$) and Equivalent Isotropic Displacement Parameters ($Å^2 \times 10^3$) for Atropisomer A-2. $U_{eq}$ is defined as ⅓ of the trace of the orthogonalised $U_{ij}$.

| Atom | x | y | z | $U_{eq}$ |
|---|---|---|---|---|
| H29 | 4556.28 | 2597.1 | 9613.5 | 44 |
| H9 | 9373.45 | 3631.45 | 4279.86 | 48 |
| H13 | 5075.26 | 5792.63 | 5065.04 | 44 |
| H26 | 8091.21 | 838.52 | 8764.29 | 43 |
| H2 | 7844.85 | 8248.03 | 5190.71 | 46 |
| H24 | 4521.78 | 2695.77 | 8048.38 | 43 |
| H3 | 7771.85 | 10303.2 | 4130.77 | 49 |
| H31A | 3309.1 | −1006.73 | 9802.84 | 47 |
| H31B | 2411.76 | −508.61 | 10623.33 | 47 |
| H6 | 8091.06 | 5215.49 | 3052.71 | 49 |
| H23 | 5315.8 | 3715.16 | 6693.61 | 44 |
| H30A | 3620.15 | 1767.17 | 10885.52 | 46 |
| H30B | 4611.45 | 327.4 | 10937.24 | 46 |
| H27 | 8912.55 | 1941.11 | 7453.43 | 43 |
| H10 | 9042.29 | 1887.07 | 5647.28 | 47 |
| H16 | 6460.32 | 8712.19 | 7693.92 | 51 |
| H15 | 4381.36 | 9123.95 | 6944.76 | 56 |
| H14 | 3703.76 | 7704.45 | 5613.91 | 50 |
| H5 | 8029.04 | 7271.37 | 1993.52 | 52 |
| H34A | 665.96 | 1339.38 | 10310.64 | 71 |
| H34B | 634.49 | 2342.88 | 9371.1 | 71 |
| H34C | 1786.66 | 2599.59 | 10171.65 | 71 |
| H33A | 1667.2 | −1246.13 | 8637.31 | 74 |
| H33B | 539.51 | 36.17 | 8485.32 | 74 |
| H33C | 622.37 | −1010.97 | 9408.31 | 74 |

Figure 2:
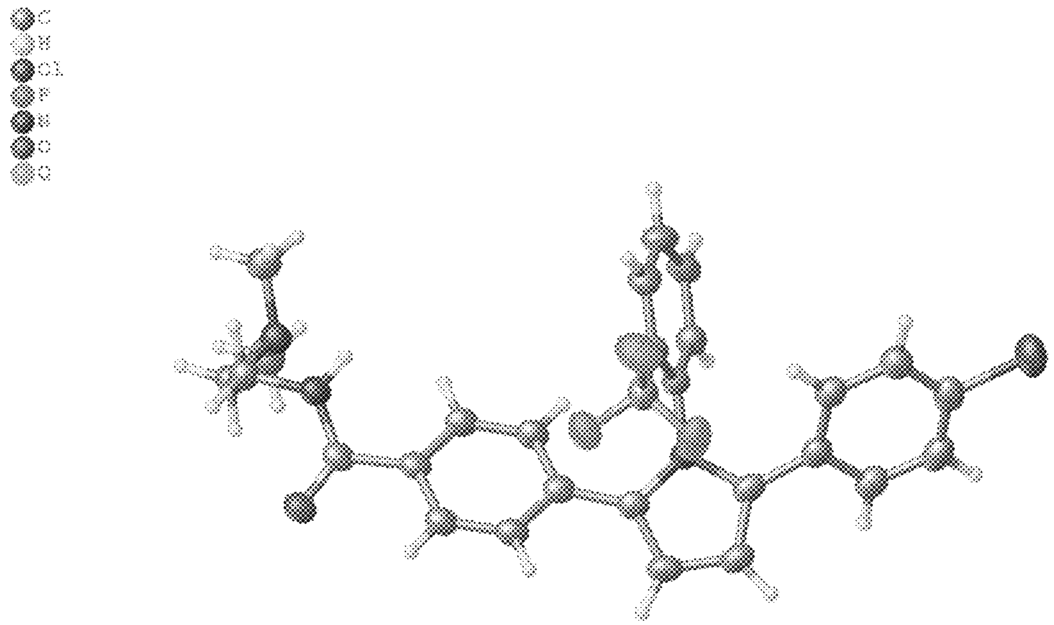
FIG. 2 is a depiction of the three dimensional structure of 4-[5-(4-chlorophenyl)-1-[2-(trifluoromethyl)-phenyl]pyrrol-2-yl]-N-[2-(dimethylamino)-ethyl]benzamide atropisomer A-2 as determined by single crystal X-ray crystallographic studies.
Figure 3:
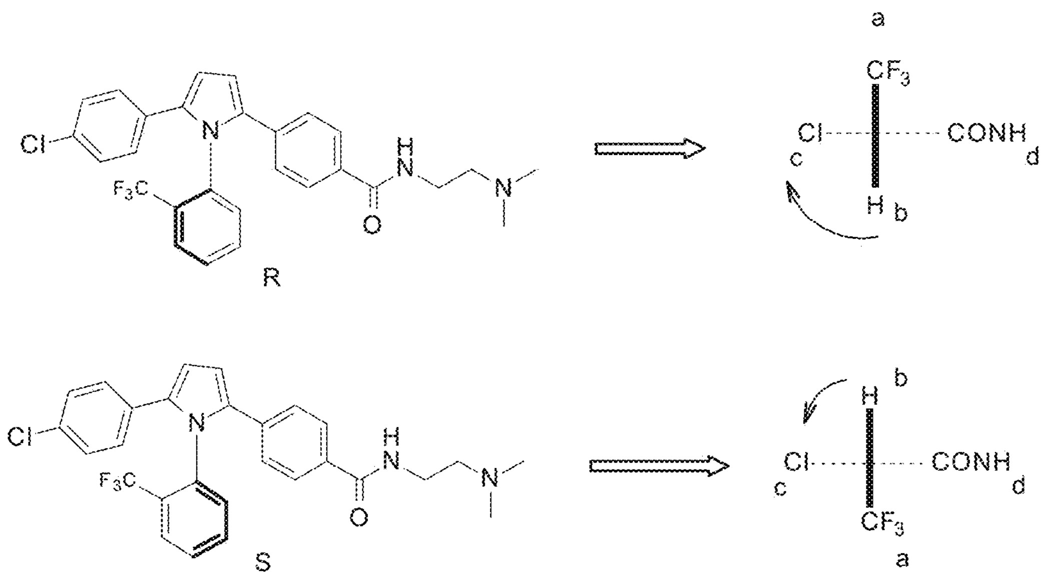
FIG. 3 is a schematic stereochemical illustration of the two atropisomers A-1 (S) and A-2 (R) and the basis for assigning their stereochemical structures using the Cahn-Ingold-Prelog (CIP) sequence rules.

On the basis of the data set out below, atropisomer A-2 is believed to have the R configuration as shown in FIGS. 2 and 3 and can therefore be named as (R)-4-[5-(4-chlorophenyl)-1-[2-(trifluoromethyl)phenyl]pyrrol-2-yl]-N-[2 (dimethylamino)-ethyl]benzamide.

Example 4

Preparation and characterisation of (R)-4-[5-(4-chlorophenyl)-1-[2-(trifluoromethyl)phenyl]pyrrol-2-yl]-N-[2 (dimethylamino)ethyl]benzamide tartrate salt Method 1: Small Scale Preparation of Tartrate Salt Atropisomer A-2 free base (904.2 mg) was suspended in acetone (9.042 mL, 10 vols) and stirred at 25° C. for 40 minutes. When the solution was free of visible particulates, it was split into 12 equal aliquots (603 μL), giving an approximate active content of 60.3 mg per sample.

An aliquot of 247 μL (1.05 eq) of a 0.5 M solution of tartaric acid in ethanol was added to an aliquot of the free base solution at 25° C. The mixture was stirred at 25° C. for 18 hours after which time a white suspension formed, and the resulting solids were then isolated by filtration (PTFE 10 micron fritted cartridge) and dried in vacuo at 40° C. for ca. 72 hours. The resulting salt was labelled as Tartrate Pattern A (solvate).

Method 2: Preparation of Tartrate Salt Using an Isopropyl Acetate Solution of Atropisomer A-2

Atropisomer A-2 (749.8 mg) was suspended in isopropyl acetate (15 mL, 20 vols) and the suspension was heated to 40° C. with agitation. When the solution was free of visible particulates, it was split into 12 equal aliquots (1 mL), giving an approximate active content of 50 mg per sample. An aliquot of 195.3 μL of a 1 M solution of atropisomer A-2 in ethanol was added to an aliquot of the free base solution at 40° C. The resulting mixture was cooled to 25° C. at a cooling rate of approximately 10° C./hour. A white suspension formed and the resulting solids were then isolated by filtration and dried in vacuo at 40° C. for ca. 18 hours. The resulting salt was labelled as Tartrate Pattern B.

Method 3: Preparation of Tartrate Salt Using an Isopropyl Alcohol Solution of Atropisomer A-2

By following Method 2, except that atropisomer A-2 (750.1 mg) was initially suspended in isopropyl alcohol (15 mL, 20 vols), Tartrate Pattern A salt was prepared.

Method 4: Preparation of Tartrate Salt Using a 2-Methyl-Tetrahydrofuran Solution of Atropisomer A-2

Method 1 was repeated, except that atropisomer A-2 (913.9 mg) was initially suspended in 2-methyl-tetrahydrofuran (15 mL, 20 vols), (9.139 mL, 10 vols) and stirred at 25° C. for ca. 40 minutes, and then a 250 μL (1.05 eq) aliquot of 1 M tartaric acid in ethanol was added to an aliquot (609 μL) of the A-2 free base solution, to give Tartrate Pattern A salt.

Method 5: 500 mg Scale Preparation of Atropisomer A-2 Tartrate Pattern B Salt

Atropisomer A-2 free base (521.5 mg) was weighed into a glass vial and charged with isopropyl acetate (20 vols, 10.430 mL). The mixture was heated to 40° C. and stirred for 15 minutes to give a clear solution. The solution was then charged with tartaric acid (1.05 eq, 162.5 mg) dissolved in 3 mL of tetrahydrofuran. The resulting mixture was seeded with atropisomer A-2.tartrate pattern B, which caused the salt to immediately precipitate at 40° C. forming a mobile suspension. The mixture was cooled to 25° C. and stirred for 20 hours. The resulting solid was isolated by filtration and dried at 40° C. in vacuo to afford the atropisomer A-2 Tartrate Pattern B salt in 84% yield.

Method 6: Scaled-Up Preparation of Atropisomer A-2 Tartrate Pattern B Salt (Anhydrous Form)

Atropisomer A-2 free base (10.0497 g) was weighed into a Buchi flask and charged with isopropyl acetate (20 vols, 200 ml). The mixture was heated to 40° C. to afford a clear solution, free of particulates, and stirred for 30 minutes. The solution was charged with tartaric acid (3.1954 g, 1.08 eq.) dissolved in tetrahydrofuran (50 mL), the acid being was added in portions as follows: 15 mL at 40° C.; seeded with atropisomer A-2 Tartrate Pattern B salt and stirred for 30 minutes; 10 mL and stirred for 1 hour; 10 mL and stirred for 30 minutes; 15 mL and stirred for 30 minutes. The white suspension was then cooled to RT at a cooling rate of 10° C./h and stirred for 18 hours. The resulting solid was isolated by filtration in vacuo and washed with isopropyl acetate (2×2 vols) and dried in vacuo at 40° C. for 20 hours to afford the A-2 Tartrate Pattern B salt (anhydrous) in a yield of 97%; HPLC purity 99.74% (HPLC method 1), chiral purity 99.27% (Chiral HPLC method 7).

Method 7: Alternative Scaled-Up Preparation of Atropisomer A-2 Tartrate Pattern B Salt (Anhydrous Form) by Cooling Crystallisation from Butanol/Water 96:4

Atropisomer A-2 free base (36.79 g) was weighed into a flask and charged with butanol (282.57 ml, 7.68 vols). The mixture was heated to 80° C. (pale yellow, hazy solution) and stirred for 30 minutes before clarification into a Mya* vessel, pre-heated at 80° C. The solution was then charged with L-(+)-tartaric acid (1.023 eq, 11.0806 g) as a solution in water (11.77 ml, 0.32 vols of the initial API charge). The addition was made dropwise at 80° C. with clarification of the acid solution. The mixture was then cooled to 68° C. over a period of 30 minutes, seeded with 0.1% of ground atropisomer A-2 Tartrate Pattern B salt seed crystals (32.6 mg) and held for 1 hour. The mixture was then cooled to 5° C. at a cooling rate of 5° C./hour and stirred at 5° C. for 6 hours before isolation of the solid. The solid was filtered in vacuo, washed twice with butanol and dried for 15 minutes on the filter and then at 40° C. for 20 hours to afford atropisomer A-2 Tartrate Pattern B salt (anhydrous) in a yield of 83%; HPLC purity 99.84% (HPLC method 1), chiral purity 99.66% (Chiral HPLC method 7).

Note: In the foregoing equilibrations or crystallisations that required temperature control and/or defined heating/cooling profiles, a Radley's Mya4 Reaction Station was used. The Radley's Mya4 Reaction Station is a 4-zone reaction station with magnetic and overhead stirring capabilities and a temperature range of −30 to 180° C. on 2 to 400 mL scale mixtures. The reaction conditions required were programmed via the Mya 4 Control Pad.

Characterisation of the Atropisomer A-2 Tartrate Salts

The identities of the salts as 1:1 (molar ratio of free base:tartaric acid) stoichiometric salts were confirmed from their $^1$H NMR spectra which were collected using a JEOL ECX 400 MHz spectrometer equipped with an auto-sampler. The samples were dissolved in a suitable deuterated solvent for analysis. The data were acquired using Delta NMR Processing and Control Software version 4.3.

The tartrate salts were characterised using X-ray powder diffraction (XRPD), differential scanning calorimetry (DSC), thermogravimetric analysis (TGA), gravimetric solubility tests and gravimetric vapour sorption tests using the techniques described below.

X-Ray Powder Diffraction (XRPD)

X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d. XRPD patterns were acquired under ambient conditions via a transmission foil sample stage (polyimide—Kapton, 12.7 μm thickness film) under ambient conditions using a PANalytical X'Pert PRO. The data collection range was 2.994-35°2θ with a continuous scan speed of 0.202004° s-1.

Differential Scanning Calorimetry (DSC)

DSC data were collected on a PerkinElmer Pyris 6000 DSC equipped with a 45-position sample holder. The instrument was verified for energy and temperature calibration using certified indium. A predefined amount of the sample, 0.5-3.0 mg, was placed in a pin-holed aluminium pan and heated at 20° C. min$^{-1}$ from 30 to 350° C. or varied as experimentation dictated. A purge of dry nitrogen at 20 ml min$^{-1}$ was maintained over the sample. The instrument control, data acquisition and analysis were performed with Pyris Software v11.1.1 revision H.

Thermo-Gravimetric Analysis (TGA)

TGA data were collected on a PerkinElmer Pyris 1 TGA equipped with a 20-position auto-sampler. The instrument was calibrated using a certified weight and certified Alumel and Perkalloy for temperature. A predefined amount of the sample, 1-5 mg, was loaded onto a pre-tared aluminium crucible and heated at 20° C. min$^{-1}$ from ambient temperature to 400° C. A nitrogen purge at 20 ml·min$^{-1}$ was maintained over the sample. Instrument control, data acquisition and analysis were performed with Pyris Software v11.1.1 revision H.

Gravimetric Solubility

The solubility in water of the salts was measured using a gravimetric solubility protocol.

1 ml of water was charged into crystallisation tubes. The solid was weighed into a tared glass vial, added in portions to the solutions and the vial weighed after each addition until a hazy solution was observed. The amount in mg was then calculated to give the solubility in mg/ml.

The results obtained from the characterisation studies are set out in Table 8 below.

TABLE 8

Figure 4:
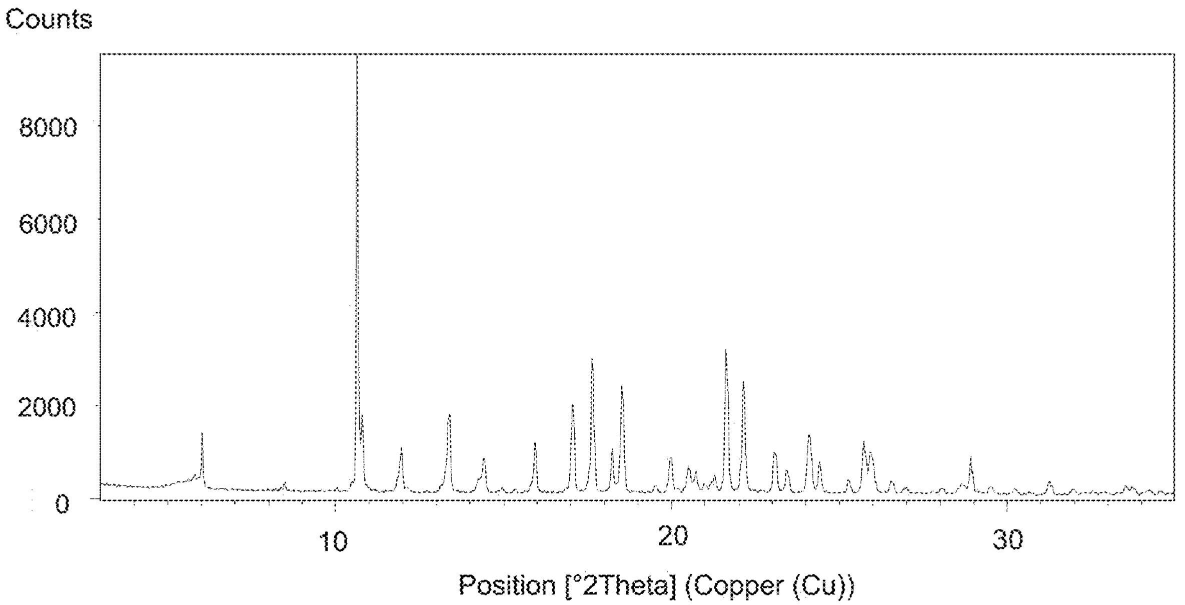
FIG. 4 is an X-ray powder diffraction spectrum for atropisomer A-2 free base.
Figure 5:
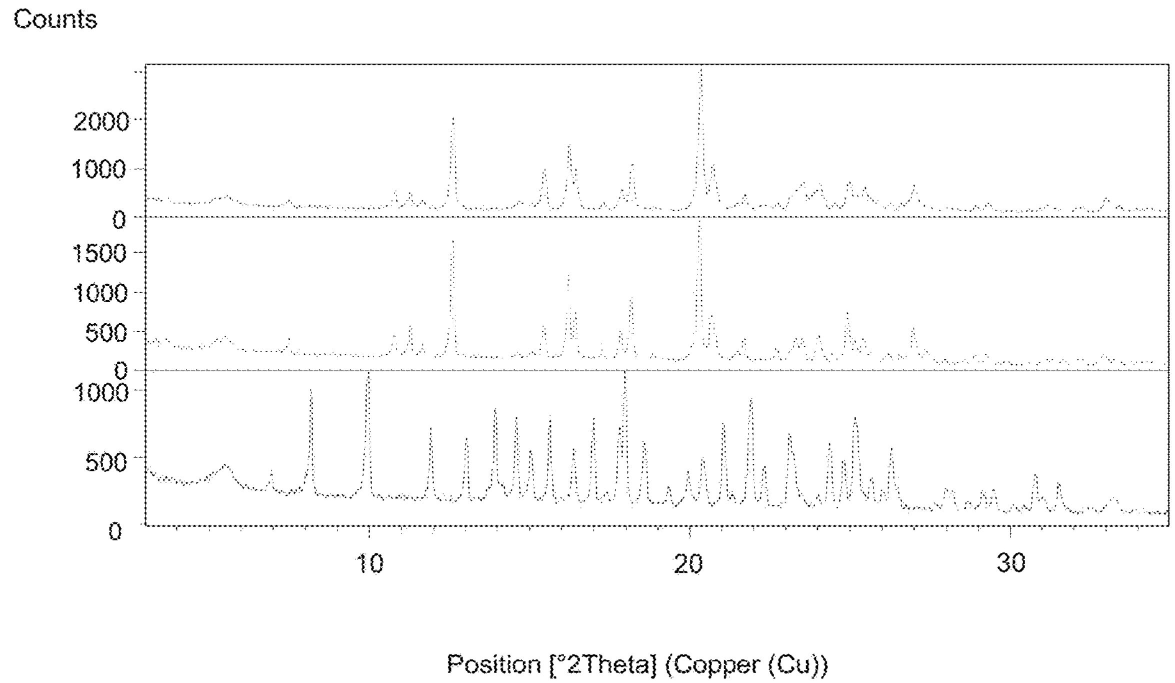
FIG. 5 is an X-ray powder diffraction spectrum for atropisomer A-2 Tartrate Pattern A salt (bottom line) and Pattern B salt (top and middle lines)
Figure 6:
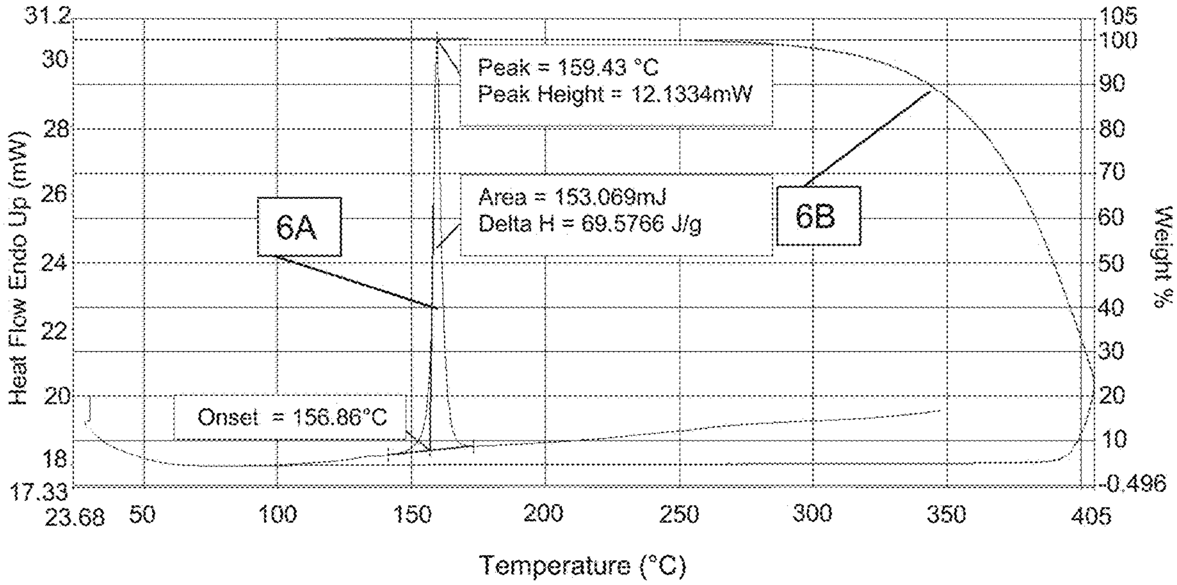
FIG. 6 illustrates the thermal profile for atropisomer A-2 free base and shows a differential scanning calorimetry plot (line 6A) and a thermo-gravimetric analysis plot (line 6B).
Figure 7:
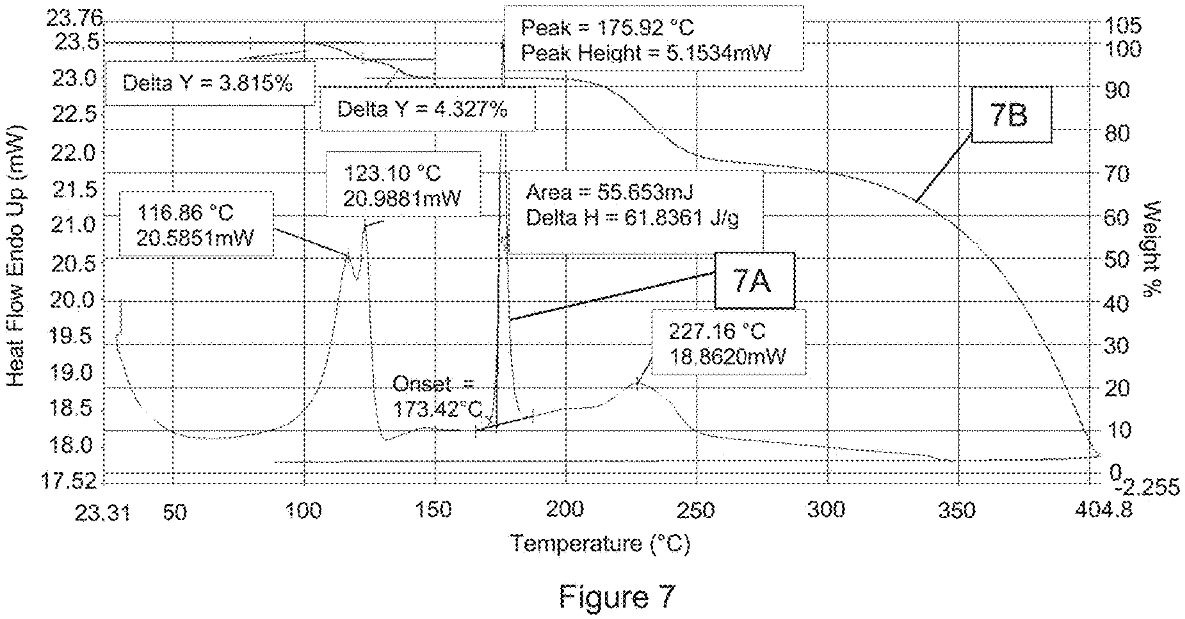
FIG. 7 illustrates the thermal profile for atropisomer A-2 Tartrate Pattern A salt and shows a differential scanning calorimetry plot (line 7A) and a thermo-gravimetric analysis plot (line 7B).
Figure 8:
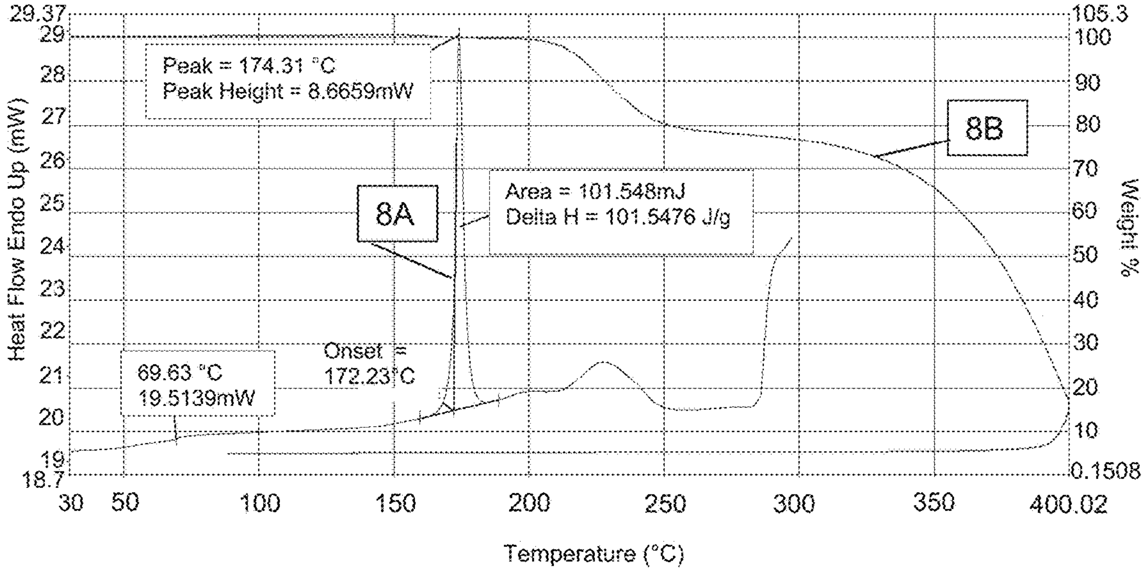
FIG. 8 illustrates the thermal profile for atropisomer A-2 Tartrate Pattern B salt and shows a differential scanning calorimetry plot (line 8A) and a thermo-gravimetric analysis plot (line 8B).

| Salt | XRPD pattern | XRPD FIG. | DSC | TGA | Solubility in water (mg/mL) |
|---|---|---|---|---|---|
| Free base | Pattern A | FIG. 4 | FIG. 6 onset 157° C. peak 159° C. | FIG. 6 | <5 |
| Tartrate | Pattern A (EtOH solvate) | FIG. 5 | FIG. 7 onset ~173° C. peak ~175° C., thermal event 117° C. | FIG. 7 78-157° C. loss 6% | 6.7 |
| Tartrate | Pattern B (anhydrous) | FIG. 5 | FIG. 8 onset ~172° C. peak at ~174° C. | FIG. 8 | 7.5 |

Gravimetric Vapour Sorption (GVS)

GVS studies were carried out on atropisomer A-2 Tartrate Pattern B salt using the protocol set out below:

Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min-1. The instrument was verified for relative humidity content by measuring three calibrated Rotronic salt solutions (10-50-88%). The weight change of the sample was monitored as a function of humidity by a microbalance (accuracy+/−0.005 mg). A defined amount of sample was placed in a tared mesh stainless steel basket under ambient conditions. A full experimental cycle typically consisted of three scans (sorption, desorption and sorption) at a constant temperature (25° C.) and 10% RH intervals over a 0-90% range (60 minutes for each humidity level). This type of experiment should demonstrate the ability of samples studied to absorb moisture (or not) over a set of well-determined humidity ranges.

Figure 9:
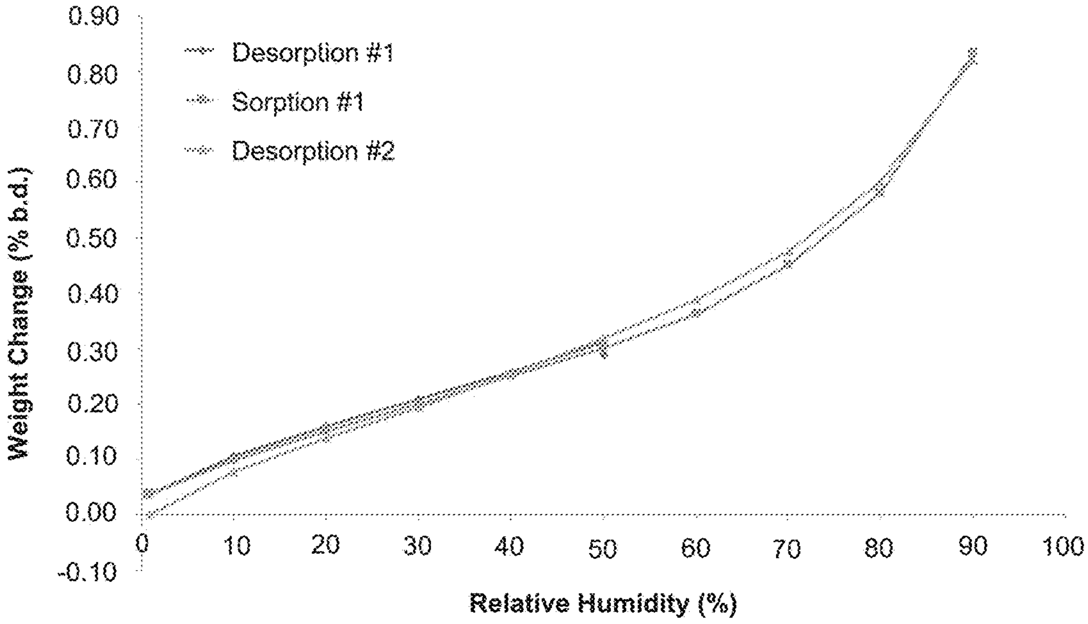
FIG. 9 is a plot of weight change versus relative humidity in Gravimetric Vapour Sorption studies carried out on atropisomer A-2 Tartrate Pattern B salt.

GVS analysis (see FIG. 9) indicated a moisture content of ca. 0.3% before the first desorption. Between 80 and 90% RH there is a slightly higher increase in moisture, with the solid taking ca. 0.8% moisture. The second absorption/desorption cycle shows how the moisture uptake is completely reversible, with a return to 0 wt % at at 0% RH. XRPD post GVS cycling held at 0% RH and 90% RH for a minimum of 3 hours afforded anhydrous Pattern B at both RH values.

It can therefore be concluded that the atropisomer A-2 Tartrate Pattern B salt exists as a stable solid, only absorbing surface moisture with no change in form.

Example 5

Further characteristics of (R)-4-[5-(4-chlorophenyl)-1-[2-(trifluoromethyl)phenyl]pyrrol-2-yl]-N-[2 (dimethylamino)ethyl]benzamide tartrate salt Solubility Atropisomer A-2 Tartrate Pattern B salt was found to be highly soluble in aqueous formulations, making it suitable for oral delivery. A concentration of >100 mg/mL was achieved in a solution of (2-hydroxypropyl)-β-cyclodextrin 20% w/v in water following continuous stirring and gentle warming to 40° C.

Powder Density

The bulk density was measured by charging Atropisomer A-2 Tartrate Pattern B salt to a 50 mL glass beaker. The compound was allowed to settle prior to weighing with approximately 40 mL volume occupied and bulk density calculated.

The tap density was determined by charging 6-8 mL of Atropisomer A-2 Tartrate Pattern B salt into a 10 mL graduated cylinder, following which the material was tapped and vibrated repeatedly for 15 minutes manually in a vertical and horizontal manner using a rubber mat and mallet or until a consistent bed that settled no further was achieved. The tap density was then calculated.

Atropisomer A-2 Tartrate Pattern B salt has a powder bulk density value of 0.55 g/mL and tap density of ~0.659 g/mL.

The flowability of a drug powder and hence its suitability for formulating in a capsule form can be defined by its Carr's index and Hausner ratio which can be calculated from its bulk density and tap density according to the following formulae:

$$\text{Carr Compressibility index}=100(\rho T-\rho B)/\rho T$$

$$\text{Hausner Ratio}=\rho T/\rho B$$

The Carr's index and Hausner ratio can then be converted to a flowability descriptor as set out in the table below (source: https://www.researchgate.net/figure/Specifications-for-Carrs-index-and-Hausner-ratio_tbl1_325365029).

| Carr's index | Flowability | Hausner ratio |
|---|---|---|
| ≤10 | Excellent | 1.00-1.11 |
| 11.0-15.0 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Awful | >1.60 |

For Atropisomer A-2 Tartrate Pattern B salt, the Carr's index was calculated as 16.5% and the Hausner ratio was calculated as 1.19 indicating "fair" flowability. Therefore, this salt form is suitable for powder in capsule dosing.

Stability

The stability of Atropisomer A-2 Tartrate Pattern B salt was assessed using two sets of storage conditions; namely 25° C.±2° C./60% RH and 40° C.±2° C./75% RH. The stability protocol followed ICH guidelines.

Thus, Atropisomer A-2 Tartrate Pattern B salt (1 g per container) was placed into ICH rated stability cabinets at 25° C./60% RH and 40° C./75% RH with the following packing components:

Double polythene bags (Vendor—Armagrip; part no G01-PB-120),

Wide mouth HDPE bottle with screw cap closure (Vendor—Curtec; part no 4303),

Plastic tie strips (Vendor—Thomas & Betts; part no TY125-40-100).

Following storage, these samples were removed from the stability cabinet and analysed for appearance, water content by Karl Fischer titration (KF), and purity. No change in water content or chemical purity by HPLC was observed over six months. No change in water content or chemical purity by HPLC was observed over six months.

| Test | T = 0 | T = 6 month | T = 6 month |
|---|---|---|---|
| Condition | n/a | 25° C./60% RH | 40° C./75% RH |
| Appearance | A white solid. Free from visible contamination | A white solid. Free from visible contamination | A white solid. Free from visible contamination |
| Chemical purity by HPLC | 99.60% | 99.60% | 99.60% |
| Water content by KF | 0.2% w/w | 0.2% w/w | 0.2% w/w |

Example 6

Alternative Method for Preparing (R)-4-[5-(4-chlorophenyl)-1-[2-(trifluoromethyl)phenyl]pyrrol-2-yl]-N-[2 (dimethylamino)ethyl]benzamide (Atropisomer A-2)

(1)

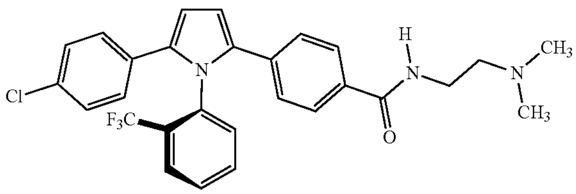

The title compound was prepared by following Steps 1, 2, 3, 4a and 5a of the synthetic routes shown in Scheme 1 above. In this route, chiral resolution is carried out on the carboxylic acid intermediate (8) rather than on the dimethylamino-ethyl amide (9).

Step 1: 4-[4-(4-chlorophenyl)-4-oxo-butanoyl]benzonitrile (6)

A flask was charged with tetrahydrofuran (4 mL/g) and zinc chloride (1.222 g/g, 1.3 eq) was added in portions to afford a white mobile suspension which was stirred for 15 min. tert-Butanol (0.66 mL/g, 1 eq) was added followed by triethylamine (0.96 mL/g, 1 eq) in portions keeping the temperature below 40° C. The reaction was stirred for 2 h. 4-Cyanoacetophenone (1 g/g, 1 eq) and 4-chlorophenacyl bromide (1.61 g/g, 1 eq) were added and the reaction mixture was stirred at 20° C. (±5) for 48 h or until reaction was complete. The product was isolated by precipitation with aqueous HCl and slurry in aqueous HCl and methanol. The resulting solid was dried under vacuum (45° C.) to afford the title compound as a pale yellow solid.

Step 2: 4-(5-(4-chlorophenyl)-1-(2-(trifluoromethyl) phenyl)-1H-pyrrol-2-yl)benzonitrile (7)

4-(4-(4-Chlorophenyl)-4-oxobutanoyl)benzonitrile (1 g/g, 1 eq) was charged to a flask and dioxane (10 mL/g) was added to afford a yellow suspension. 2-Trifluoromethyl aniline (1.269 mL/g, 3 eq) was added in a single portion followed by p-toluenesulfonic acid (0.06399 g/g, 0.1 eq) and the reaction mixture was heated at 101° C. for 40-72 h (additional portions of p-toluenesulfonic acid (0.1 eq) were added if required every 8 hours to push the reaction to completion). The reaction mixture was cooled to room temperature and concentrated under vacuum. The resulting oily residue was purified by slurring in methanol (10 mL/g). The solid was isolated by filtration and dried under vacuum (45° C.) to afford the title compound as a yellow solid.

Step 3: 4-(5-(4-chlorophenyl)-1-(2-(trifluoromethyl) phenyl)-1H-pyrrol-2-yl)benzoic acid (8)

To 4-(5-(4-Chlorophenyl)-1-(2-(trifluoromethyl)phenyl)-1H-pyrrol-2-yl)benzonitrile (1 g/g, 1 eq) in methanol (10.9 mL/g) was added sodium hydroxide (0.948 g/g, 10 eq) in water (5 mL/g) dropwise over 15 minutes and the resulting mixture was stirred at 70-76° C. for 18 hours or until complete. The reaction mixture was cooled to room temperature, acidified and the product isolated by filtration, washing with water (5 mL/g) and acetonitrile (3 mL/g). The product was slurried in acetone/water (20 vols, 75:25) at 50-55° C. and dried under vacuum (60° C.) to afford the title compound as a yellow solid.

Step 4a: (R) 4-(5-(4-chlorophenyl)-1-(2-(trifluorom-ethyl)phenyl)-1H-pyrrol-2-yl)benzoic acid (3) by chiral resolution of (8)

4-(5-(4-Chlorophenyl)-1-(2-(trifluoromethyl)phenyl)-1H-pyrrol-2-yl)benzoic acid (1 g/g, 1 eq) was added to a flask followed by tetrahydrofuran (2 mL/g) and acetonitrile (0.75 mL/g). (S)-1-(4-methoxyphenyl)-ethylamine (0.335 mL/g, 1 eq) was added dropwise over 5 min and the resulting reaction mixture was stirred at 40-50° C. for 15 min then cooled to room temperature. Acetonitrile (7.25 mL/g) was added and the reaction seeded (0.0001 g/g, 99% ee, (S)-1-(4-methoxyphenyl)-ethylamine salt of desired atropisomer). The reaction mixture was stirred for 16 h and the resulting solids were isolated by filtration washing with acetonitrile. Hot (75-80° C.) slurry in acetonitrile afforded the chiral salt as a white solid (40% yield, 98.16% ee). Salt break was achieved in THF/water (2/2 vols) using 1M HCl (2.2 eq) to afford the acid which was further purified by slurry in water affording the title compound (90.52 g, salt break yield 97%, overall yield 39%, 98.06% ee). $^1$H NMR (DMSO-d6) δ 12.83 (brs, 1H), 7.77-7.67 (m, 6H), 7.23-7.10 (m, 2H), 7.08-7.01 (m, 4H), 6.68 (d, J=4.0 Hz, 1H), 6.59-6.58 (d, J=4.0 Hz, 1H). Chiral HPLC with chiral HPLC method 6 showed a single atropisomer, RT 6.083 min, 99.02% area (minor atropisomer RT 7.07 min, 0.98% area).

Chiral resolution can also be achieved using (S)-(−)-1-phenylethylamine.

Step 5a: (R)-4-[5-(4-chlorophenyl)-1-[2-(trifluorom-ethyl)phenyl]pyrrol-2-yl]-N-[2 (dimethylamino) ethyl]benzamide (1)

4-(5-(4-Chlorophenyl)-1-(2-(trifluoromethyl)phenyl)-1H-pyrrol-2-yl)benzoic acid (single atropisomer, (3)) (1 g/g, 1 eq) was dissolved in THF (5 mL/g) and N,N-dimethyl-ethylenediamine (0.75 mL/g, 3 eq) was added dropwise followed by DIPEA (1.58 mL/g, 4 eq). 50% T3P in THF (2.72 mL/g, 2 eq) was added dropwise and the reaction mixture stirred at 20° C. for 15 min. Additional portions of 50% T3P in THF were added until reaction was complete. The reaction mixture was diluted with 10% brine (2 mL/g) and sodium hydroxide solution (2 mL/g) until pH8-10. The layers were separated, and the aqueous layer extracted with ethyl acetate (2×5 mL/g). The combined organic layers were washed with brine, dried (MgSO4) and concentrated to afford the title compound (80 g, 156 mmol, 71%) as a white triboluminesent solid. Chiral HPLC with chiral HPLC method 7 showed a single atropisomer, RT 12.62 min, 99.32% area (minor atropisomer, RT 10.58 min, 0.67% area)

Example 7

Biological Activity

A. Assay to Measure the Effects of Atropisomers A-1 and A-2 on U87MG Human Glioblastoma Cancer Cell Viability The following protocol was used to measure the effects of atropisomers A-1 and A-2 on U87MG cell viability. U87MG cells were grown in their recommended growth media/supplements (ATCC). Cells were seeded at a concentration of 5000 cells per well into 96 well plates overnight at 37° C., 5% $CO_2$. Cells were treated with relevant concentrations of test compound for 72 hours. After 72 h incubation, viability was established using sulforhodamine B (SRB) colorimetric assay. Percentage viability was calculated against the mean of the DMSO treated control samples, and IC50 values for inhibition of cell growth were calculated using GraphPad Prism software by nonlinear regression (4 parameter logistic equation).

The $IC_{50}$ values obtained for atropisomers A-1 and A-2 by following the above protocol are shown in Table 9 below.

TABLE 9

| Atropisomer | $IC_{50}$ (μM) |
|---|---|
| A-1 | 4.6 |
| A-2 | 0.22 |

B. Assay to Measure the Effects of Atropisomers A-1 and A-2 on Cancer Cell Viability of a Diverse Cancer Cell Line Panel Screening against diverse cancer cell lines was performed to identify tumour types displaying sensitivity to atropisomers A-1 and A-2. A panel of 48 cancer-derived cell lines was screened in a high-throughput proliferation assay using dilutions of atropisomers A-1/A-2. Cell lines that were screened included those representing cancer of the pancreas, large intestine/colorectum, lung, brain and nerves, and lymphoma and leukaemia cell lines. Cell lines were treated with serial half-log dilutions of compound and assayed 72 hours later for proliferation using CellTiter-Glo Assay (Promega). $IC_{50}$ values were calculated by fitting the dose-response data using a nonlinear regression model. The $IC_{50}$ values in micromolar for atropisomers A-1 and A-2 are shown in Table 10 below.

TABLE 10

| Cell Line | Tissue Origin | A-1 | A-2 |
|---|---|---|---|
| MIA PaCa-2 | Pancreas | 9.17 | 0.33 |
| PANC-1 | Pancreas | >10 | 0.83 |
| AsPC-1 | Pancreas | >10 | 2.9 |
| Capan-1 | Pancreas | >10 | 1.23 |
| Panc 10.05 | Pancreas | 9 | 1.14 |
| BxPC-3 | Pancreas | 6.97 | 0.3 |
| HCT 116 | Large intestine/Colorectum | 7.36 | 0.23 |
| LoVo | Large intestine/Colorectum | 8.36 | 0.54 |
| SW620 | Large intestine/Colorectum | 8.35 | 0.19 |
| SW480 | Large intestine/Colorectum | 7.55 | 0.87 |
| COLO 205 | Large intestine/Colorectum | 6.75 | 0.38 |
| HT-29 | Large intestine/Colorectum | 4.53 | 0.45 |
| RKO | Large intestine/Colorectum | 6.17 | 0.16 |
| A549 | Lung | 9.19 | 0.3 |
| NCI-H460 | Lung | 8.13 | 0.3 |
| HCC44 | Lung | 8.26 | 0.48 |
| NCI-H1373 | Lung | >10 | 3.21 |
| NCI-H1792 | Lung | 7.73 | 0.25 |
| NCI-H1299 | Lung | 8.25 | 0.37 |
| NCI-H1975 | Lung | 5.14 | 0.63 |
| SK-MES-1 | Lung | 7.78 | 0.36 |
| U118 MG | Brain&Nerves | 7.6 | 0.47 |
| A-172 | Brain&Nerves | 7.07 | 0.34 |
| LN-229 | Brain&Nerves | 7.37 | 0.31 |
| SW1088 | Brain&Nerves | 8.49 | 0.77 |
| T98G | Brain&Nerves | 5.26 | 0.28 |
| D283 Med | Brain&Nerves | 9.26 | 0.31 |
| Daoy | Brain&Nerves | 7 | 0.18 |
| DOHH-2 | Blood/Lymphoma | 5.64 | 0.23 |
| HBL-1 | Blood/Lymphoma | 9.94 | 0.66 |
| OCI-LY-19 | Blood/Lymphoma | 6.67 | 0.22 |
| SU-DHL-6 | Blood/Lymphoma | 3.98 | 0.26 |
| U-2932 | Blood/Lymphoma | 4.47 | 0.28 |
| WSU-DLCL2 | Blood/Lymphoma | 6.74 | 0.36 |
| SU-DHL-2 | Blood/Lymphoma | 7.01 | 0.2 |
| Toledo | Blood/Lymphoma | >10 | 0.88 |
| JeKo-1 | Blood/Lymphoma | 7.94 | 0.19 |
| Z-138 | Blood/Lymphoma | 7.04 | 0.21 |
| GRANTA-519 | Blood/Lymphoma | 7.42 | 0.22 |
| JVM-2 | Blood/Lymphoma | 4.71 | 0.38 |
| Daudi | Blood/Lymphoma | 7.17 | 0.39 |
| NAMALWA | Blood/Lymphoma | 7.05 | 0.25 |
| Raji | Blood/Lymphoma | 3.91 | 0.36 |
| Ramos | Blood/Lymphoma | 3.99 | 0.34 |
| ML-2 | Blood/Leukaemia | 4.01 | 0.18 |
| KG-1 | Blood/Leukaemia | >10 | 0.46 |
| MV-4-11 | Blood/Leukaemia | 6.49 | 0.28 |
| Kasumi-1 | Blood/Leukaemia | 5.13 | 0.33 |

As can be seen from the data, atropisomer A-2 was a significantly more active cell growth inhibitor than atropisomer A-1 against all of the cell lines C. Assay to Measure the Effects of Atropisomer A-2 on Cells in Mitosis Inhibiting the ability of PLK1 and PLK4 to bind to their partners through their PBDs is known to cause cells to arrest in mitosis. Experimentally, this can be measured by assessing the number of cells which are in mitosis at a certain time after treatment with a test compound by immunofluorescent detection of phosphorylated Histone H3 (pH3), a mark which is only present in mitotic cells. PLK1/4-PBD inhibitors are expected to cause a dose-dependent increase in pH3-positive cells, which is reported as Mitotic Index (MI)—the percentage of cells which, at a given time, are positive for this mitotic mark.

Distinct mitotic phenotypes are induced following inhibition of PLK1 and PLK4 in cells. Disruption of the PBD domain of PLK1 has been demonstrated to trigger mitotic arrest with non-congressed chromosomes, a distinct phenotype from the monopolar spindle phenotype induced by ATP-competitive PLK1 inhibitors (Hanisch et al., 2006 Mol. Biol. Cell 17, 448-459). Centriole assembly is controlled by PLK4, with inhibitors inducing a multipolar spindle phenotype due to centrosome defects which results in abnormal cyokinesis (Wong et al., 2015. Science 348(6239); 1155-1160).

The following protocol was used to measure the effects of atropisomer A-2 on arresting cells in mitosis and analysing the phenotype.

Mitotic Index and Phenotype Protocol

Cells were plated at 10 000/well in 96-well plates and incubated overnight. The following day atropisomer A-2 stocks in DMSO were diluted in medium then added to cells with a maximum final DMSO concentration on cells of 0.2%. Cells were incubated with the compound for 24 hours then fixed in 3.7% formaldeyde. Cells were permeabilised with 0.1% Triton X-100 then incubated with anti-phospho-histone H3 (Ser10) antibody (Abcam ab5176). The cells were washed with PBS then incubated with AlexaFluor 488 labelled goat anti-rabbit IgG (Invitrogen A11034) in the presence of 4 ug/ml Hoechst 33342 (Invitrogen H3570). Cells were washed in PBS then imaged on an Arrayscan VTi HCS instrument (Thermo Fisher) using the Target Activation V4 Bioapplication. A user-defined threshold was applied to identify mitotic cells based on the intensity of phospho-histone H3 staining.

GraphPad Prism was used to plot % mitotic cells against compound concentration using log(inhibitor) vs response variable slope with least squares fitting and no constraints.

From the results obtained by following the above protocol, the $EC_{50}$ values and the percentages of cells in mitosis against the HeLa and U87MG cell lines were obtained for atropisomer A-2. The $EC_{50}$ values are shown in Table 11 below.

TABLE 11

| Example | U87MG $EC_{50}$ (μM) | HeLa $EC_{50}$ (μM) |
|---|---|---|
| A-2 | 0.09 | 0.03 |

In a separate study, following the above protocol but using single compound concentrations of 0.03 μM for each of atropisomer A-1 and atropisomer A-2, the frequency of observed mitotic phenotypes in U87MG cells was manually assessed and classified into the following phenotypes: non-congressed chromosomes, multipolar spindles/abnormal cytokinesis, monopolar spindles, normal prometaphase, normal metaphase for each of A-1 and A-2. The results are shown in FIG. 10.

Figure 10:
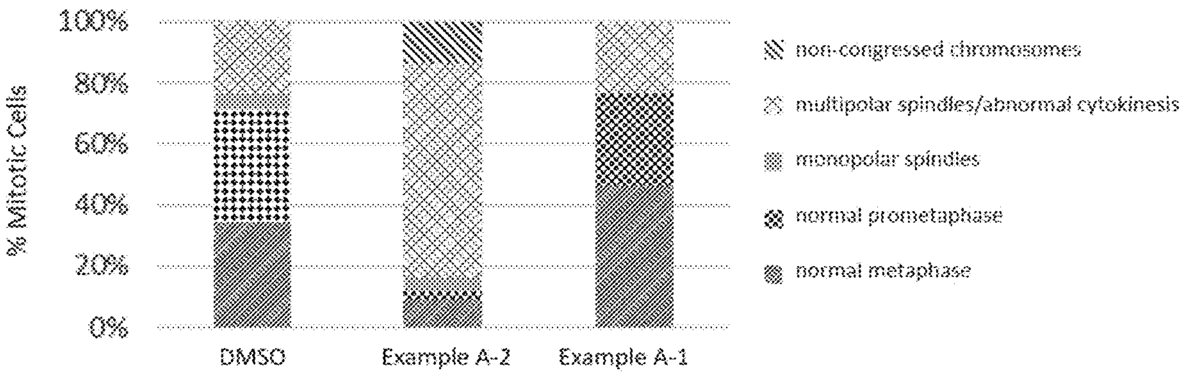
FIG. 10 is a bar chart showing the proportions of different observed mitotic phenotypes (non-congressed chromosomes, multipolar spindles/abnormal cytokinesis, monopolar spindles, normal prometaphase, normal metaphase produced after) after treating U87MG cells with 0.03 μM concentrations of either of atropisomer A-1 or atropisomer A-2.

The results presented in FIG. 10 demonstrate that the atropisomer A-2 has a much greater effect on disrupting normal mitosis than atropisomer A-1. Thus, with A-1, 76% of the cells displayed a normal mitotic phenotype, comparable to 77% of the cells treated with DMSO control, and 24% displayed abnormal cytokinesis copared to 23% treated with DMSO control. No evidence of a non-congressed chromosome phenotype was seen in either DMSO control or atropisomer A-1 treated cells. By contrast, treatment of the cells with the more active atropisomer A-2 resulted in only 17% of cells with normal mitotic phenotype, 70% with abnormal cytokinesis and 13% with non-congressed chromosomes. These phenotypes are consistent with disrupting PLK1 and PLK4 activity during mitosis.

D. Assay to Measure the Effects of Atropisomer A-2 on Centrosomes

Figure 11:
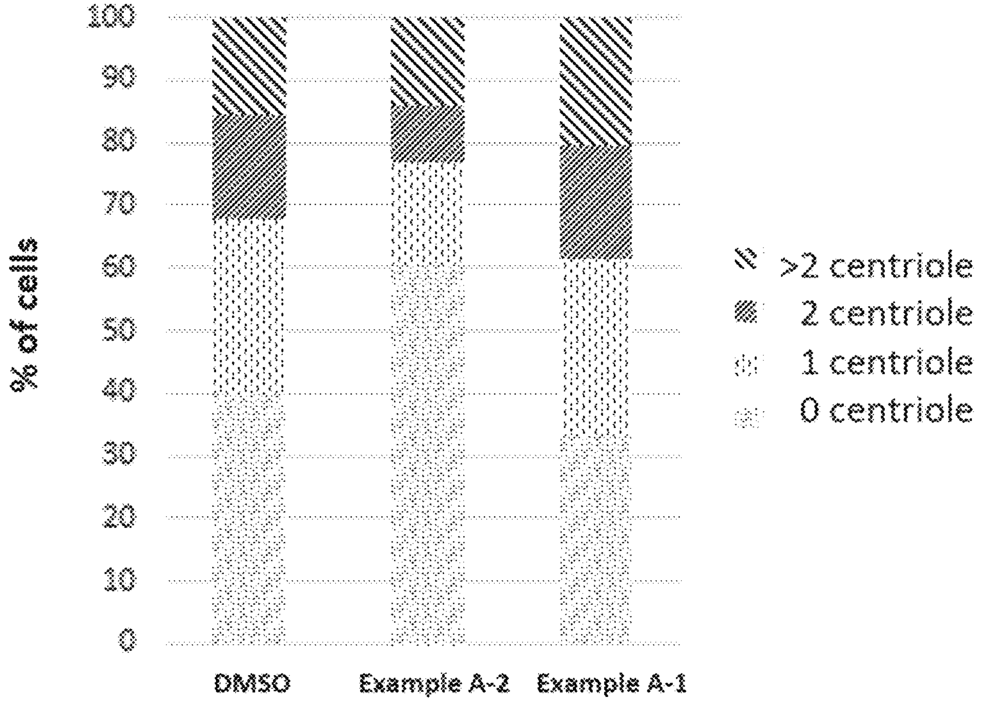
FIG. 11 is a bar chart showing the numbers of centrioles present in HeLa cells after treatment with 0.02 μM concentrations of either of atropisomer A-1 or atropisomer A-2.

The results of study C above show that atropisomer A-2 causes mitotic effects which are characteristic of dysregulated centrosome function. The effect of A-2 on centrosome function was therefore investigated further. HeLa cells stably expressing a Centrin1-GFP fusion protein were seeded into 96-well plates overnight. Cells were treated with atropisomer A-2 (at a concentration of 0.02 μM in DMSO) or DMSO control for 72 hours and then imaged using a fluorescence microscope. Multiple cell fields were captured for each treatment condition, and the images were subsequently analysed manually. Centrin1-GFP specifically marks centrioles as discrete foci, and therefore can be used to quantitate centriole number per cell. Thus, for each treatment condition, 100 cells were analysed and the number of centrioles present in each cell was recorded. The data were then separated into bins (no centrioles, 1 centriole, 2 centrioles, and greater than 2 centrioles) and are shown in FIG. 11.

From the data, it can be concluded that atropisomer A-2 exhibits evidence of PLK4 inhibition phenotypes on HeLa cells.

E. Assay to Measure the Effects of Atropisomer A-2 on Wild-Type Versus KRAS HeLa Cell Viability An assay was carried out to compare the effects of atropisomer A-2 against wild type HeLa cells and HeLa cells harbouring a KRAS oncogene.

Thus, atropisomer A-2 was tested on HeLa cells engineered to inducibly express wild-type or oncogenic KRasG12V transgenes using the FLP-in/T-Rex system (Invitrogen). Cells were plated, and then treated with or without doxycycline to induce transgene expression, and then treated with serially-diluted atropisomer A-2. After 72 hours of incubation, cell viability was assessed using the Cell Titre Blue reagent (Promega) and a BMG Pherastar plate reader. The effect of PBD inhibition on cell viability with either wild-type or oncogenic G12V KRAS was assessed using GraphPad Prism.

From the results obtained by following the above protocol, the $GI_{50}$ values against the wild-type and KRAS G12V HeLa cell line were determined for atropisomer A-2 and are shown in Table 12 below.

TABLE 12

| Atropisomer | WT $GI_{50}$ (nM) | G12V $GI_{50}$ (nM) |
|---|---|---|
| A-2 | 3.01 | 2.08 |

F. Kinase Selectivity Assay

The evidence provided herein indicates that Atropisomer A-2 binds to the PBD domains of PLK1 and PLK4 but not to the catalytic domains of PLK1 and PLK4 and should exhibit good selectivity over other kinases. This has been investigated by testing atropisomer A-2 for off-target activity against a panel of ninety-seven kinases distributed across the kinome at a concentration of 3 μM using the DiscoverX KinomeScreen assay.

The DiscoverX KinomeScreen assay is a site-directed competition binding assay which measures the binding affinity of a compound to a kinase, by use of a solid supported control compound which can bind or capture the kinases in solution. In the absence of a kinase-inhibitor test compound, all of the kinase will bind to the solid support. If a kinase-inhibitor test compound is added to the assay mix, the amount of kinase binding to the solid support will be reduced, the extent of reduction being dependent on the potency of the test compound as a kinase inhibitor. The potencies of the test compounds against the kinases can be expressed as the percentage (Percent Control) of the kinase binding to the solid support at a given concentration of the test compound, the lower the percentage the more potent the kinase-binding capability of the test compound. Thus, a Percent Control value of 100% would indicate that the test compound does not bind to the kinase at all, since all of the kinase has bound to the solid support. Conversely, a Percent Control value of 0% would indicate that the test compound has bound all of the kinase since none is bound to the solid support.

Protocol:

For most assays, kinase-tagged T7 phage strains were grown in parallel in 24-well blocks in an *E. coli* host derived from the BL21 strain.

*E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Compounds that bind the kinase active site and directly (sterically) or indirectly (allosterically) prevent kinase binding to the immobilized ligand, will reduce the amount of kinase captured on the solid support. Conversely, test molecules that do not bind the kinase have no effect on the amount of kinase captured on the solid support.

The strength of binding of the test molecule to the kinase can be expressed as the percent control (% Ctrl)

Percent Control (% Ctrl)

The compound(s) were screened at 3000 nM concentration, and results for primary screen binding interactions are reported as '% Ctrl', where lower numbers indicate stronger hits in the matrix on the following page(s).

% *Ctrl* Calculation $$\left(\frac{\text{test compound signal} - \text{positive control signal}}{\text{negative compound signal} - \text{positive control signal}}\right) \times 100$$

negative control=DMSO (100% Ctrl)

positive control=control compound (0% Ctrl)

The % Ctrl values for atropisomer A-2 against the panel kinases are set out in Table 13 below.

TABLE 13

| Gene Symbol | % Ctrl @ 3 μM | Gene Symbol | % Ctrl @ 3 μM |
|---|---|---|---|
| ABL1 | 100 | STK11 | 81 |
| ABL1 | 100 | MAP3K4 | 93 |
| ABL1 | 100 | MAPKAPK2 | 75 |
| ABL1 | 97 | MARK3 | 100 |
| ACVR1B | 96 | MAP2K1 | 84 |
| CABC1 | 63 | MAP2K2 | 81 |
| AKT1 | 98 | MET | 100 |
| AKT2 | 100 | MKNK1 | 92 |
| ALK | 89 | MKNK2 | 85 |
| AURKA | 98 | MAP3K9 | 96 |
| AURKB | 84 | MAPK14 | 100 |
| AXL | 93 | MAPK11 | 99 |
| BMPR2 | 82 | PAK1 | 87 |
| BRAF | 96 | PAK2 | 100 |
| BRAF | 100 | PAK4 | 100 |
| BTK | 94 | CDK16 | 100 |
| CDK19 | 81 | PDGFRA | 100 |
| CDK2 | 94 | PDGFRB | 100 |
| CDK3 | 100 | PDPK1 | 96 |
| CDK7 | 100 | PIK3C2B | 100 |
| CDK9 | 97 | PIK3CA | 100 |
| CHEK1 | 100 | PIK3CG | 100 |
| CSF1R | 100 | PIM1 | 99 |
| CSNK1D | 91 | PIM2 | 100 |
| CSNK1G2 | 100 | PIM3 | 98 |
| DCLK1 | 87 | PRKACA | 100 |
| DYRK1B | 97 | PLK1 | 97 |
| EGFR | 100 | PLK3 | 87 |
| EGFR | 100 | PLK4 | 100 |
| EPHA2 | 100 | PRKCE | 99 |
| ERBB2 | 66 | RAF1 | 92 |
| ERBB4 | 99 | RET | 95 |
| MAPK3 | 99 | RIOK2 | 100 |
| PTK2 | 98 | ROCK2 | 88 |
| FGFR2 | 85 | RPS6KA3 | 100 |
| FGFR3 | 92 | NUAK2 | 99 |
| FLT3 | 100 | SRC | 100 |
| GSK3B | 88 | SRPK3 | 71 |
| IGF1R | 100 | TGFBR1 | 95 |
| CHUK | 100 | TEK | 99 |
| IKBKB | 96 | NTRK1 | 100 |
| INSR | 100 | TSSK1B | 100 |
| JAK2 | 80 | TYK2 | 100 |
| JAK3 | 100 | ULK2 | 93 |
| MAPK8 | 77 | KDR | 100 |
| MAPK9 | 80 | STK32C | 100 |
| MAPK10 | 93 | ZAP70 | 92 |
| KIT | 100 | | |
| KIT | 100 | | |
| KIT | 100 | | |

The results against ninety-seven kinases demonstrate that atropisomer A-2 has poor or non-existent binding activity against a wide range of kinases and therefore is unlikely to suffer from problems associated with off-target kinase inhibition.

In the case of PLK1 and PLK4, atropisomer A-2 showed little or no binding affinity for the catalytic domains of these kinases (% Control values of 97% and 100% respectively). It is concluded therefore that the activity profiles indicative of PLK1/PLK4 inhibitory activity demonstrated in the examples above is a consequence of to the non-catalytic polo box domains of PLK1 and PLK4.

G. Determination of Oral Bioavailability and Brain Exposure in Mouse PK

Atropisomer A-2 was evaluated in an in vivo mouse model to determine brain and plasma concentrations following p.o. and i.v. dosing.

The following protocol was followed:

Male CD-1 mice were dosed with atropisomer A-2, either by i.v. administration (2 mg/kg) or by p.o. administration (10 mg/kg).

Eight samples were taken for analysis in the i.v. leg at 2, 10, 30 min, 1, 2, 4, 8, and 24 (for i.v) and 9 samples in the p.o. leg at 15, 30 min, 1, 2, 4, 8, 24, 48 and 72 hrs.

Atropisomer A-2 was formulated in 10% DMSO/95% hydroxypropyl-beta-cyclodextrin (20% w/v in water) for i.v. and p.o. dosing. N=3 mice per time point.

Post dosing, terminal blood samples were taken from individual animals and delivered into labelled polypropylene tubes containing anticoagulant (EDTA). The samples were held on wet ice for a maximum of 30 min while sampling of all the animals in the cohort was completed. The blood samples were centrifuged for plasma (4° C., 21100 g for 5 min) and the resulting plasma transferred into corresponding labelled tubes. Terminal brains from each PO dosed animal were excised, rinsed with saline and placed into pre-weighed labelled polypropylene tubes and the samples re-weighed prior to storage.

Figure 12:
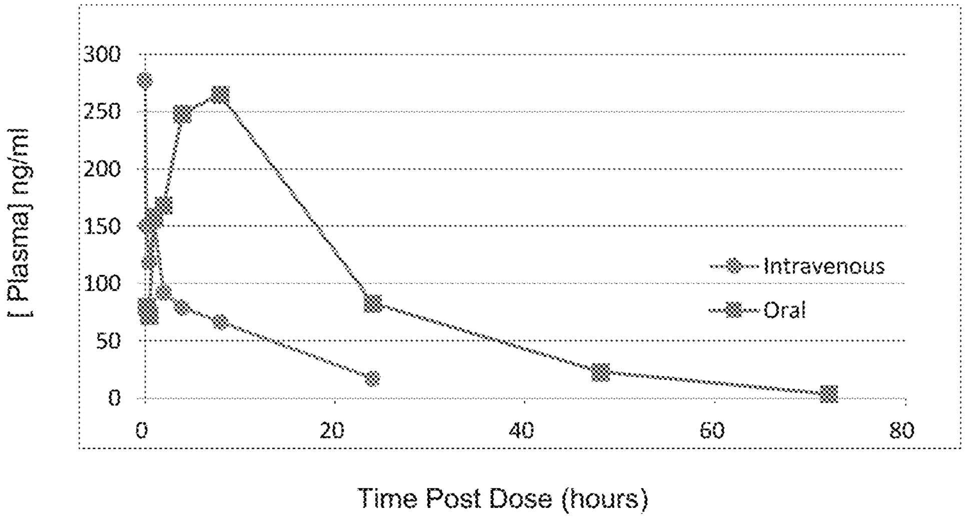
FIG. 12 is a plot of blood plasma concentrations against time following oral and i.v. dosing to mice of atropisomer A-2. The lower line, extending as far as 24 hours, is the line for the 2 mg/kg i.v. dose. The other line is for the 10 mg/kg p.o. dose.
Figure 13:
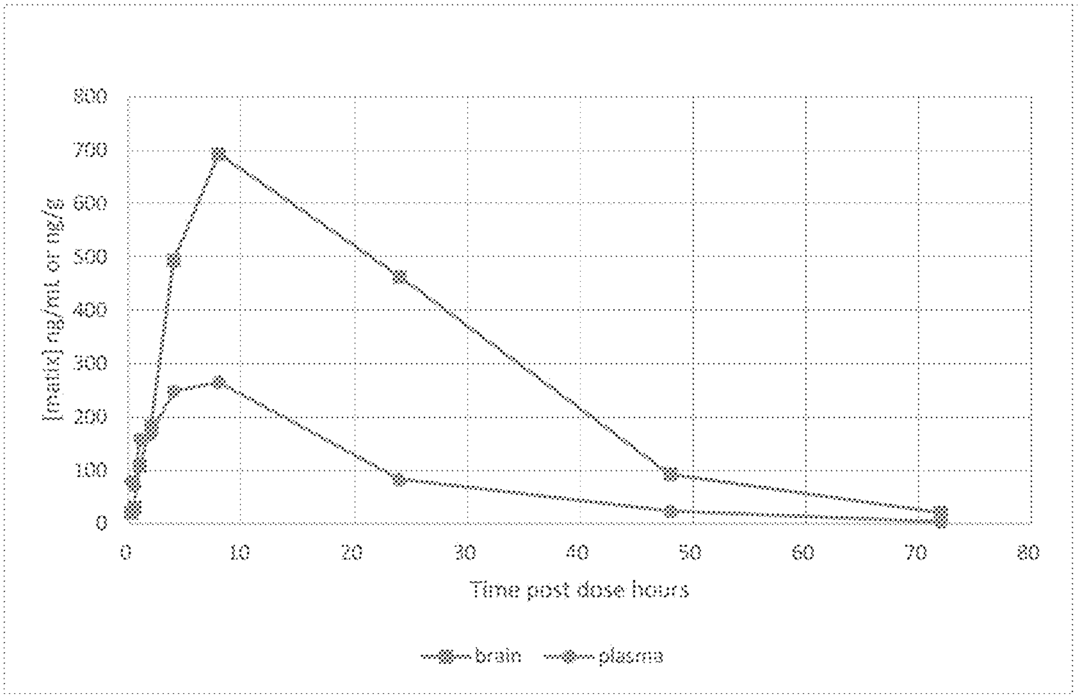
FIG. 13 is a plot of blood plasma and brain concentrations against time following oral dosing (10 mg/kg) to mice of atropisomer A-2. The upper line shows the brain concentrations while the lower line shows the plasma concentrations.

Quantitative bioanalysis was carried out using liquid chromatography—mass spectroscopy was performed. The results are shown in Tables 14 and 15 below and in FIGS. 12 and 13.

Oral Bioavailability

TABLE 14

| 2 mg/Kg IV | | |
|---|---|---|
| Parameter | Units | Atropisomer A-2 |
| T½ | hr | 9.0 |
| CI | mL/min/kg | 20.5 |
| Cmax | ng/mL | 278 |
| AUCinf | ng · hr/mL | 1624 |

TABLE 15

| 10 mg/Kg PO | | |
|---|---|---|
| Parameter | Units | Atropisomer A-2 |
| T½ | hr | 10.7 |
| Cmax | ng/mL | 265 |
| AUCinf | ng · hr/mL | 6131 |
| F | % | 76 |

The results demonstrate that atropisomer A-2 is highly absorbed following oral dosing in mice.

Brain Exposure

TABLE 16

| Parameter | Units | Atropisomer A-2 |
|---|---|---|
| T½ | hr | 12.1 |
| Tmax | hr | 8.0 |
| Cmax | ng/mL | 693 |
| AUClast plasma | ng · hr/mL | 6131 |
| AUClast brain | ng · hr/mL | 20528 |

The results of the brain exposure studies presented in Table 16 demonstrate that atropisomer A-2 has high brain exposure with an AUC B:P ratio of 3.3 following oral dosing in mice.

H. In Vivo Efficacy

Atropisomer A-2 shows efficacy in glioblastoma mouse models when tumours are implanted subcutaneously and orthotopically, as indicated by the studies described below.

(i) In vivo anti-cancer activity in U87MG subcutaneous xenograft model

Figure 14:
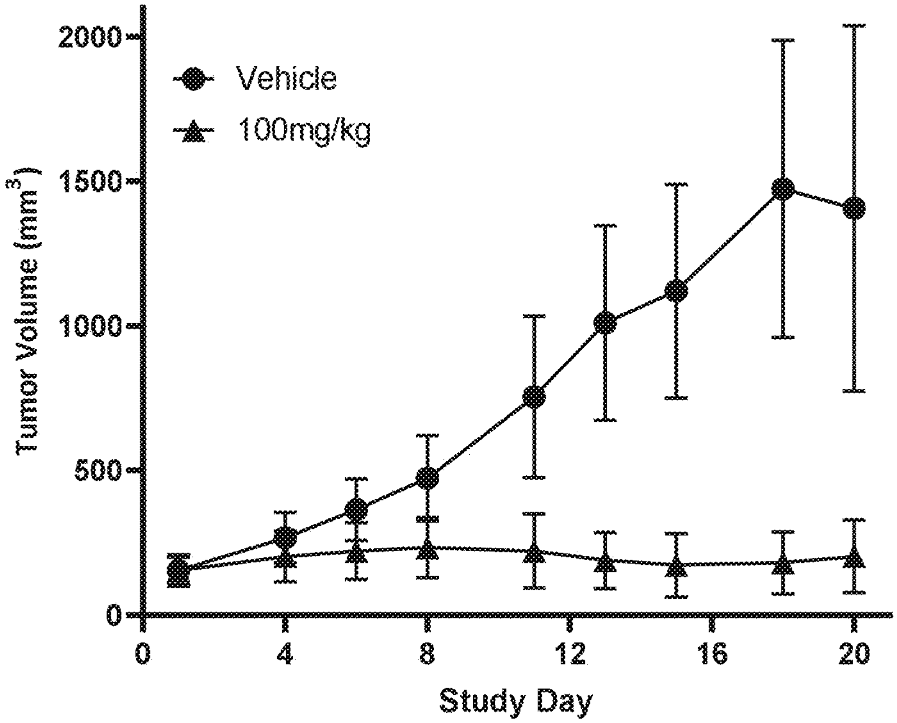
FIG. 14 is a plot of tumour volume versus time in male athymic nude mice in a U87MG subcutaneous xenograft model after administration of atropisomer A-2.

Male athymic nude mice bearing U87MG tumours were given an oral dose of 100 mg/kg of atropisomer A-2 on days 1, 4 and 7 and the tumour volumes were measured over 20 days. Tumour volumes in a control group of tumour-bearing mice, who had received vehicle only at the same time points were also measured. The treated group showed significantly decreased tumour volume compared to control (3.85% T/C at day 13), as shown in FIG. 14.

(ii) In Vivo Anti-Cancer Activity in U87-Luc Orthotopic Xenograft Model

Figure 15:
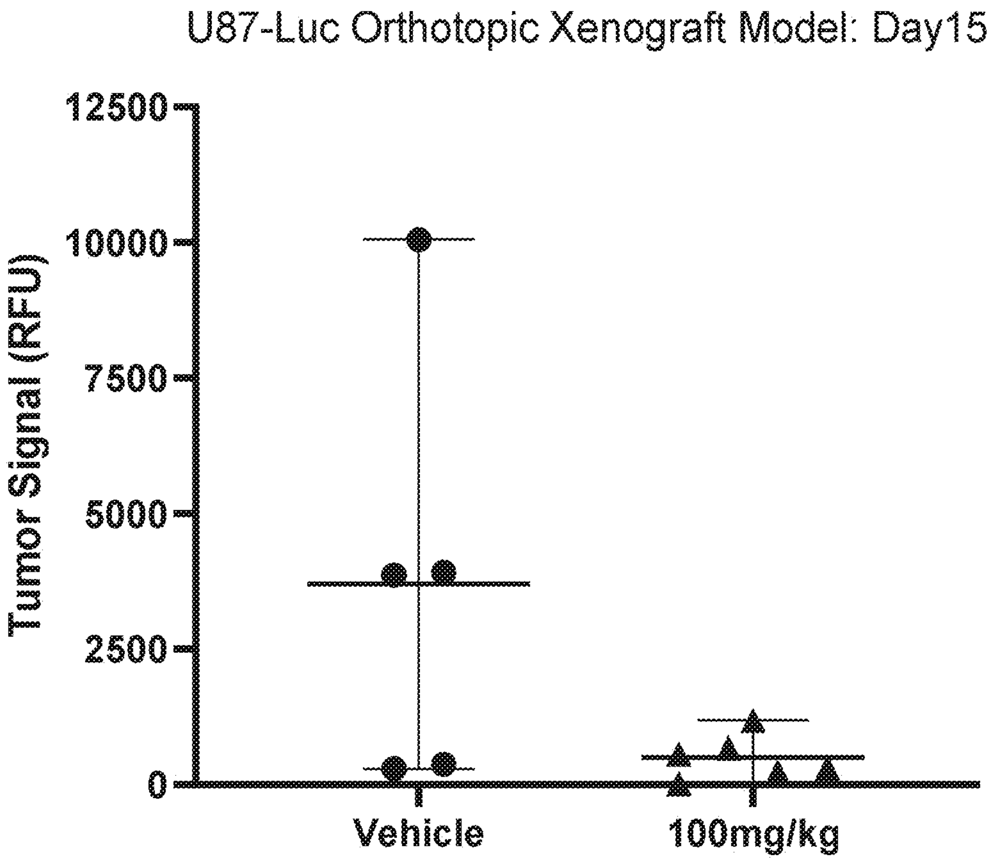
FIG. 15 is a graphic comparison of bioluminescent signal linked to tumour growth in male athymic nude mice in a U87-Luc orthotopic xenograft model after administration of atropisomer A-2.

U87-Luc cells were intracerebrally implanted into the brains of male athymic nude mice and tumour growth was monitored by bioluminescent signal. In the treatment group animals were given an oral dose of 100 mg/kg of atropisomer A-2 on days 1, 4, 7, 10 and 13. The control group animals were given vehicle only. The results, shown in FIG. 15, demonstrate a decrease in tumour signal for the treated verses the control group on Day 15.

(iii) In Vivo Anti-Cancer Activity in Mice Bearing HCT116 Tumours

Atropisomer A-2 has shown efficacy in a KRAS mutated colorectal cancer model, as described below.

Male athymic nude mice bearing HCT116 xenograft tumours were give an oral dose of 100 mg/kg atropisomer A-2 on days 1, 8 and 15 and the tumour volumes were measured over 3 weeks. Tumour volumes in a control group of tumour-bearing mice, who had received vehicle only at the same time points were also measured.

Figure 16:
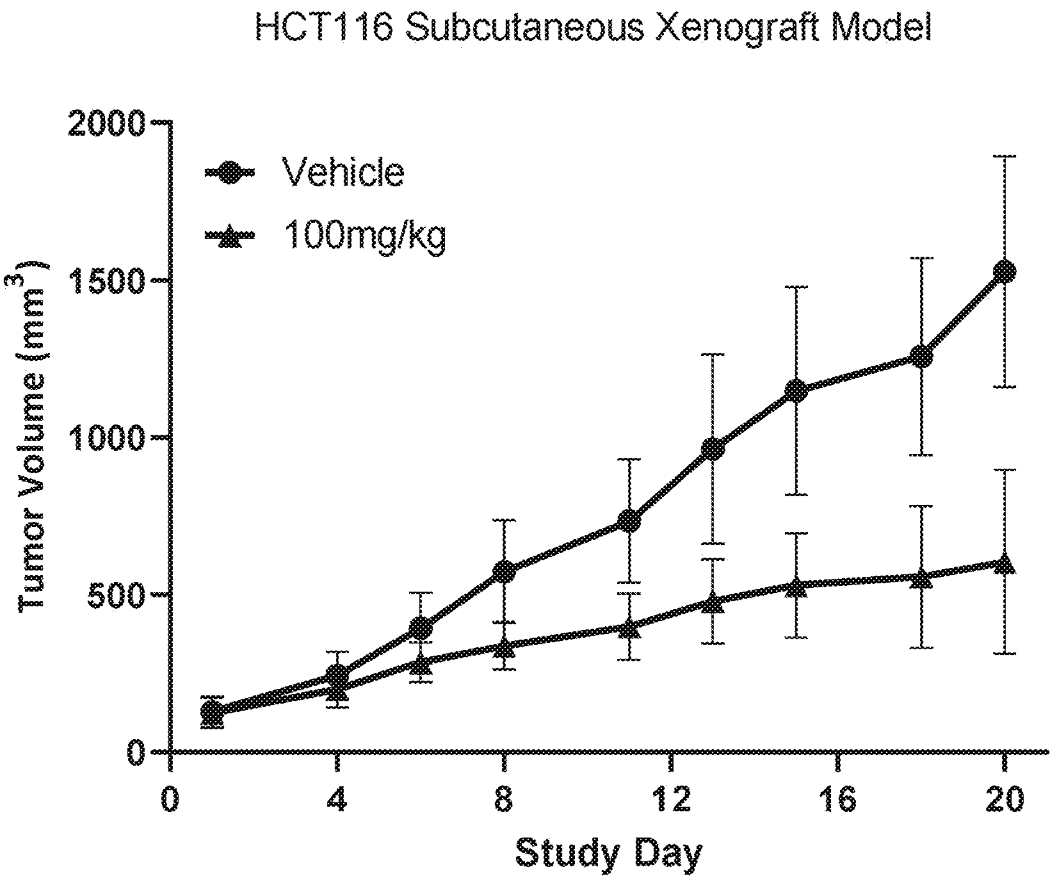
FIG. 16 is a plot of tumour volume versus time in male athymic nude mice in an HCT116 subcutaneous xenograft model after administration of atropisomer A-2.

The results, shown in FIG. 16, demonstrate a pronounced effect on tumour growth at day 20 (TGI 60%).

Pharmaceutical Formulations (i) Tablet Formulation

A tablet composition containing a tartaric acid salt or a composition of matter according to any one of Embodiments 1.1 to 1.19 or the Examples above is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a tartaric acid salt or a composition of matter according to any one of Embodiments 1.1 to 1.19 or the Examples above with 100 mg lactose and filling the resulting mixture into standard opaque hard gelatin capsules.

(iii) Injectable Formulation I

A parenteral composition for administration by injection can be prepared by dissolving a tartaric acid salt or a composition of matter according to any one of Embodiments 1.1 to 1.19 or the Examples above in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a a tartaric acid salt or a composition of matter according to any one of Embodiments 1.1 to 1.19 or the Examples above (2 mg/ml) and mannitol (50 mg/ml), sterile filtering the solution and filling into sealable 1 ml vials or ampoules.

(v) Injectable formulation III

A formulation for i.v. delivery by injection or infusion can be prepared by dissolving a composition of matter according to any one of Embodiments 1.1 to 1.19 or the Examples above in water at 20 mg/ml. The vial is then sealed and sterilised by autoclaving.

(vi) Injectable Formulation IV

A formulation for i.v. delivery by injection or infusion can be prepared by dissolving a composition of matter according to any one of Embodiments 1.1 to 1.19 or the Examples above in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a composition of matter according to any one of Embodiments 1.1 to 1.19 or the Examples above with pharmaceutical grade corn oil to give a concentration of 5 mg/ml. The composition is sterilised and filled into a suitable container.

(viii) Lyophilised Formulation

Aliquots of formulated a composition of matter according to any one of Embodiments 1.1 to 1.19 or the Examples above are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. (R)-4-[5-(4-chlorophenyl)-1-[2-(trifluoromethyl)-phenyl]pyrrol-2-yl]-N-[2-(dimethylamino)-ethyl]benzamide (+)-L-tartaric acid salt having an approximately 1:1 molar ratio between acid and base.

2. A (+)-L-tartaric acid salt of 4-[5-(4-chlorophenyl)-1-[2-(trifluoromethyl)-phenyl]pyrrol-2-yl]-N-[2 (dimethylamino)ethyl]benzamide having the formula (2):

(2)

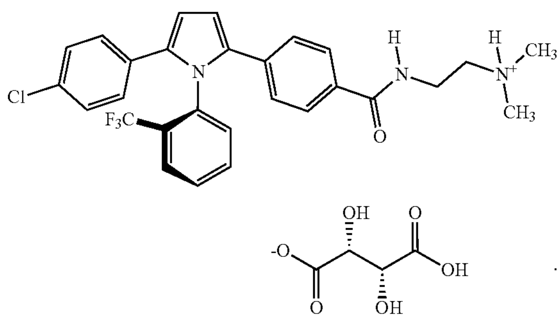

.

3. A (+)-L-tartaric acid salt of 4-[5-(4-chlorophenyl)-1-[2-(trifluoromethyl)-phenyl]pyrrol-2-yl]-N-[2 (dimethylamino)ethyl]benzamide, in which there is an approximately 1:1 molar ratio between acid and base and wherein the 4-[5-(4-chlorophenyl)-1-[2-(trifluoromethyl)-phenyl]pyrrol-2-yl]-N-[2 (dimethylamino)ethyl]-benzamide is in the form of a single atropisomer.

4. A (+)-L-tartaric acid salt according to claim 3 wherein the single atropisomer is an atropisomer of formula (1)

(1)

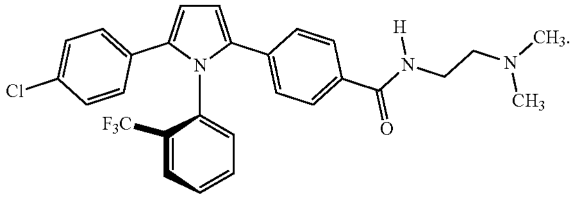

5. A (+)-L-tartaric acid salt according to claim 3 wherein the single atropisomer is the R atropisomer of 4-[5-(4-chlorophenyl)-1-[2-(trifluoromethyl)-phenyl]pyrrol-2-yl]-N-[2 (dimethylamino)ethyl]benzamide.

6. A (+)-L-tartaric acid salt according to claim 1 which is in a crystalline form.

7. A (+)-L-tartaric acid salt according to claim 6 which is an anhydrate.

8. A composition of matter comprising the (+)-L-tartaric acid salt of claim 1 wherein either (a) the single atropisomer is the only atropisomer of 4-[5-(4-chlorophenyl)-1-[2-(trifluoromethyl)-phenyl]pyrrol-2-yl]-N-[2 (dimethylamino) ethyl]benzamide present in the composition or (b) there is less than 10% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino)ethyl]benzamide.

9. A composition of matter according to claim 8 wherein either (a) the single atropisomer is the only atropisomer of 4-[5-(4-chlorophenyl)-1-[2-(trifluoromethyl)-phenyl]pyrrol-2-yl]-N-[2 (dimethylamino)ethyl]benzamide present in the composition or (b) there is less than 0.1% by molar amount, relative to the said single atropisomer, of any other atropisomer of 4-[5-(4-chlorophenyl)-1-[2-(trifluoromethyl)-phenyl]pyrrol-2-yl]-N-[2 (dimethylamino)ethyl]benzamide.

10. A pharmaceutical composition comprising a (+)-L-tartaric acid salt as defined in claim 1 and a pharmaceutically acceptable excipient.

11. A pharmaceutical combination comprising a (+)-L-tartaric acid salt according to claim 1 and another therapeutically active agent.

12. A pharmaceutical combination comprising a composition of matter according to claim 9 and another therapeutically active agent.

13. A pharmaceutical composition comprising a composition of matter according to claim 8 and a pharmaceutically acceptable excipient.

14. A method of treating a cancer, the method comprising administering to a subject in need thereof a (+)-L-tartaric acid salt as defined in claim 1.

15. A method of treating a cancer, the method comprising administering to a subject in need thereof a composition of matter as defined in claim 8.

16. A method according to claim 14 wherein the cancer is selected from:

a) pancreatic cancer, cancers of the large intestine and colorectum, lung cancers, breast cancers, ovarian cancers, prostate cancers and cancers of the brain and nerves;

b) blood cancers such as lymphoma, leukaemia, and myelodysplastic syndromes, including AML, ALL, B and T cell lymphomas;

c) gliomas and glioblastomas (which may, for example, be selected from glioblastoma multiforme, ependymomas, diffuse intrinsic pontine glioma, IDH1 mutant gliomas);

d) rhabdoid tumours; medulloblastoma and other embryonal tumours of the brain; breast, lung, melanoma, gastric, colorectal, pancreatic and ovarian cancer;

e) sarcomas, including rhabdomyosarcoma, osteosarcoma;

f) a cancer in which PLK1 is implicated (e.g. wherein PLK1 is overexpressed);

g) a cancer in which PLK4 is implicated (e.g. wherein PLK4 is overexpressed);

h) a cancer which is characterised by p53 deficiency or mutation in the TP53 gene; and i) a cancer which is characterised by the presence of a mutated form of KRAS.

17. A method of inhibiting PLK1 kinase and/or PLK4 kinase, which method comprises bringing an effective inhibiting amount of a (+)-L-tartaric acid salt as defined in claim 1 into contact with the PLK1-PBD and/or the PLK14-PBD, thereby inhibiting the PLK1 kinase and/or the PLK4 kinase.

18. A salt according to claim 1 wherein at least 90% of the 4-[5-(4-chlorophenyl)-1-[2-(trifluoromethyl)-phenyl]pyrrol-2-yl]-N-[2-(dimethylamino)-ethyl]benzamide present is (R)-4-[5-(4-chlorophenyl)-1-[2-(trifluoromethyl)-phenyl]pyrrol-2-yl]-N-[2-(dimethylamino)-ethyl]benzamide.

19. A salt according to claim 2 wherein at least 90% of the 4-[5-(4-chlorophenyl)-1-[2-(trifluoromethyl)-phenyl]pyrrol-2-yl]-N-[2 (dimethylamino)ethyl]benzamide present is of formula (1):

(1)

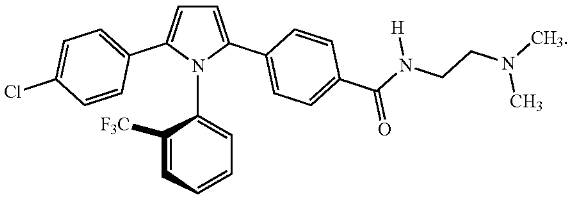

* * * * *